US012161681B2

(12) United States Patent
Rescigno et al.

(10) Patent No.: US 12,161,681 B2
(45) Date of Patent: Dec. 10, 2024

(54) POSTBIOTIC-BASED COMPOSITION FOR THE MODULATION OF IMMUNE SYSTEM ACTIVATION AND PROTECTION OF MUCOSAL BARRIERS

(71) Applicant: POSTBIOTICA S.R.L., Milan (IT)

(72) Inventors: Maria Rescigno, Milan (IT); Giuseppe Penna, Milan (IT); Francesca Algieri, Milan (IT)

(73) Assignee: POSTBIOTiCA S.R.L., Milan (IT)

( * ) Notice: Subject to any disclaimer, the term of this patent is extended or adjusted under 35 U.S.C. 154(b) by 424 days.

(21) Appl. No.: 16/965,471

(22) PCT Filed: Feb. 4, 2019

(86) PCT No.: PCT/EP2019/052669
§ 371 (c)(1),
(2) Date: Jul. 28, 2020

(87) PCT Pub. No.: WO2019/149941
PCT Pub. Date: Aug. 8, 2019

(65) Prior Publication Data
US 2021/0052678 A1 Feb. 25, 2021

(30) Foreign Application Priority Data

Feb. 2, 2018 (IT) .................. 102018000002370

(51) Int. Cl.
A61K 35/747 (2015.01)
A23K 10/16 (2016.01)
A23L 33/135 (2016.01)
A61K 8/60 (2006.01)
A61K 8/99 (2017.01)
A61K 9/00 (2006.01)
A61K 9/08 (2006.01)
A61K 45/06 (2006.01)
A61K 47/26 (2006.01)
A61P 31/04 (2006.01)
A61P 37/06 (2006.01)
A61Q 19/00 (2006.01)
C12N 1/20 (2006.01)
C12R 1/245 (2006.01)

(52) U.S. Cl.
CPC ............ A61K 35/747 (2013.01); A23K 10/16 (2016.05); A23L 33/135 (2016.08); A61K 8/60 (2013.01); A61K 8/99 (2013.01); A61K 9/0031 (2013.01); A61K 9/0048 (2013.01); A61K 9/08 (2013.01); A61K 45/06 (2013.01); A61K 47/26 (2013.01); A61P 31/04 (2018.01); A61P 37/06 (2018.01); A61Q 19/00 (2013.01); C12N 1/20 (2013.01); C12N 1/205 (2021.05); A23V 2002/00 (2013.01); A61K 2800/10 (2013.01); A61K 2800/85 (2013.01); C12R 2001/245 (2021.05)

(58) Field of Classification Search
None
See application file for complete search history.

(56) References Cited

U.S. PATENT DOCUMENTS

2004/0204472 A1* 10/2004 Briggs ................. A61K 31/366
514/406
2010/0254956 A1* 10/2010 Arulampalam ........... A61P 3/04
424/780

FOREIGN PATENT DOCUMENTS

| EP | 2402432 A1 | 1/2012 |
| KR | 10-2004-0006886 A | 1/2004 |
| WO | 2011009848 A2 | 1/2011 |
| WO | 2017204374 A1 | 11/2017 |
| WO | 2017212433 A1 | 12/2017 |
| WO | 2018024833 A1 | 2/2018 |

OTHER PUBLICATIONS

Sen et al., "Modeling and optimization of the process conditions for biomass production and sporulation of a probiotic culture", Process Biochemistry, vol. 40, pp. 2531-2538. (Year: 2005).*
Hernandez-Hernandez et al., "Effect of prebiotic carbohydrates on the growth and tolerance of Lactobacillus", Food Microbiology, vol. 30, pp. 355-361. (Year: 2012).*
"Maximum Strength Fungus Treatment", Database GNPD [Online] MINTEL, 2003, XP055507856, pp. 1-2.
Makarova et al., "Comparative genomics of the lactic acid bacteria", Proceedings of the National Academy of Sciences, 2006, vol. 103, No. 42, pp. 15611-15616.
Mileti et al., "Comparison of the Immunomodulatory Properties of Three Probiotic Strains of Lactobacilli Using Complex Culture Systems: Prediction for In Vivo Efficacy", PLOS ONE, 2009, vol. 4, No. 9, pp. 1-16.
Broadbent et al., "Influence of polysorbate 80 and cyclopropane fatty acid synthase activity on lactic acid production by Lactobacillus casei ATCC 334 at low pH", Journal of Industrial Microbiology and Biotechnology, 2014, vol. 41, No. 3, pp. 545-553.
International Search Report and Written Opinion for Corresponding International Application No. PCT/EP2019/052669, (Apr. 26, 2019) (17 Pages), Correction: 11 pages.
Search Report for Corresponding Italian Application No. IT 201800002370 ( Oct. 1, 2018) (10 Pages).

(Continued)

Primary Examiner — Michelle F. Paguio Frising
Assistant Examiner — Grant C Currens
(74) Attorney, Agent, or Firm — Lucas & Mercanti, LLP

(57) ABSTRACT

The present invention refers to a composition containing a) a fermented supernatant, or fractions thereof, of Lactobacillus casei or paracasei species, the species being characterized by having in their DNA genome at least one DNA sequence essentially identical to one of the sequence selected from the group consisting of: SEQ ID No 1 to 5, and b) proper carriers and/or diluents and/or excipients. The fermented supernatant is obtainable through a method characterized by the fermentation of the Lactobacillus casei or paracasei species in a minimum solution additioned with prebiotic fibers. The fermented supernatant does not have prebiotic fibers.

Figure 1:
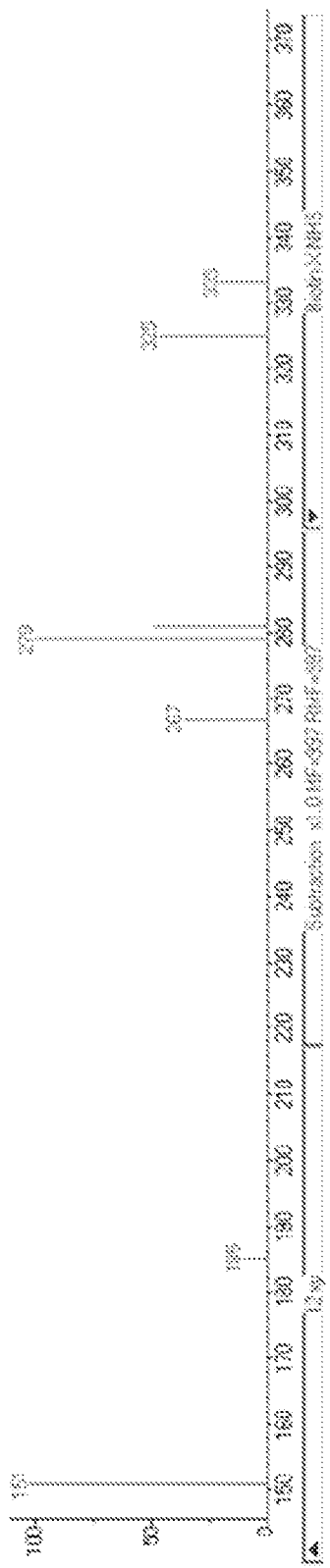

22 Claims, 16 Drawing Sheets
Specification includes a Sequence Listing.

(56) References Cited

OTHER PUBLICATIONS

EPO, Office Action issued for the corresponding European Patent Application No. 19705930.6, dated Jun. 29, 2023, 12 pages.
C. C. Sieo, et al., "Effect of prebiotic oligosaccharides on growth of Lactobacillus strains used as a probiotic for chickens," 2011, African Journal of Microbiology Research, vol. 5 n.1, p. 57-64.
C.E. Rycroft, et al., "A comparative in vitro evaluation of the fermentation properties of prebiotic oligosaccharides," 2001, Journal of Applied Microbiology, vol. 91 n. 5, p. 878-887.
Siok-Koon Yeo, et al., "Effect of prebiotics on viability and growth characteristics of probiotics in soymilk," 2010, Journal of the Science of Food and Agriculture, vol. 90 n. 2, p. 267-275.

* cited by examiner

SEQUENCE LISTING

<160> NUMBER OF SEQ ID NOS: 19

<210> SEQ ID NO 1
<211> LENGTH: 165
<212> TYPE: DNA
<213> ORGANISM: Lactobacillus casei and Lactobacillus paracasei

<400> SEQUENCE: 1

```
atgaatcaaa aagctttgaa tcaatttcct gaacttacct acacagaaca agtgtcggtt      60
gttggcggcg atttgtcagt cgaagtcatc atgaaaggta tcttcaccgg tatctttgat     120
gctgggtacc aagtgggtca gtcaatcgca aaatgggtta agtaa                     165
```

<210> SEQ ID NO 2
<211> LENGTH: 108
<212> TYPE: DNA
<213> ORGANISM: Lactobacillus casei and Lactobacillus paracasei

<400> SEQUENCE: 2

```
atgaaaggta agcggcagca cttactttta tattttgttc tgggtatgat gacaggactg      60
gtgacggcag cgattttca tatcatttat gcctggcttt ttcattga                   108
```

<210> SEQ ID NO 3
<211> LENGTH: 462
<212> TYPE: DNA
<213> ORGANISM: Lactobacillus casei and Lactobacillus paracasei

<400> SEQUENCE: 3

```
atgcccaaaa gggtcgatca acatatacgt tcacgcctta aaggctttac tttaattgaa      60
gtggtggtca gcctgatttt acttgcggcg gtcatgctgt tatggcgacc ggtttttattg    120 catgtcacgc ggttcacgct tcaagaccat gtgctaatca cgtcattgca agcagagcat    180
gacttgcaaa tgtttgtacg agataaaaag ttgcggtctg tggccttaat gtcggtaagg    240
gtgagaagtc ccgagaaagc ttacacgatc aattttatc agaccaaaca ttttcgcggt     300
atggttcgtg tgatgggatc tgaaaatggg catatgccat tatttacgca tctaaccggt    360
gtcaatttta gcaaggtagc tcaaggcttt cgctatcgtc tgtatttgac gacttcgcag    420
aagattgacg gtggggtgca aatcgatgaa gatacgcggt ag                        462
```

<210> SEQ ID NO 4
<211> LENGTH: 507
<212> TYPE: DNA
<213> ORGANISM: Lactobacillus casei and Lactobacillus paracasei

<400> SEQUENCE: 4

```
atggccgctg atttcaccca attacaacaa gccattcgct tgctcaatgc ccatactcga      60
gctgctgatg agcaagcgtg gcaagtgctt tttgatcgtg ggctggcaac tttatcctct    120
gaaactcgcc ggcaaatgca aacagttcgg tttaatcatg cccaattgac gttactcaca    180
```

```
acgctggatc aaagcagtcg caaacaactg cgcaatcagg atttaaccgc tgctgttccg    240
ttctcacaag gcctagtctc acgctatgtt gctcgccttg ttcaattaaa cttgctgaca    300
aaattatcct tgcccgacaa tcgcaaggcc tacattgttg cactaactcc gcttggtcaa    360
caagtcgctg ccttacatca gcaaatgcat catcacacaa atgctcaact cgcctctgta    420
cttcataccc ttgatccaca agatgttcaa actaccattc aggtactcac aaaactgacg    480
gctcagcctt tacatcccaa gtcttag                                        507

<210> SEQ ID NO 5
<211> LENGTH: 261
<212> TYPE: DNA
<213> ORGANISM: Lactobacillus casei and Lactobacillus paracasei

<400> SEQUENCE: 5
atgggcggtg tcatttgtta cgcggtgccg gtcttttgga aagaatact tcgcagacac      60 ctgattcacg agattaagac cctgaatcaa ggattgcagt tatcaagcaa agccatgagc    120
caattaattg atccggaaaa tccttatatg gtatttgctg atgaaaatgg tgaactggat    180
ttttcatttt tgtggctagg caacttgcgt caattgaggc gtgaactgcg tctaattaaa    240
gaacagaaag ctagggtttg a                                              261

<210> SEQ ID NO 6
<211> LENGTH: 1077
<212> TYPE: DNA
<213> ORGANISM: Lactobacillus paracasei

<400> SEQUENCE: 6
atgagtaaat ataaagttat tatttgggga ttaggaaacg ttggtcgttc cgcagtgaga     60
atgatcgcgg aaagacaaaa tatttttgaa ttggttgcag ccgttgacgt tgatccaaag   120
aagttaggta aggatgccgg agaagtcttt gattttgaca agtcggcgt caaagtttca   180 gatgatattg atgcagcctt gaaacttcca gctgacattg tgctcgactt ttgcccaacg    240
gaaatggaca acaaggaac attcatgcct tctgctattc gactcgccaa atcgctcgat    300
gccggtaaaa acgttattac cacgattccg gtatatcatg ttcaagacag tcagccagaa    360
gtatatgaat atctaaatga acatgctaaa gcacataatg ttgcttttgt accatttgga    420
cttttgccag gcgattatgc ctcatatatc ccactagttt tggccggggc catgggccac    480
gtggataaaa ttgttgttca atccggtgaa gatgactggc acaacacatc aggctgggtc    540
gatgtcttct catatggcgg cgatatcaat aaatatccaa aaccagactc agacgaagat    600
ctcttggcta agttcattta tgcttattat tcatccggcg tatacgagat ggccgatagg    660
atcggtctga aatatgatac cttcaaacca gagcatgaag tcttcactgc acccaaagat    720
ttggaaacga tcaagggtac agtcaaaaag gcagcatttt atgcccacag atttaccatg    780
gcactttaca acggcaacga acaagtagcc gccttaagat atgttcataa agttgataat    840
aaagagacac cagaattacc gatcaataat acgattcata ttgaaggctt gccgtcagtc    900
gatgcgcaga tcgatggatt gatcccagaa agagaaggct acgtttcatc agccgctcca    960
gcagtcaact tgatccctag cattctcgag accgacaaga caggttatgt tgaagtctgc   1020
gaccttccag tagtgattgc caggccattg gatattggcg caaaaaatt agtctag       1077

<210> SEQ ID NO 7
<211> LENGTH: 561
<212> TYPE: DNA
```

<213> ORGANISM: Lactobacillus paracasei

<400> SEQUENCE: 7

| | | | | | |
|---|---|---|---|---|---|
| atggcaacct | attcgcagat | agaactagac | ataatcaaat | catttaaagg | gctgatgaaa | 60
| gaccatgaat | tcactgagat | ctcaattaaa | atgatcgctg | aaaaagccga | tatcactcga | 120
| cgcggctttt | acaatcactt | cttagataaa | tatgatcttg | tcagtaccat | ctttgagcat | 180
| gatctttttc | caacagtcat | cagtttgacg | aatatcaatg | actgggatca | agggtcgctg | 240
| tttatcgtga | attatctcca | agacaatcgc | gactactata | aaaaattgtt | gtcgcttgaa | 300
| ggacaaaact | gtttacagac | agactttat | aaattgactg | agatgcagat | tgggatcttg | 360
| atcccagaaa | tattggtcgg | taggaaaatt | tctgacgaag | atcaggcatt | tttaagcgat | 420
| tattatttc | acgcttatat | gggactgact | accgaatggg | tcaaaggtaa | atatggtttt | 480
| tcaactcagg | agttcgttaa | acggtggaaa | gccttactca | ataattcaat | gcataattat | 540
| ctggacaact | acgctcgatg | a | | | | 561

<210> SEQ ID NO 8
<211> LENGTH: 1077
<212> TYPE: DNA
<213> ORGANISM: Lactobacillus paracasei

<400> SEQUENCE: 8

| | | | | | |
|---|---|---|---|---|---|
| atgagtaaat | ataaagttat | tatttgggga | ttaggaaacg | ttggtcgttc | cgcagtgaga | 60
| atgatcgcgg | aaagacaaaa | tatttttgaa | ttggttgcag | ccgttgacgt | tgatccaaag | 120
| aagttaggta | aggatgccgg | agaagtcttt | gattttgaca | aagtcggcgt | caaagtttca | 180
| gatgatattg | atgcagcctt | gaaacttcca | gctgacattg | tgctcgactt | tgcccaacg | 240
| gaaatggaca | acaaggaac | attcatgcct | tctgctattc | gactcgccaa | atcgctcgat | 300
| gccggtaaaa | acgttattac | cacgattccg | gtatatcatg | ttcaagacag | tcagccagaa | 360
| gtatatgaat | atctaaatga | acatgctaaa | gcacataatg | ttgcttttgt | accatttgga | 420
| cttttgccag | gcgattatgc | ctcatatatc | ccactagttt | tggccggggc | catgggccac | 480
| gtggataaaa | ttgttgttca | atccggtgaa | gatgactggc | acaacacatc | aggctgggtc | 540
| gatgtcttct | catatggcgg | cgatatcaat | aaatatccaa | aaccagactc | agacgaagat | 600
| ctcttggcta | agttcatta | tgcttattat | tcatccggcg | tatacgagat | ggccgatagg | 660
| atcggtctga | aatatgatac | cttcaaacca | gagcatgaag | tcttcactgc | acccaaagat | 720
| ttggaaacga | tcaagggtac | agtcaaaaag | ggcagcattt | atgcccacag | atttaccatg | 780
| gcactttaca | acggcaacga | acaagtagcc | gccttaagat | atgttcataa | agttgataat | 840
| aaagagacac | cagaattacc | gatcaataat | acgattcata | ttgaaggctt | gccgtcagtc | 900
| gatgcgcaga | tcgatggatt | gatcccagaa | agagaaggct | acgtttcatc | agccgctcca | 960
| gcagtcaact | tgatccctag | cattctcgag | accgacaaga | caggttatgt | tgaagtctgc | 1020
| gaccttccag | tagtgattgc | caggccattg | gatattggcg | caaaaaaatt | agtctag | 1077

<210> SEQ ID NO 9
<211> LENGTH: 429
<212> TYPE: DNA
<213> ORGANISM: Lactobacillus paracasei

<400> SEQUENCE: 9

| | | | | | |
|---|---|---|---|---|---|
| aaaaacggct | tagaacgctc | atatttgcgt | tctaagccgt | ttttatcagc | ataggttctt | 60
| gacaccaata | aacatcttta | gtaattgatc | aaatttaggc | aatgtgcttt | tgtcggtgaa | 120

```
tggcgatagc cctaccgaag cttcagctga ggttcttctg agccacgcaa gcgaagcgcg        180
ctagggcaag ccaacggcgc gcaggcgaag ccggagttaa atgtggcgca gccacacctt        240 tttaggagc aacgcgacca gaattttgta tggggtttgg gaagaggttc tccccaaggt         300
cttttgtggt tattaacaag caaaacacaa acacaagcct cgcgcgcgtt atatatactt        360
ctaaatactt ttaaatactt taagtactta gggagacgag aatggctcaa ccacgcgttt        420
aaatcgact                                                                429

<210> SEQ ID NO 10
<211> LENGTH: 241
<212> TYPE: DNA
<213> ORGANISM: Lactobacillus paracasei

<400> SEQUENCE: 10
acgacctctc gaccacccac tgcctcacca atccccaggt gaaccgggcc aagggcacta        60
ccgagcaacc cgaccctat atccggtgg gcgtggtgaa gcagaccgat gggggcatcg         120
tggtgcgggg cgcgcggatg ctctccacgc tgcccacggc ggatgagctt ttagtcttcc        180
ccagcacttt gctcaaagaa gggccgggag ccgacaagta cgccgtggcc ttcgccatcc        240
c                                                                        241

<210> SEQ ID NO 11
<211> LENGTH: 7384
<212> TYPE: DNA
<213> ORGANISM: Lactobacillus paracasei

<400> SEQUENCE: 11
attgatcgcc tccgggtcac ttatatgtaa ctaataatac tcccttctct ctttagttac        60
aatagggtac agcctatcga atcacttacg cttccacttt gagataactt ttcgttatta       120
tttatcaacg gcattaacga tatcattaac tgtttgcaat gcatcgctca gtacactaat       180
tggtgcttgt tcaatatact gcatgtgtcg ttgtacaaaa tcaaggtgt gaaattgtaa        240 cggattcacg taccctttcta ttttttcagt ctgaatcggt accatcaagc ctgtttcagc      300
taagcgatta tgtttggcat gcgtgatcgg acaaaccaac gctaatccag tcattttggc       360
atattgttga ttgctaataa cgagcgctgg tcgtcttttt tgaatttcat gaccccgact       420
tggcatgaaa tcaatactca caacatcacc tttgcgtggt tgataatgcc tagtcccact       480
cacttggtaa tacctcgttt tctaacgtaa tatcttgttg gtgtacttgt tgcttgtacc       540
aatcaccttc aaatggattg cggtgcttcg gcagataaag aatgccacca tcatcacgtt       600
gctcaactgt aaattcagtt ccatcggcga ttttaatact cttggaatg gttaatgtaa        660 tggaattgcc aacccttctt gctttaactg tcattgaaat catcctttcg tatacaccga       720
gtatacacca gcgcgaatga atctgcaact cttgtgccct cttgtgtaca aacaccactg       780
tcaatttact tttgcctatt gtgctttatc tcttctcgtt ctgtcattag tatgccacca       840
acacggccga cttcatccgg ctcacctttg atgacgcctt gaataccatc gatttgcttc       900 caagtctttta cttccaagtt cttcaaagac tttgatatcg ttttcgatg ccggcaaaca       960 cttcttcatt ctgatgcctt tcaaagaatt cctctagatc attcatcaga gattctcctc      1020
acttaaacct agttggcgtc aaattccatc tcagcaatcg aatcttctag gctgtccatt      1080
acttcgtatg tttcaatgaa gttaacccag ctgtcatatg gatgtagttt gctttcttta      1140
atgctagttc taagctttc gtacacgttg tcaataaact gctcaaccat cctattaacc       1200
```

```
gcactattaa taaccgcttc gttccactgc ttagatgctg cacgctttcg attttgacta    1260
tgctgatggg acagcgcccg gcttctgaac aacgctactg ccctgctgtt agcattcaga    1320
taggtttcaa attcttcacg atccattacg tttcctcctc aaaataagcc tcatttcata    1380
gcacagcttc agcaaaaggc atgtcatcct acatgccttt tttctgttgc tcttcaatat    1440
cagtataaaa cgtcctgccg ctttaggcaa acgtatgttc gctattaaga acatacgttt    1500
gtataataac tataaaagat ttaaaggagg tcaatcgtat ggaaaacaat gtcccgcgtg    1560
aaaaatggct ttaccctgac cgctgcatga agaaatggct gggctggatt ctaagcgacc    1620
attccgccta tatggaagaa gcggctatct cagaacaacc ggtgctccca aagcctgaac    1680
agacacaaga aaccattaat ggcgtactcg aagatgcttg gcaaaactca aaaattgtcg    1740
cagttcaaat cggtacgcca tacgatgatc ttctgttacc ggatattgaa ggcgccgtga    1800
ttggtcattg ggacgctcag gtttatctac agcttaaaac tggtgagatg caatccatta    1860
atgcagcgga cattcgcaat gtgcaactgc tcaatccaga tcggtggtgg gcgttagtat    1920
gacgacacca ttagatgatc caacaaggtt accggtacac gacattatgt gcattgactg    1980
taagtccttt tacgcctcag ttgaagctat cagacgcggg attcatccgt tagccgccga    2040
cattgctgtt ctcagcaaag gtaattctcc tggcggtttg gtgctggctg ctagtcccaa    2100
ctgcaaaaag cgttaccacg taggactgag tacacgccgt tttcagctaa gggacgatat    2160
gtaggtagaa cttgctgaac cgcggatggc taattacatt cgcaagaatt acggtatcaa    2220
tcgtatttac cgtcagttta ctgacgatgc tcactggtct ccctattccg ttgacgagtc    2280
ctttattgac gttacccacc cccacaatct cttcggttct aatgaagaaa ttgctaccca    2340
aatacagaag aaggtgtttg atcagtttgg cattgtcaca acagttggca ttgggcaaaa    2400 tccccctattg gcaaaattag ccctagataa cgaggctaag aagtcaacgc cttggcaagc    2460
cacttggact tacgatcgtg tgccagaaac aatatggaaa cttgatgact tggttgattt    2520
ttggtcgatt ggtaatcgaa ctgccaagaa gcttaacgcg attggccttc ataatctttta    2580 cgacttggct catgcagacc gcgccattct gcaccaaaga ttcggtgttc tcggtgatgc    2640
catgtacttt cacgcatggg gtattgatta ctcagactta acccgccgct acttaccacg    2700
ggccgaaaat aaaggctacg gcaatagtca ggtactcatg cgtgattaca ctcaggcaag    2760
ggagattgaa gtcatgctta gcgagattgc tgatcaagtg gctggccgaa ttcgccatca    2820
ccaagtccaa ggtgaggtca ttagcgttgg cattggttat gctgatgcag aagaagctgg    2880
cacctccggt ttcggtgcgc aaatgaagat tgatcccaca aatcgcacag acgatttaat    2940
tcgcgctact cgatttctct tccatagtaa gtggaacgga cacgctgtta gaaatgtctc    3000
agttcgcgtt aatcgcatca gccaagcaag tacaatgcaa cttagtctat ttgaatcagc    3060
agagaaggag gaagcaaacg cggctcctat gctgtaatta cggataaaag aatcaccatc    3120
attaggtttt tcgtctaaca attttaggaa acttcacttt ctaggtcgta actttatttt    3180
tgcaatctag ggttttttaa atatatacat tttagctcgt ttgtgtttaa tattataatc    3240
acaactatac caatgataaa tgtctaacat aaatatacaa acatgttgac agaagctctt    3300
gaatacgttt acaattattt cgttcaggcg agctttgttt ttgaaaaagt attaatacaa    3360
gataactagg ttagtggctg ttgaattagg cccccgattt cgggaccacg acagtcactt    3420
gatactcgat ttttatcgtt tgctggcttg atcgtacatt gaacgaaatt ggtacagaaa    3480
aaagagctaa gagccgctcc aaattagcca aaacgattgc ggcgtcaatg cttacggcga    3540
tcgtttctgc agttttagct gttaccagat caagtcctag tttcccttg atgaaggcaa    3600
```

```
actcacgctc gatctcacct cgtcgatttt cggcttgtcg gtctgcctta cgtttggccg    3660
gatcgacctg cttcggccga cggcccaatc taggaccgct aagtttgatc ccaagatctg    3720
cgcacagccc gatattcgcc cgagtccgat aaagcgtatc agccaagatc tcatccgggt    3780
atgtaccata cgtgtcaaaa taatggtcga tcgttgctgg taagtcagca ctttcgttaa    3840
acgcattgaa cgcaaaccgt tcaacggcca cgacgccatg actgatcgat acgtcgatct    3900
tgggcccgaa ttcgaccgga tcctttgctt tgccgcgaat gatcggtcgg atcgctggtt    3960
gatcaaggct tacgatccga tccgcgactc ggtgagtgtg ctgtcgatac atttcagttt    4020
gttgctcata caattttcga atgatcgtta atcgttgtgt ctgccgttga ttcaattgcc    4080
cgccttgtgc ttgcagttct ttgacgtaac gcaagtcacg tcggatgtac tgtaattgag    4140
ccttgatctg cttatgggtc gttttcaccc aacggcgggg tttacgtgaa aaggcggtcc    4200
acgtttggtg ggccttgcgc ttataggtac gcggcggttt gaccgctaat tgcttggcca    4260
tggctgcgat gaatcgctct aaattgagcc gcgcctgatt gagtagctgc gtatcctgcg    4320
gatacttgat ctttactggg accgcagtcg catcagtgat caagatcttc tgatggccaa    4380
gtttagcttg gaggcgatcg cggacaaaat cgctaatgat gttcgtgatc aactcggaaa    4440
gcggcgcgat ccggcgcctg aaataggaca gcaccgaaaa tgaaaacggt gcttgcggct    4500
gatactctgg caggccaata aaatactgat aagccggtgt atcgcggatc gctgcgacta    4560
actcacggtc cgatagctga gtgcgctgct tgatcagttg ggcgccataa agcagccgaa    4620
agggtttacc tgcccatcct aagttagacg ggaaagccaa ttggtacgcc tcttctagtt    4680
gcggccacgg aacttggtcg gccagttgga cccactcgtt atctggactt aatggggtgc    4740
ttaagccgct accaaacgat tgatcgata attgaacggc ttttcgacga taaaccatga    4800
tccatgcctc cgatagggtc gtgtcaaatg caaacgaaat gagcacgatc cgtaaattca    4860
tatgcattca ttatacgacg ataacgggtt caactcgcat caaatgtggt tatatcaaat    4920
tattcaacag ccactaggtt aagatcttca tttaagtgat attcatttgc aagcaattga    4980
aaattactca tcacgaagag gatttcattg gccatattgg atagcacgca aatcacttgc    5040
tttaagaaaa tcagttcctt taatgagtct cttaaaggac ggggctctca cttgtactca    5100
caatcaatgt taactggaga tcaacaatat ggtcatagat tcccataata acattgactt    5160
gactatctaa aagaggcttc taactttgat attggtgggg ttattggttg cttggctgta    5220
agcagataat cttaacttgg gttatttttca ttgtgttgta aagacatttg ttataaaggc    5280
cgaagttatc gctttgactt gtaataaatt attttttgatt gagatatcag aaaataaacg    5340
ggggataata atgaaaaaga ttattaggat tgttctttgt gttgttagtt gcgttagtat    5400
catggtcgga tcgcttgggt tctattcaac tccaaagatc gttaaagccg acagtacatc    5460
tgttacggat gtcgacatta tacctatat ttctagcatg acacttgatc aaaaaattgg    5520
acaaatgttt gtagcacgaa cctcacaaga tactgataaa gctcgtgctg atatagcaaa    5580
atataatctt ggcgggctga ttgtttatgg tgttgatttc actagtgtta aagggacaac    5640
agctacagaa gctcagaata acttcaagat gaagatgcaa ggctttcaaa actcggcaag    5700
tctgccacta ttgattggtg ttgatcaaga aggaggggca gtctcacgct tatcacaaaa    5760
tcctctaatt gccaacggca gaagttttcc ttcaccacaa atggcttatg ctaatggtgg    5820
aatgaccaat gtaacaaaag aagctagtga agtcggaact attctaaaaa atctgggcat    5880
taactggaac tatgcaccag ttgccgacag tacgcctgac acctctagtt ttatttatgg    5940
```

```
tagaaccttt ggtcaagatt acttggctac tgcaaactat attacgaatg tgatccctgc      6000
gtggcaaaat gctggcattg ccgcaactct caagcatttc cctggttatg gatccgcgat      6060
tgatacgcat acggattttg cagtcgttac aaagtctaag gaggattttg aaaagagga      6120 cttgcttccc tttaagtccg gtattacagc aggggcagat tctgtaatga ttgcacatat      6180
agtaatgcaa gctgttgacc cagtgtatcc agcatcatta tcacggaagg tcgttaccga      6240
tttgttgcgt aatgaacttg ggtataatgg cttaataatt accgatgcat ggaaatggg       6300 ggccatcaag caatttgctc aagaacatga tcaagttcct gttgatgttc ttgctgttga      6360
agcagggaat gattgcatca tgaataacga ttatgaaacc gctattccac agattcatgc      6420
agcagtaact aatggaacta ttaaggaatc agaaatcaat gaacacgttt ccgtattct       6480 tgatctcaaa cgcaaattag ggttgttaac taaaggacaa cttcagcaaa aaaagttca      6540 ggttgacaat gtttcctaca gcagtgacaa caaaaaggca actgtgagtg aacagttgt      6600 tgatagtgat tggcaagttg gagaaccatt atcggttaaa gactcgactg ggaaggtcat      6660
tattaccgca gacgttggtg ccggtggtaa gtttactttc gatgttccta ctaagtccca      6720
agaacaagta ttaactctga ctactaatt acccaacatc gctgattctc aaataactat       6780
taaggctgtg agttcatcga atactaacaa agctttgcta gaaaacttga tcaacgctgc      6840
tgaacagttg gatagtaatc aatatactgt caagtcgtgg gaagaattac aaactaaact      6900
aactgaatca aaatcgattc tgaacaatga tagtgctaca caagatcaag tagacgcttc      6960
cgttaatgct ctacaaattg cccttaagca attagttcct gtatcaaata gcggaaataa      7020
tggtcaaagc tctaatgata gcagtaacca aagttcatct agcagtagtg gcaaagaatc      7080
atccagcaat agcaatgcca atattactag taaggatcag tcagctaagg attcaaatac      7140
gaggcctaaa gaccatagtc ttttgccaag tacaggtgaa cgggtgatga cgggaatttc      7200
tgttctaggg gtaattttaa tagcttgtgt gactatatta tatattcgga aaaaggacg      7260 cagcttttaa ttagtctctg cgtcaactgg cgttaaaaac tagattgaag taataaagtt      7320
accacctgga aagaggcatg ctcattgctt gcaagggtgt cgacgtgtaa tagaaaagtt      7380
gggg                                                                    7384
```

<210> SEQ ID NO 12
<211> LENGTH: 1410
<212> TYPE: DNA
<213> ORGANISM: Lactobacillus paracasei

<400> SEQUENCE: 12

```
tggcgtgggc aacgtgcacg ttttctagtc gctaaactgt gaacaatgct cgtgctaaat        60
gcaaaactga gcaaggagat gaactataag cgggggaccc tttgctattg aggaggaagg       120
cgaagtagag aaagagcggt gatttgaact cgaaacagcg gcgccgcagg ctagcagcac       180
tgttagatta atcgccagca gcagatacta gacagcttct taaaggcttg ataatagcgt       240
tgcgccattt caatggaact agtggtcaaa atcgcattgt agttgccatg acccaaactc       300
gttttacgcg ggccttttg taaaatatat tgaacaactt ggttaatatg ttcatcggtc        360
tcaaagtcag ccggagttaa atacgtttct tccaagtcct tcactgacat cgcttgaatc      420
ttggcttgaa ttttcgcttc atcagccgta ctcagcaggc ggccttgctt atcacgacga      480
gctttaacgc gctgagtttc ttttcaagg gcccgggtta ttaaagcgtc tttaccaatc      540
gttgtcacgt gttccacatt aaatggtaac actgcttggt cctctaaggc gtctcgcaag      600
ttataaacat gacagacttt accaaatagc tcctccgtcg taactgctag atcacctttg      660
```

```
agctgtttct tatttttcatt aaaaatgggg gtgccagtgt aaccatacca gttactattg      720
ataaacgctg ctcgaatttc cttttgcatc ttaccaaact gcgaccggtg gacttcttca      780
acaaagaaga tcacccgttg cttttaaagtc ttactaaagc gggattgctt accggttgcc      840
agctggactt gcgtttttt gaccgcccga tggagctttt gaatcgaggt gaccaagacc       900
ttaccgtcat tttgttgcaa tttacgcatt aaatcaccgg tgttttgggc ttcgttaatg      960
gcaatatcat cattggcagc ataggcacta aagttgctgg ttgtctgttc gtctaaatcc     1020
cgccggtcaa ctaagaagat gaccttatcg acaccaggat cttgcgcagc taatttagcg     1080
gttttatatg aggtgagtgt tttaccagaa cccgtgtat gccaaacgaa accatcctga      1140
tggtcatgaa tccggtgcat cacggcttca atcgcataaa tctggtaagg ccgtaagaga     1200
attaagcttt gccgctcttg gtcgatgact gtatattcac tgaccatttt gtgggccatg     1260
ggaatattaa ggacttggcg cgtgaacgct aacccgtttt ccacggggtg attatcccgc     1320
gtccgccaat tgaacaaaaa ggctttattg aaatgatccg gttcggcatt cgcaaaatac     1380
gccgtactat ccggcgtcat aatcacaaac                                      1410

<210> SEQ ID NO 13
<211> LENGTH: 592
<212> TYPE: DNA
<213> ORGANISM: Lactobacillus paracasei

<400> SEQUENCE: 13
cgatctaaaa gctaagttat ttccaagat atcaaacaac ttcttaaccc aagaatcttc        60
cacacatagg acaataatga atccaaatag attcagcttt ttcctgcaaa ccgggatcag      120
tataaacgtc cagtaccgga taatcacgca ttaagttcag ctgccaatgg gtatcatcta      180
aattaaaaag atccgattta gtgtctcccc ttactacatt atggcaatac acacaactgt      240
tgttatacat gcttccttgc tttttgattt taaactcctc cattttgcat attataagaa      300
gattacttct acttgatata tagatgcttt ccttgcgagg gtaagtcaga caaggaagca      360
tttctaactt gagatactta agcttgtctc aatagatgta gatagcggct ccccaatcgg      420
atattaacag ctcaactagt caaaccagat atataaatgt gacacaagct ggaatatata      480
tcattatcta gataattcaa attgagctaa taaaatcaat aaagaaaatt ttaaataaca      540
ttattttata aaccccttta ggattttccc gatttgatat tctacgtatg tt             592

<210> SEQ ID NO 14
<211> LENGTH: 2233
<212> TYPE: DNA
<213> ORGANISM: Lactobacillus paracasei

<400> SEQUENCE: 14
gagtatccaa aaatacgacg ggtatttgaa taggatactt attaagcgag aatggtattg        60
gaaatctgtg gcagccactc agcggaacca taccttttatc ccaaccccac gcaaaaaaaa     120
catcaagtaa tccgtcagat atgatgactt aattgtggga cagttctaat atgaagaaaa      180
caggttagat aattggggtg aaaagatggc aacctattcg cagatagaac tagacataat      240
caaatcattt aaagggctga tgaaagacca tgaattcact gagatctcaa ttaaaatgat      300
cgctgaaaaa gccgatatca ctcgacgcgg cttttacaat cacttcttag ataaatatga      360
tcttgtcagt accatctttg agcatgatct ttttccaaca gtcatcagtt tgacgaatat      420
caatgactgg gatcaagggt cgctgtttat cgtgaattat ctccaagaca atcgcgacta      480
```

```
ctataaaaaa ttgttgtcgc ttgaaggaca aaactgttta cagacagact tttataaatt      540
gactgagatg cagattggga tcttgatccc agaaatattg gtcggtagga aaatttctga      600
cgaagatcag gcattttta gcgattatta ttttcacgct tatatgggac tgactaccga       660
atgggtcaaa ggtaaatatg ttttttcaac tcaggagttc gttaaacggt ggaaagcctt      720
actcaataat tcaatgcata attatctgga caactacgct cgatgaatta cacagattgg     780
attaaatgag aaagatgtta catttgtgcc aatatgtgaa ttgataaata tttcacaagg     840
aactattctt tccctgtaaa cgaaagttga cttgaaagga gttagttctg atgagtaaat     900
ataaagttat tatttgggga ttaggaaacg ttggtcgttc cgcagtgaga atgatcgcgg     960
aaagacaaaa tattttgaa ttggttgcag ccgttgacgt tgatccaaag aagttaggta    1020
aggatgccgg agaagtcttt gattttgaca agtcggcgt caaagtttca gatgatattg     1080
atgcagcctt gaaacttcca gctgacattg tgctcgactt tgcccaacg gaaatggaca    1140 aacaaggaac attcatgcct tctgctattc gactcgccaa atcgctcgat gccggtaaaa    1200
acgttattac cacgattccg gtatatcatg ttcaagacga tcagccagaa gtatatgaat    1260
atctaaatga acatgctaaa gcacataatg ttgcttttgt accatttgga cttttgccag    1320
gcgattatgc ctcatatatc ccactagttt tggccggggc catgggccac gtggataaaa    1380
ttgttgttca atccggtgaa gatgactggc acaacacatc aggctgggtc gatgtcttct    1440
catatggcgg cgatatcaat aaatatccaa accagactc agacgaagat ctcttggcta     1500
agttcattta tgcttattat tcatccggcg tatacgagat ggccgatagg atcggtctga    1560
aatatgatac cttcaaacca gagcatgaag tcttcactgc acccaaagat ttggaaacga    1620
tcaagggtac agtcaaaaag ggcagcattt atgcccacag atttaccatg cactttaca    1680 acggcaacga acaagtagcc gccttaagat atgttcataa agttgataat aaagagacac    1740
cagaattacc gatcaataat acgattcata ttgaaggctt gccgtcagtc gatgcgcaga    1800
tcgatggatt gatcccagaa agagaaggct acgtttcatc agccgctcca gcagtcaact    1860
tgatccctag cattctcgag accgacaaga caggttatgt tgaagtctgc gaccttccag    1920
tagtgattgc caggccattg gatattggcg caaaaaaatt agtctagact aggctttcga    1980
agctgctttg accattaagg ttggagtagc tttttcattt gcaagtaaat cattacggct    2040
tgtgtatacg gtatacaaaa tggagaaaac gctgactagt ttataaatca ttgagactta    2100
acggccggat aaatgctgat ctgattatag aaataacaac aaaaaggcca cgctaaaaat    2160
catattaatt ataatcggga aatttattaa taatattcaa gaaaaataaa aaccgtgggt    2220
acattattta aaa                                                      2233

<210> SEQ ID NO 15
<211> LENGTH: 5866
<212> TYPE: DNA
<213> ORGANISM: Lactobacillus paracasei

<400> SEQUENCE: 15
tttgaaacta agacgaaagc tgccatgtca aacaaagccg ccataaatgc cactgtcaca      60
gatccatcag ccgcaatgcc agcatcttgc tgaagttctt taacagcatt aagggtgtta     120
ttcgtgaact cattattaaa gtctactgga ctaatccctt tgcaccagaa agcccccttga    180 atgagttgag caatgttccc cttatatcct ggcttcagac tacctacaac aggtgctaag     240 gcgttttgg tcgtctcgcc aaagccttca ccaatagcac taataccgat tcgtgctgt       300 aatcccattc ttaggctata aattgttggc catcccgttt gcccgttttc tggagctgcg    360
```

```
acaaagccag gaacgctacc atacgttttg ttgagccatt tttgaacggc tcgtactgct      420
tcatctgcca ttttaaagtc tccttttttg ttttagacag cacgtctgcc gtcacaaaaa      480
gcaaacatat gttcggattc atttcatctc ttcaaagctt cgaaaggcaa ccctgatcca      540
caaataatcc ttttattttg aacttagcaa aaaaatgagg ccctcacata gtgttgaagt      600
tgcctcattc ttaatgtcta tatttaaagt attgccacaa cgatggatca tcgaacgctc      660
atggacttgg ttagacatgt atcgacgact atgaaaatgt gggcgcaagc tcaatttcac      720
cttccaaatg tttgtgctat ctcatttagc gctggttttt ttaggataga ctagacaagg      780
actaataatt tctcaagaat cccgcaactc cactattcat tcgtcgaaat ccccactgat      840
actcttgtcc ttgcacgttc gaccaagcaa gaatgtttat tccgataacc gaattgttgc      900
catcaagtaa tggacctccc gacatgccat gatacgaatt aatttgttgt gaaatatata      960
ttcctagtgg gtcctctgaa aagggtgtga cagtcccact tgattgaacc atgactcctt     1020
gaagttcgta ccctgattgc ggatcgccag ggaatccaat ggatcttgct gccatcgtat     1080
cagcagggtt cgtatttaaa ttaagacccg caggcatact accagacttc atagagacaa     1140
ttgcagcccc gtaatcattc gaagtagctg ttgaattatt aatccatgcc tgtggcacta     1200
tcaatctatt caatactccg taaccgaccc cttgatgatt tgcttgacta tcaccaaagt     1260
taataattcc tccagaaata taatgaccat catataacat gtgtgctgct gtccctatac     1320
ggtctactcc aatgctaaat ccagtaccgc cagaagttcc actgctcagc tctgtgccat     1380
ttgagttaga gatgattttt ttatacgaac tgtcaaggta tggtgagtta atgaccatga     1440
caccatttgc catcgaaaac cacgtgctca aaaccccaac ggaactgtac ggcgccgaat     1500
tggggtttga cacaggtgat accgtcctca cagatagatg attagacgat ttattcagtt     1560
tcgcaagata ttcggacgta attccttgaa ctttcttttc ttcttttaaa tcctgatatt     1620
gatcaggtgt ataagctttg cacactccctt taaaatcggg ataagaatac tgatattgtc     1680
gaatgatttc attcaaaaac tgttgtgttg tcgtctggtt agtcaaaaca atatcattct     1740
ttggtaaaac atggctattc gctgccaaag gatttgccat actatcagca cttacactta     1800
ccgtttgaac ttgaattatc gctaaggctg cagctatcat agtgatatat gcccatactt     1860
ttcgcaattt aattccccct ttttcttaaa atgaaaccgc attcacggag gcttgtcaat     1920
gcttttaaaa aacaaacgtt acttttggct catcttggct gtcagcataa ttggagtaat     1980
tgttcttgcg gtgttatggc gcatgaaccc tgaaggaacg gcctcaaata agtttgaacg     2040
tcccaccatt actattaaaa aagtcaaact tattaagcac agtaacagta ttgctgtcac     2100
atttgctacc tctccaaaaa gcaaatatac gataagtgat cttaaagaga atcaactttc     2160
ttctggcatt tcgaataaaa gagaaaatac cgtttcggaa ttaaagccct cctcctctaa     2220
gcttgcaata cgggttaagc ataacaataa tatacaaacc aaagtggttt ctgttcccat     2280
tggttatcat attatgaaaa gtgccatttc aagaaagcca attcctatgg gagaagagtt     2340
taagtacaat ggaaagtcgc atgttttatt tagcatgacc attaccccta aaaaacaaaa     2400
caagaacagt ataaaaaaca ccactgcttt taacataacg gttaaaaatg atcactacct     2460
tgtccctgtc gtattagata ccaaatacct tactgtttct gattcagaag gtaactcatt     2520
aaaagtaaag ccattctcaa aaatttctat tccagcaaaa aagaaaaaga ccattgcaat     2580
aactattgag ggcgttcccg caagctctgc caatggtcta gttataacgt ataatactgt     2640
cgatttagac ttaccaatct cctttataaa ttcctgaaat tacactaact gtcccccacc     2700
```

```
ttgacagtca gtacactcaa actgtctctt atgcttacaa acacgtaatt taggcggttt    2760
ttaagcaaaa gtcgttagtt ttcataaatg ttatcttata ctctaatgag atctagcttg    2820
tgataataag gctgtttttc tttgacagcc ttattaagca cactaatcaa tgtcaattcg    2880 aagttttttgg tttcctactt ggccaacttt gttatcagaa attccaaaac tcattgcctc    2940
ccgccaccat atatttatcg agccattttg aaaatgaaaa atcgaaatat cggtctgctt    3000
ctattccggg atgagttaga tatgattttc ctaaccgata cttctctata tcaatataca    3060
tatctccgac atcccttata tggagaatgg gtactttatt tacaaaactt ttaggcagtg    3120
cctctttttc tttaatcatt tttctaattg aatagacttc acacgtatat cccataggaa    3180
tcccttcgat tgttgtgtca aataaaaata gtccattagt aatcgagaga aactcaatgt    3240
aatcctgtgg aaggttccac cttttttattt tttctatatc atcagcgtgt gcaggaggtt    3300
ctatcttaaa agaaacattt tgcacatctc catctaattg gaatgttgag agcgcttttt    3360
ccccattttt cgtcaccttt attaaagaat taattcttcg ccgaattaga gattccaaat    3420
gagttcctcc tcaatagttg ttaaaccacg cggtgatcaa ccgatgattt ggtgttaaca    3480
ccggcatcaa attattaaag tcatttgttc cgccataaac tctcgggcga atatgatgca    3540
cttctcgaga actccaaaaa tctgcagatt gattgccata tgtttcactg aacgttttaa    3600
tataaatata tctatctttt gatgaccaac taggagattt tgataactta gtccaggtag    3660
tattaatagg tgtttctgca tcttttttag acacgggatc aacatattca gggaaattct    3720
gtcctatttt attttgtaaa tagatggccg ttggtgggat tggttttaca ttagccgctc    3780
cattaactcc tataaatcca acagcgccag caacgttaaa aaatgtggtt ttggctggca    3840
attctgtaaa accaagtaat cctgtttgca aaccgcctat tttgctaatg ggtgccagcg    3900
tattggcatt caccggacct gcaagggtag gctcagtatt aaattcaatt tgcacatcaa    3960
ctgcggctgg cgggacaccc tcaatagaat caatccagaa attgactctg aattttccgg    4020
atatgtattc ttccgataag tgccaggtaa tatttgtaac aggaacttct gcacgagaac    4080
ttatgccatt gccatgacta ttattcagta ccacttgttt tccagaagcg ataattggtt    4140
gtccattttc tggattactt cttgataact tgtcagcatt ggtcagttga gtattgttat    4200
cgctaatacg gctttcagtt gaaacaattt gatttaaaga ttgtgttgtg tctgcggata    4260
caattgttga atcccaagc aaattgacta gaaagagccc gaatattagc ccaataactt    4320
tccacttttt cacgcctatt atcttctttc caaagttctt cagtgcctgg caataactgt    4380
atacattgag cagtatagtc gctatttttat agctgaacaa ctcataaagc tcaattatta    4440
ttagcctata aaaccactgc ctaagtgaat tgatctagaa cgaagcacgc cgaagaagtc    4500
gctaaatgtg ctaagaaaaa tgtgcttgaa tagctcaaaa gtaattagcg tctccattga    4560
aaatccgtta ttttttaagtg atctagtgtt aactatgaat cccaaataaa aagcaaaatc    4620
cgtaaatgcc aaattttcct ttttgacgtt tttctactgt cgcgagattt gcaagtgtac    4680
gtacacttac gatgaattga cagaatctca gctgcgctga tcgtcaattt tgtttggggg    4740
cacgccccca atccccctgt tatttgaag ggaggtgagt ccccccttcaa aatcaaaatt    4800 taaacagcat ctgccgccat cttttcgctg accttctcac gatgttacac gtggtgttga    4860
cacccacttg catttagagt ttcattcaag ttgaacattg tgtaatatat gagttgcatt    4920
tgataaacat atcagttgct atttgtgcaa ctttaaagct tcggctaatt caacgttctg    4980
ttaatttaca agcatctcga cagtttctgt taaagcaaca tctacgcttc aattcgagca    5040
actcactata cgtatgccga gttgcagaca agctactata tagctgtacg cgctgaaaca    5100
```

```
ccaaaaatcg ttcgtttatg cccaataagc gaataatctt gctcaggtgt agtaaaaaac    5160
tgtttacgtg tagtgaatgg cgctagccct tgtcgtaact ggcatcatcc acgtgtagta    5220
aaacgcgttt tactacacgt tcgtaatttt ttcacgtgga gtaaatggcg ttttactaca    5280
ccttttgacc ccaacgtgct atcacgacaa accaaaccgc actgcggttt accccaattt    5340
tggggtcagt tttgccttat gctctttcat gattttaggc gcgttccaag cagtctcaaa    5400
aagtggtcga tccaggcgag ccgattttg agaaggattg gatagcaact caatttattt    5460
tgatcttttg cttggagaaa acgttcacg ttttgaccag ggccgtcgca actgttgacc    5520
aaaactcgtc cggtaacgtg acgctattta acgccgcgt tggtttgcta gacgaccatt    5580
catcatcacc attcaggagg tttttgaaat gacaaagcaa gacgaaacac accgggtcat    5640
gttcactttg accgatcagg cgattgcaaa attgaatcag ctggtcgcaa aaagcaaca    5700 ggaagtgaat caaaatccgg aactggctaa gtaccatgtc agcgtgacca atcaaatat    5760 cattgaggac tggttatcaa agcagtgagt taaaaagcg ctaaagggcc tgtactagcg    5820
tttcttactc tggtgggtat aattaatgct ctctacatca aaaacg                   5866
```

<210> SEQ ID NO 16  
<211> LENGTH: 11007  
<212> TYPE: DNA  
<213> ORGANISM: Lactobacillus paracasei

<400> SEQUENCE: 16

```
gccacgaacc tgtagccgtt tggatgaagc catataatac tggaccaacc gccgcaaata      60
agtagccgac actttgagca aaatcaggaa tactaatcta ctttgccctt aaaaaatctt     120
gagatgatcc atatcttgtt ttgccttcat tactgtagtt ggtcataaga agtgccctac     180
attcattaga ttacttgtct aataattgta gggcacttgg gttgagaaaa atgatgttaa     240
ctaagaatgc aaacgaacta aaatctttgc ttgcttttta tccttttcta aggattcaat     300
tccttctgaa actaattcat ttaattcaat ctttttttgta atgacctgtt tgaatagtga     360
acgatgggta tctataatct taattactcg atcgaagata ttggcatatc cataagatgt     420 taataaaacta ccacctttt taagaagagc tctaacatct acaactggtg gatgttgaaa     480
taatgcaatc acggtaaacct tgccaccatt tttaagagcc tgaatggcac cagtaagtgt     540
gggttgtaca ccggcgcaat caaacgcaat atccactccc tgatttttccg tgatagtgct     600 gatagcgtga gctaatgact tttgactatc agcacgtatt gggtattgaa ttcctaattc     660
atttgctaaa ttcaaacgtt cctctgacat gtcatttatt atgacgtgat gtgcaccaga     720
aatttgtgct attaaggccg tgaacaatcc aattggacca gcaccttgaa ttaaaacatc     780
atctccagga gacactcggc ttgccataac tgcctgtgca gcaactgaaa ctggttcaac     840
taaggcccct aaatcaagcg gaaagctagc tggtaagaga tgtgcaaagg tactttttac     900
attgcacttt tcagctaagc caccgttagc cgaaaatcct aagaatcctg ctgattgatc     960
actacctata gcatgttcac accaattata atgaccagaa agacattccg gacattttcc    1020
acaagcaatc attggttcga ctgcaacttt atctccaatt cttaatttag atacttgttt    1080 tccaattttta gaaatcgtcc cagaaaattc atgaccagga attagcgggg cttgcatatg    1140
ggttagcgga tgaggtattg tcgccaaatc catacctct aaatattcat gaatgtcact    1200
accgcaaata ccattaaatg caacctcaat ttgaacttca tctggtgcgg atcaggaat    1260 atttctttt tcaaagcgga tatccttagg accgtaaata acagctgcct tcaccatagt    1320
```

```
catagtgctt cgcttccttc atgttcaata tagcacaatc gtatataaaa tagtgaatag    1380
atttcagtaa tgaagttacc atcttgactt aacaaaaact tgctaactga ttatatgaga    1440
aacttttact tgaaacattt ttggtgatta ccattaattc cctcggacat attttgaaaa    1500
accctatttg atgctgattg caaattattt tatgcgtatt tattaagggt ttctatgttg    1560
aagtatatag caaacttgtt caagtaactg actttcacgt gggctttagc caagagatgc    1620
tgagcagcga acccaagggg tgttactcgc ccacgcaaaa aagaaatcca attgcattcc    1680
agtatgagcg agaagcaagc cattaagacg ctgattcatg aactcgcgca cagtgaatta    1740
cattgtgatc cgaagttaaa attggatcgt tcaaccatgg aattggaagc tgaaagtacc    1800
gcgtttatcg tttgtcaaca tttgggaatt gacacgagtg attatacgtt tccttacctt    1860
gctgtttggt cgaaagataa ggatctttcc cagctctcca aaagcttaac gcgtatccaa    1920
tccaccgtcg aaaaattcaa taaaaccgtc gatcaaaacc ttgaaaagat tcgtgagaaa    1980
ccgttgacgc ttgatcaaaa aatagaacgc gctaaaacca ttgcgacaac ggaaaacatc    2040
gcaaaaaaag agcaagggct ggtgcaagca acgcaggaga aaacacgcta acccatttgt    2100
tgaatactct cactcaagag gacactccag cccttgatca cccaagaaag gaattaccaa    2160
catgaaaacc attgacgaaa tgaacgaatt cgatcgtgac attatcttac ttcaccgcaa    2220
gtctgtgagc gaagatacac cgcaggcaat tcttgtgaaa gtgaaacaga ttcgtaacgc    2280
aattgccgac gaaaaggcgg gtaaagaaga tccaattgag aaagaattta cactcgaatg    2340
ttacgacgaa gcaatcagaa aactaaggga ccttttcggtc gctgattatc agttgtggtt    2400
gcgtcaaaac aaagacctgg aagggtttga atttttgattt tgaagggtgt cgtagacccc    2460
ttcaaaataa cgggggattg ggggcgtgcc cccaaaacaa aattgactat cagcggagct    2520
gatattggat caatttatcg caagtggacg tccacttgca aatctcgcga cagtagaaaa    2580
agccccagaa aagcaaatct gaaaaaatgt aacaggcact tgatatcaag tgccttattg    2640
tttctaggat cgctaaaaat aacaggaggt ggttacatga agcaatctga tgaacaccgc    2700
acgcgttcag tgagaagcac tgtgcgtatg accccagagg agcgtgcttg ggttgatatg    2760
agaagagcct ctgtcggcaa tccaaagttc aatgcatttg cctgtcgcgc actcacgacg    2820
agcaagatcg ttcatgtaca ttttactgat actaaaaagt tacttagaca gctgtcaaga    2880
attgggaata aggctcctat gctgtaatta cggacaaaaa tagtttgtgc gataattaca    2940
gcataagggc ctctaggtcg agcccagga ggcggagacc gccgcacagc ccaaccccac    3000
gccgaaccgg aggccagccc gcccgcaccg cggccgcaat catccaccca acgcccccca    3060
agttttgat agcggtaaca acgcctgtgc gcttgtcgtg gccggccttt tttcataagg    3120
ttggaggaga aaggaagggt ggttatgggc gcttggtatg aacacgcaat tatttaccaa    3180
atctatccaa aatcgtttca agacagcaac ggcgacggca tcggggacct gaacgggatc    3240
cggcaacgga tcccgtacct gcaagccctc ggcatcaaca cggtgtggct gaacccgatc    3300
ttcgtctccc cacaggtgga taacggctac gatgttgcca attacttcgc cgtggacgaa    3360
accatgggta cgatggccga cctggaggcg ctgatcgcgg ctctgcacgc ggccggcatc    3420
cgtctgatca tggactttgt gctaaaccac acctcggatc agcacccgtg gttccaggac    3480
gccattcacg ccaaaaatag tctgtaccgc gactactaca ttttctctgg ccacgacggg    3540
cagctgccaa acaactgggg cagcttcttc ggcggatcgg tttgggcgcc ggatccggcg    3600
ggaaccgggc agtcgtattt tcatctgttc gaccggcgga tgccggatct gaactgggcc    3660
aatcccgagg tgcggcgggc gatgggagac gtcgccacgt tctggctcgg caagggcatc    3720
```

```
gacggactgc ggctggatgc cttcatccac attgccaagg ccgatctggg gcaggattac    3780
cccctggctc cggggcagca gacgccggtg gtggcggagc cgttttctc caacctcccg     3840 aaggtgcagg aatggctgcg gccgttctgc gaccggatca aaaccgacta ccccgacgcg    3900
tttctgctcg gcgaggcggc atcggccaac gttaacctgg cggcggatta caccgcgcct    3960
agccagcacc tgatggacag cgtgatcacg ttccgctact tcaccgagga cgaaagcggc    4020
ctggatccgc ggctgccggc gcagtaccag ccgcggacgc tggatttccc ggcgttcaag    4080
caaacccagg cggtgtggca gcagaccctc gccggggtgt cgatgccgac gctgtactgg    4140
ggcaaccacg acatggcccg gctggcgacg cgggtggcca aaaccaccac ccaggcgcgc    4200
agtctggcca tgctgatgta cctgcagcgc ggcctgccgg tgatctacta tggcgaggag    4260
ctcgggctac acaacctgca gttcgatcac gttgatcagt tgcggacgt ttcggtggcg     4320 ccgttcgtgg ccgcggtcga ggccaccggg cagtcgcgga gcgggcgct ggccatggtg     4380 tcggcgacgc acaaactgcc ggcacggggg ccgatgcctt ggacgaccgg ttgcaccag     4440 ggcttttcca atcacctgcc gtggctggtt gggcgcagcg aggacgtgac cagcgtggcc    4500
gcgcagcagg ccgatgaggc cagcatgctg cacttctacc aagcgctgat tgccctgaag    4560
aagcagccgc tgtttcaggc cgggcattac cggctgctga cgacggcgcc gaacctgtac    4620
gtctacgaac gcacgctggc cagccggcgg ccctggtgg cggtggcctt ggatgagcaa     4680
ggcgccacct tcaccgtgcc tgaaggcctg acgaccgtgg cgctggccgc cggcgattac    4740
caactcgaag gtcaaacgct cacgcttggc gcgaacgccg cgtggtgtt aaacgaaagg    4800 ggaactcgat aaccatgcaa cttgcagcat tacggcaccg cccagaaagc gaagattgtt    4860
ttttgtacac tccagatgag ctgccggctgc ggctccacac agccaaggcc gacgtgcagg   4920
cggtcatcgt actgtacggg gatccgtatg tcaccgcgcc gaacccgacc accggagaac    4980
cggaattcgc ctaccaagag gcggcgatga tcaaaaccgg caccggccaa accagcgact    5040
actggaccat cagcctgacc gcgccttatc accgcctgca gtaccagttc ctggtgaccg    5100
gtcaggacgg caacaccgtc ctgctcggcg accgcggctt gcgggccgac agcgccgcca    5160
accgccgggc cgatctgttc cgggtgccgt acttccacgc catcgacacg gtacagacgc    5220
cggcctgggt caaggaaacc gtgtggtacc agatattccc ggaacgcttc gccaacgggg    5280
acaagacgaa cgaccccaag ggcaccaagc cttggcgtcc ggcggatcac ccgggccgtg    5340
aggattacta cggtggcgac ttgcaagggg tgctggacca cctggacgac ctgcaggcgc    5400
tcggcgtgaa cgggctgtac ttctgcccgg tgttcacggc gatgtcgaat cacaagtacg    5460
acaccatcga ctacttcaac atcgaccctg cgtttggcga caaggccttg ttcgccgatc    5520
tggtcaacca agcgcaccgc cgcggcatgc gggtgatgct ggacgctgtg ttcaaccaca    5580
tgggcagccg cagcatgcag tggcaagacg tgctgaagtt cggtccgcag tcgcgcttcg    5640
cctcctggtt ccacatcaac cgttttccgg cggcgccctt cgccgcgccg aacagggcg     5700 gcgtgccgca gtacgacacc ttcgccttcg aaccgcacat gccgaagctc gacaccagca    5760 acccggcgt gcaggactac ctgcttgagg tggcgacgta ctggatcaaa cagttcgaca     5820
tcgacgcctg gcgctggat gtggccaacg aggtggacca tcacttctgg aaacggttca     5880
atcaggcaac caaagcgctc aagcccgatt tcttcgtgct gggcgaggtc tggcactcca    5940
gccagccgtg gcttaacggg gatgagttcg atggggtcat gaactacgcg ttcaccgagc    6000
agatcgaggc ccacttcctg accggcaagc tgagtgctcc tgagctgacg gcggcgctga    6060
```

```
cggatcagct gatgctgtac cgcgaccaaa ccgaccaggc gatgctgaac atgctggact    6120
cgcatgacac cgcgcggctg ctaacggtgg ccggcggcga cgaggacctg gccctgcagg    6180
cgctggcctt caccttcctg caaaccggga tgccgtgcct gtactatggc acggaaatgg    6240
gcatggccgg agaaaacgat cccgactgcc ggcggccaat ggactgggcc cagctgaagg    6300
gcccgatttg gcagcgtgtg caggcccttg tgaccttccg ccgcgcccag tcggcaacgc    6360
taggcaccgg caccaggcg ctgagcgtga ccgcagccgg gctgcttaag gtaacccgca    6420
caggtgagca caccgtgacg gcgtatttta acaccaccaa gcagatggcg acactgaccg    6480
tcagtccatt actggcgcag ggttacgccg ccagcggct ggcgccaacc gggtttgctg    6540
ttatggttca gtaagattat gttagcgta acaggcaatt tgacctttta aaagcgtttt    6600
catattatca taatcaaaag tgtagaaaag ttcaggtggc gcaattcacc tcccgaaagt    6660
gaaggatgca agatgaaacg gatatttgaa atcgacccgt ggctggtgca aagccaccaa    6720
ttgaacccca cgagaaacg cctgcaggaa agcatgaccg ccatcggcaa cggctacatg    6780
ggtctgcgcg gtaacttcga agaaggttac agcggtgatc acctgcaagg cacgtacctc    6840
ggcggcgtct ggttcccaga taaaaccgtc gtcggttggt ggaaaaacgg ctacccggat    6900
tacttcggca aggcgatcaa cgcgccgagc ttcatcggca tggcgctcac cgtgaacggc    6960
gagcgcgtcg atctggccac cagcgtctac cgcgatttca ccctcacgct tgacctgcac    7020
cagggcctgc tgacccggag cttcgtgttc gagggcaaaa aggccacggt gcgcttcacc    7080
ttcaagcgtt ccctcagcaa cgtaatcaag gaggcggcgc tggtgcagct caccgccgaa    7140
agccttgtcg gaccggccga gctgacggtg gccgcacagc tcgacggcaa cgtcacgaac    7200
gaggacagca actacgacga gcgcttctgg gcaccgcagg gggaaaacgc cgcggcaggc    7260
accatccagc tgcagaccaa gcccaacccg ttcggggtcc cgcagttcac ggtgctgctc    7320
aagcaaagcc tgcgccaagg ggcaacccctt ttacccggca ccgtgaccac cagcaccggc    7380
cagctgacca gcacggtcac gctgccgctg gcgccaaacg tgccggtcca gctgaaaaag    7440
gacgtcatcg tggtcacgag ccgcgacgtc gcccctgagg cccaggccga agcggccgcg    7500
gagctgatga cacagctgca gggccaaagc tttgcggccc agctggcggc acacaccgcc    7560
ctgtgggcca agcgctgggc ccaaagcgac gtggtgattg aaggcgacga cgcggcccag    7620
caggggatcc gcttcaacct cgcccagctg ttcatgacct attacggcga cgataagcgg    7680
ctcaacgtgg ggccgaaggg tttcaccggc gagaagtacg gcggggcgac ctactgggac    7740
accgaggcgt acgtggtgcc gatgtacgtc gccgccaccc ctccggccgt gacccgggca    7800
ctgctgcagt accggcacga ccagctgccc ggcgcctacc acaacgccca gcagcagggg    7860
ctcaaagggg ccttgttccc gatggtgacc ttcaacggca tcgagtgcca caatgaatgg    7920
gaaatcacct tcgaggagct gcaccgtaac gcagcggtcg ccttcgcgat ttaccagtac    7980
acggcctaca ccggcgatga agctacgtc aaccacgacg gcatggaggt gctggtgggc    8040
atcagccgct tctgggcgga ccgggtccac ttctccaagc gcgccggcaa gtacatgatc    8100
cacggcgtca ccgggccgaa cgagtacgaa acaacgtca caacaactg gtacaccaac    8160 acgatggccg cctggtgcct ggagtacacg ctggcccggc tgccgaaggc cgatgccgcc    8220
attcaggcca agctggccgt gagcgccgcc gagcagcgcc agtggcagga cattatcgac    8280
cacatgtact atccggagga caagaagctg ggcatcttcg tccagcacga caccttcctg    8340
gataaggacc tgcggccggc aagctcgatt ccggccgacc agcggccaat caaccagcac    8400
tggtcctggg accgaatcct gcggtcgccg ttcatcaagc aggcggatgt gctccagggc    8460
```

```
ctgtacttcc tgaacaatcg cttcacccgc gagcagaagg aacgcaattt tgacttctac    8520
gagccgctga cggtgcacga aagctcgctg agtgcctcga ttcacgcggt gctggccgcc    8580
gagctcggta agcaggataa ggccgttgaa ctctatcagc gtacggctcg tctggacctg    8640
gacaactaca acaacgatac ggcagacggt ctgcacatca cctcgatgac cggcggctgg    8700
ctggctatcg tgcagggctt cgccggcatg cgctacgacc acgatcagct gcggttcgat    8760
ccgttcctgc cgaagcagtg gcagggttac cagttccgca tcaactaccg cggccgggtg    8820
atccaggtcg cggtggggaa aaccgttgca gtgaccctgc tggccggccc gccgctgacc    8880
gtcatggttg ccggccagcc gcagcatttg gaggtgagcg cgcatgctta aaggattgct    8940
gttcgacctc gacggcgtct tgaccgactc ggccaagttc cacctgcagg cctggagcca    9000
gctggccacc cagctgggca tcaccctgac gccggccgag cgcgaaggcc tgcgcggccg    9060
ctcgcggctg gactcgctga acctgatttt ggcggcaggc gcccaggaag accggttcag    9120
tgccgcagag aaaacggcgc taaccgacca gaagaacgcg gtgtacctga agctgattca    9180
gacgatgacg ccggtggaca tcctgccggg cattccgcaa ctgctgaagg acgcgcaggc    9240
ggccggcctg aaaatggcaa tcgcctcggc gtcgcggaac gccccgacaa ttcttgacca    9300
cctgggcctg gccgccagtt tcgacgccat cgtcgatccg gcgaccctgc accgcggcaa    9360
gcccgacccg gagatctacc agcaggcgca agcgctgctg gggctccagg ccgccgaggt    9420
gatcggcttc gaggatgcct cggccggggt cgccgccatc aaagcggccg gtcagttcgc    9480
ggttggcatc gggatgcccg gcttctggc cgcagcggat tacctagtga aagacacggc    9540
ggccctgcag ctgagccagt tgcaagcggc gttcgccaaa gaaagtgggg agactaatgg    9600
ttgaaatcga cttggaccac ctctacaaga agtacgacga cggcgaggat tactcggtgg    9660
tggacttcga ccttcacatc aaggataagg agttcatcgt gttcgtcggc ccctcgggct    9720 gcggaagtc caccacgctg cgtatgattg cggggctgga ggacattacc aaaggcgagc    9780
tgaaaatcga cgataaggtg atgaacgacg tggcccccaa ggaccgcaac atcgccatgg    9840
tgtttcagaa ctacgccttg tacccgcaca tgtcagtgta cgacaacatg gcgttcggcc    9900
taaagctacg gcactacaag aaggaggaca tcgacaaacg cgtgcaaaac gcggcggaga    9960
tcctcggcct gaagccgttt ctcgaccgga gccggccgc cttgtccggg ggccagcggc    10020
agcgggtggc cttgggccgg gccatcgtcc gcgacgcccc aatttcctg atggatgagc    10080 cgttgtcgaa cctggacgcg aagctgcggg tgtccatgcg ggcggaaatc gccaagctcc    10140
accagcgcct gaacaccacc acgatttacg tgacccacga ccaaaccgag gccatgacta    10200
tggccgaccg ggttgtcgtc atgtccgttg gccacgtgca gcagattggc accccggccg    10260
agatttacca gaacccgcgg aaccagttcg tggccgggtt catcgggtcg ccggcgatga    10320
acttcttcaa catgacctac caggacggct tcgtcagcga cggccaaagc attcgcctca    10380
aagtgccgga aggccgggcg aagattctgg acgaccaagg gtacaacggc aaggaagtcg    10440
tgttcggcat ccggccggag gacatccatt cggaggaggc cttcctggag acctggccgg    10500
acgcggttat cagctcaacc gtgtcggtgt cagagctcct gggcgccacc gagcagcttt    10560
acctgaaggc ggatgacacc gagtacgttg ccaacgtcaa cgcgcgcgac ttccacaatc    10620
ccggggatca tgtgaaaatg ggcttcgacg tcaacaaggc gcacttcttc aacaaggaca    10680
cgaccatggc catcgtggct aagccgattc cgctggaagg ctgaggaggt gagtgcatga    10740
ccccatggtg gcagcaagcc gtcatttacc agatctaccc gaagagtttt caggacagca    10800
```

| | |
|---|---:|
| acggggatgg catcggcgat tgccggggga ttaccagtcg ccttgattac cttaagcggc | 10860 |
| tgggcgtcga tgccctttgg ctgagcccag tgtatgtgtc gcccggcgag acaacggct | 10920 |
| acgacatcgc ggactacgag gccatcgatc cccagttcgg gacgatggcc gacatggacg | 10980 |
| ccttgatcgc cgccgccaag cagcgcg | 11007 |

<210> SEQ ID NO 17
<211> LENGTH: 977
<212> TYPE: DNA
<213> ORGANISM: Lactobacillus paracasei

<400> SEQUENCE: 17

| | |
|---|---:|
| cccgcgattt tggcgtgatt ggcttcgacg gggtattcct ggaccaggtg tccaacccca | 60 |
| agctgaccac ggtgaagcag cccgtgcagc gcctcggcga actgctggcc cgcatgctcc | 120 |
| tgcagaaggt ggcacagtcc ggcgcccaac agggggagct gctggtcgat cctgagctga | 180 |
| ttgctcggga cacgacgcga aagtagatcg gatttcaact gtccttaccg ctatggtagg | 240 |
| gccagttttt aggctctatg tcaaatctaa ttcatagcta atagttgatt tggcaacgcc | 300 |
| taaggcgtca gccatatctt ggtaagtatg atggccttca ctgaccagtt gagctagcgc | 360 |
| accacgttga aaacgtgata agtagaagt acccaaagta atcactcctt atagctggtt | 420 |
| ggaattaact actccattgt aagagattgc tttgggcctt tttttatttt tgttcggatt | 480 |
| aattatagaa tttgtctaat tagttgaaaa ttcttagggt tgcccatata tcttttagtc | 540 |
| tggtcattag tttttatgtt tgatctgctt ttttctgatc gcaaacaccc acaactgcga | 600 |
| gtgagtcctt tttgaagtcg ttgactgtca acaatacatt tatttccaca ttgacattga | 660 |
| cagagccaaa gcgcgttgcc attagaactg cttccaaaaa agctaataac tgtgagtcgc | 720 |
| ccaaacgttt gattagctaa atcgatacgc ttttgcatac taatcctccc gcttgataag | 780 |
| aaggtactta aatagttgct ttcaattgat ctaatcgcca ttggcaccat gaaataaagg | 840 |
| ctaattcgtc aatctttgga atgccatagg ttctagcata cgttaacttt tgagtggtga | 900 |
| gtagttgatc atagggttta ctaataatac caaccacaag gatatcgact tttttgtcaa | 960 |
| tcccgttgac aggcttt | 977 |

<210> SEQ ID NO 18
<211> LENGTH: 1239
<212> TYPE: DNA
<213> ORGANISM: Lactobacillus paracasei

<400> SEQUENCE: 18

| | |
|---|---:|
| aaatacgcaa aagaacccga cgagagttaa gtctcatcgg gttctcagtc gtggatgaat | 60 |
| tagaagcatt gttagctgca taaccttcaa cataggatca atagctggtt agatggtcat | 120 |
| ctctcagact gtttgcacca gatccaggca aacgtgttta tatccttggt catactcagg | 180 |
| atagatgggc attgtgagtg caacaggact tagttgcttg tatgctaggc aatgttggcc | 240 |
| ttgatacaga ggatcactct gtttctgatc tggatgataa cctcgttttt ccatttcagg | 300 |
| acgctgtccc aataattgtt gccctgggag tttgtcgaat taagtcttgg tgccacaaac | 360 |
| acacgctacg gcttctttc ttgcaaactg atcttagtat ttagggcagt tgcatgatta | 420 |
| cggaattgaa ccatttttata tgaatcgtc ttttctataa gtctatagaa agtgcaggta | 480 |
| atggcatttt ctccagatcg gattgtctaa tcaatttaat tgatttttt ggtgtgtttg | 540 |
| attatattgc ttttgcaaag gtacaatata ccttttctct gctgccttgc gagcagcgat | 600 |
| ggcatcctcc atatgaacat atacacgatt taggacaaga tggccttgaa agtacagcct | 660 |

```
tgcgacccac ttttgagcag ttttatccca actaactccg ataacgccag atttgttatt      720
ggaccgttta agtgtagaag caactaaatt tgttcgatta attagttgaa aattcttggg      780
attgcccatg tattttttag tctggttatt agcttttatg tttgatctgc ttatttctga      840
tcgcaaacac ccacaactgc gagtgagtcc tttttgaagt cgttgactgt caacgataca      900
tttatttcca cattgacatt gacagagcca aagcgcgttt ccattagaac tgcttccaaa      960
aaaactaatg actgtgagtc gtccaaacgt ttgattggcc aaatcgatac gcttttgcat     1020
actaatctcc ccgtttgata agaaggtact taaagagttg ttttcaattg atctagtcgc     1080
cattggcacc atgaaataaa ggctaattcg tcaatctttg gaatgccata ggttctagca     1140
tacgttaact tttgagtggt aagtagttga tcatagggtt tgctaataat accaaccaca     1200
aggatatcga cattttttgtc aatcccgttg acaggtttt                           1239
```

<210> SEQ ID NO 19
<211> LENGTH: 7
<212> TYPE: PRT
<213> ORGANISM: Artificial Sequence
<220> FEATURE:
<223> OTHER INFORMATION: peptide

<400> SEQUENCE: 19

Pro Asp Leu Lys Asp Val Gly
1               5

POSTBIOTIC-BASED COMPOSITION FOR THE MODULATION OF IMMUNE SYSTEM ACTIVATION AND PROTECTION OF MUCOSAL BARRIERS

CROSS-REFERENCE TO RELATED APPLICATIONS

This application is a 371 of PCT/EP2019/052669, filed Feb. 4, 2019, which claims the benefit of Italian Patent Application No. 102018000002370, filed Feb. 2, 2018.

FIELD OF THE INVENTION

The invention refers to a composition comprising *Lactobacillus casei* or *paracasei* species postbiotic, preferably for the modulation of immune system and the protection of mucosal barriers and to a method for obtaining the same. The invention relates also to the use of the postbiotic derived from *Lactobacillus casei* or *paracasei* in promoting human health, in particular in the prevention or treatment of inflammatory diseases and infections.

BACKGROUND OF THE INVENTION

In the initial years of human life, the microbiota is established and several environmental factors contribute to its generation, including nutrition (Bokulich et al., 2016). Newborns and in particular premature neonates are susceptible to infection because their immune system is non yet fully developed and functional (Goenka and Kollmann, 2015)(Shane et al., 2017).

The gut microbiota has several effects on physiological host functions, particularly the development and activity of the immune system [3, 4] resulting, under physiological conditions, in the tolerance of the commensals community, while maintaining the capacity to respond to pathogenic infection. The molecular basis of host-microbiota interactions is mainly mediated by a large variety of bioactive small molecules derived from bacterial metabolism and released during fermentation processes. Such metabolites are called postbiotics.

EP2402432 refers a fermentation product (fermented food) that has high functionality by subjecting a fructan-containing material (in particular, a material including garlic or rakkyo containing fructan, at a high concentration) directly to lactic acid fermentation without performing a heat treatment or an enzymatic treatment. More specifically, the EP application refers to a fermentation product having an immunopotentiating effect, which is obtained by lactic acid fermentation of a fructan-containing material using a lactic acid bacterium *Lactobacillus plantarum* S506 strain (NITE BP-643) having fructan-utilizing ability, a mutant strain of the S506 strain having fructan-utilizing ability, or a strain isolated from *Lactobacillus plantarum* and having the same bacteriological properties as those of the S506 strain; and a fermented food which contains the fermentation product.

It has been demonstrated that *L. paracasei* CNCM I-1390 strain is able to modulate the inflammatory response of immune cells through the action of the released postbiotics (Mileti et al., 2009). The putative therapeutic use of strains of *Lactobacillus paracasei* strain CNCM I-1390 (Budapest Treaty deposit), redeposited by IEO—Istituto Europeo di Oncologia S.r.l., Via Filodrammatici 10, 20121, Milano, Italy, on Jul. 26, 2017 according to Budapest Treaty with CNCM (Collection Nationale de Cultures de Microorganismes, Institut Pasteur, 25,28 rue du Docteur Roux 75724 Paris CEDEX 15, FR) mo. I-5220 (hereinafter also named as B21060), in particular of the fermentation supernatant thereof as an anti-inflammatory in intestinal diseases, is described in WO 2011/009848 A2. Postbiotics are very safe also on inflamed tissues, presumably because postbiotics lack the microbe associated molecular patterns that may further activate inflamed tissues (Tsilingiri et al., 2012).

Prebiotics

Prebiotics are defined as substrates that are selectively utilized by host microorganisms conferring a health benefit (The International Scientific Association for Probiotics and Prebiotics (ISAPP) consensus statement on the definition and scope of prebiotics, 2017) (Gibson et al., 2017). Prebiotic fibers are a full spectrum of dietary supplements that our body does not digest. Instead, prebiotics act as a substrate to promote the growth and the biological activity of particular microorganisms such as bifidobacteria and lactic acid bacteria resulting in many digestive and general health benefits. The most extensive documented dietary prebiotics are the non-digestible oligosaccharides fructans (fructooligosaccharides (FOS) and inulin) and galactans (galactooligosaccharides or GOS) and their effects includes mainly the activation of the human immune system (Fernandes et al., 2017) and intestinal homeostasis (Dahiya et al., 2017).

Probiotics and Postbiotics

Probiotics are defined as live microorganisms that exert beneficial effects on the host when administered in adequate amounts. Probiotics are in general isolated from faecal samples of healthy individuals, mostly breast-fed infants. The microbiota may belong to either symbiont or pathobiont classes of microorganisms and may have divergent immunomodulatory properties. It is worth pointing out that even among the same species different strains can have opposing effects, as has been shown in a number of studies (Kaci et al., 2011; Van Hemert et al., 2010). Further, recent data suggest that certain beneficial effects observed after probiotic administration may be mediated by molecules or factors produced and secreted by the bacteria into the gut lumen, henceforth herein called postbiotics. In the context of the present invention postbiotic (or "fermented product" or "fermented supernatant") is intended as any factor resulting from the metabolic activity of a probiotic or any released molecule capable of conferring beneficial effects to the host in a direct or indirect way. It is still felt the need of a postbiotic, and thus of a method to obtain it, able to modulate the immune system and the protection of mucosal barriers.

DESCRIPTION OF THE INVENTION

The present invention relates to the development and characterization of a postbiotic (a preferred embodiment of such postbiotic is herein named by the inventors "ImmunoFOS") derived from the fermentation of the fructo-olygosaccharide (FOS) by *Lactobacillus paracasei* strain CNCM I-5220, to be used to modulate the immune system and to protect mucosal barriers from infectious agents.

The fermented product can favor the control of immune responses towards the release of anti-inflammatory cytokines that can be protective against immunopathology derived from an exaggerated inflammatory response. In addition to its immunomodulatory activity on the cells of the Immune system, ImmunoFOS modulates the inflammatory response of epithelial cells to pathogens, favoring the maintenance of a proficient epithelial barrier. It is comprised within the present invention also any postbiotic derived from the fermentation of different prebiotic fibers by *Lactobacillus paracasei* strain CNCM I-5220.

It is therefore an object of the invention a composition comprising:
- a) a fermented supernatant, or fractions thereof, of *Lactobacillus casei* or *paracasei* species, said species being characterized by comprising in their DNA genome at least one DNA sequence essentially identical to one of the sequence selected from the group consisting of: SEQ ID NOs: 1 to 5, and
- b) proper carriers and/or diluents and/or excipients, wherein said fermented supernatant is obtainable through a method characterized by the fermentation of said *Lactobacillus casei* or *paracasei* species in a minimum solution additioned with prebiotic fibers and wherein said fermented supernatant doesn't comprise prebiotic fibers.

Said minimum solution is preferably a solution which does not contain carbon and/or nitrogen sources or micromolar concentration of minerals (e.g. iron, sulfur etc.) and which doesn't comprise prebiotic fibers.

More preferably, the minimum solution is saline, phosphate buffer, $H_2O$, a minimum isotonic solution or a hypotonic solution.

The above method preferably comprises two fermentations of said *Lactobacillus casei* or *paracasei* species into a minimum solution, at least one of which is carried out into a minimum solution additioned with prebiotic fibers.

Said prebiotic fibers are preferably selected from the group consisting of: fructooligosaccharides (FOS), nondigestible oligosaccharides (NDOs), resistant starch, pectin, beta-glucans, inulin, lactulose, polydextose, isomaltooligosaccharides (IMO), xylooligosaccahrides (XOS), lactitol, chicory root inulin-derived (FOS), wheat bran-derived arabinoxylooligosaccharides (AXOS), xylooligosaccharides (XOS), mannitol, maltodextrin, raffinose, lactulose, sorbitol, galactooligosaccharides (GOS) and combinations thereof.

More preferably, the prebiotic fibers are fructooligosaccharides (FOS).

In a preferred embodiment of the invention, said fermented supernatant is a dry powder, e.g. obtained by lyophilization, freeze-drying, granulation, spray drying.

The fermentation is preferably carried out at a temperature of 25-40° C., preferably of 37° C.

Preferably, the fermented supernatant comprises:
- a) after a first fermentation into a minimum solution:
  oleic acid and/or decanoic acid and/or benzopropanoic acid and/or citric acid, preferably in the following concentration:
  oleic acid: 3-9 mg/L, preferably 4-8 mg/L, more preferably about 7.98 mg/L; and/or
  decanoic acid: 1-3 mg/L, preferably about 1.30 mg/L; and/or
  benzopropanoic acid: 1-4 mg/L, preferably 2-3 mg/L; more preferably about 2.69 mg/L and/or
  citric acid: 10-15 mg/L, preferably 12-14 mg/L; more preferably about 13.05 mg/L, even more preferably the fermented supernatant comprises:

|  | mg/L |
|---|---|
| oleic acid | 7.98 |
| decanoic acid | 1.30 |
| benzopropanoic acid | 2.69 |
| citric acid | 13.05 | and/or
- b) after a second fermentation into a minimum solution additioned with prebiotic fibers a fatty acid concentration <about 0.01 mg/L.

Preferably, the fermented supernatants, when analyzed by MALDI TOF mass spectrometry, are characterized by the peptide signal profile of Table 2A.

Preferably, the fermented supernatant, after two fermentations of said *Lactobacillus casei* or *paracasei* species into a minimum solution, at least one of which is carried out into a minimum solution additioned with prebiotic fibers, when analyzed by MALDI TOF/TOF mass spectrometry, is characterized by the peptide signal profile of Table 2B.

Preferably, the fermented supernatant after two fermentations of said *Lactobacillus casei* or *paracasei* species into a minimum solution, at least one of which is carried out into a minimum solution additioned with prebiotic fibers, is characterized by comprising at least the peptide of p 19.

Said fermented supernatant is preferably obtainable by a method characterized by:
- a) growing an inoculum of *Lactobacillus* strain as defined in any one of claims 1-4 in a suitable culture medium, at a temperature ranging from 4 to 40° C., preferably of 37° C., to have a biomass and allowing fermentation of said biomass into a minimum solution to proceed for 12 to 36 hours, preferably for about 24 hours, to get a fermented biomass;
- b) centrifuging said fermented biomass to get a pellet fermented biomass and a first fermented product;
- c) incubating said pellet fermented biomass into a minimum solution and allowing further fermentation for 12 to 36 hours, preferably for about 24 hours, at a temperature ranging from 4 to 40° C., preferably 25-40° C., more preferably of 37° C., to get a further fermented biomass;
- d) separating said further fermented biomass from a second fermented product by centrifugation wherein at least one of the minimum solution of step a) and c) is additioned with prebiotic fibers, preferably only the minimum solution of step c) comprises prebiotic fibers.

Preferably, the species are characterized by comprising in their DNA genome the DNA sequences essentially identical to SEQ ID NOs: 1 to 5.

More preferably, the *Lactobacillus* species is *Lactobacillus paracasei*, preferably the *Lactobacillus paracasei* is a strain characterized by comprising in its DNA genome at least one DNA sequence essentially identical to SEQ ID NOs: 6 to 18, preferably said strain comprises in its DNA genome DNA sequences essentially identical to SEQ ID NOs: 6 to 18. In a preferred embodiment of the invention the *Lactobacillus paracasei* is the strain deposited according to Budapest Treaty with no. CNCM I-5220.

The strain B21060 (or CNCM I-5220) was deposited under the Budapest Treaty at Collection Nationale de Cultures de Microorganismes (CNCM), with number CNCM I-5220 on 26 Jul. 2017 (deposit information:
Microorganism Deposit Accession No.: CNCM I-5220;
Depositary Institution name: Collection nationale de cultures de microorganismes (CNCM));
Depositary Institution address: Institut Pasteur, 25 Rue du docteur Roux, 75724 Parise Cedex 15, France;
Deposit Date: 26 Jul. 2017
Name and Address of Depositor: IEO—Istituto Europeo di Oncologia S.r.l., Via Filodrammatici 10, 20121 Milano, Italy).

The composition according to the invention is preferably in the form of a liquid, topic, preferably cosmetic (as e.g.

shampoo, toothpaste, mouthwash, etc.) or cream, solid, preferably capsules or free powder or ocular, preferably eye-drops, formulation, said formulation being preferably suitable to be ingested, topically applied, introduced in an enema for external or internal use.

More preferably, in the composition according to the invention the fermented product, or fractions thereof, is present at 0.02-40% weight/volume (w/v), more preferably 1% weight/volume (w/v).

A further object of the invention is a probiotic, pharmaceutical, nutraceutical, cosmetic, food, food supplement or feed composition comprising the composition according to the invention. The composition according to the invention preferably further comprises adjuvants and/or therapeutic agents, preferably at least one anti-inflammatory drug.

Preferably, the composition according to the invention is for use as a medicament, more preferably for use as an immunomodulating agent and/or in the treatment and/or prevention of infections or in the treatment and/or prevention of immunopatologies derived from an exaggerated inflammatory response, more preferably for the treatment of allergies, preferably Asthma, dermatitis, conjunctivitis, inflammatory chronic disorder, preferably inflammatory bowel disease, irritable bowel syndrome, mucositis and stomatitis, vaginitis, in human and veterinary medicine.

Another object of the invention is a method for obtaining the fermented product as defined in any of previous claims, characterized by:
a) growing an inoculum of *Lactobacillus* strain as defined in any one of claims 1-4 in a suitable culture medium, at a temperature ranging from 4 to 40° C., preferably of 37° C., to have a biomass and allowing fermentation of said biomass into a minimum solution to proceed for 12 to 36 hours, preferably for about 24 hours, to get a fermented biomass;
b) centrifuging said fermented biomass to get a pellet fermented biomass and a first fermented product;
c) incubating said pellet fermented biomass into a minimum solution and allowing further fermentation for 12 to 36 hours, preferably for about 24 hours, at a temperature ranging from 4 to 40° C., preferably of 37° C., to get a further fermented biomass;
d) separating said further fermented biomass from a second fermented product by centrifugation
wherein at least one of the minimum solution of step a) and c) comprises prebiotic fibers, preferably only the minimum solution of step c) comprises prebiotic fibers.

In a further embodiment, both the minimum solutions of step a) and c) comprise prebiotic fibers.

Said minimum solution is preferably a solution which does not contain carbon and/or nitrogen sources or micromolar concentration of minerals (e.g. iron, sulfur etc.) and which doesn't comprise prebiotic fibers, preferably the minimum solution is saline, phosphate buffer, H$_2$O, a minimum isotonic solution or a hypotonic solution.

A further object of the invention is the fermented supernatant, or fractions thereof, obtainable by above defined method. First and/or second fermented supernatant obtainable from step b) or d) respectively are an object of the invention and collectively will be defined as "fermented product". They may be used as active ingredients for the composition and formulation, either individually or combined. In the case wherein only step c) comprises prebiotic fibers, only the second fermented product is to be considered object of the invention.

A further object of the invention is a method for manufacturing the composition as defined above, comprising adding the fermented supernatant, or fraction thereof, as above defined, to at least one carrier and/or diluent and/or excipient and/or adjuvant and/or therapeutic agent. In the context of the present invention, for "minimum solution" it is preferably intended a solution which does not contain carbon and/or nitrogen sources or micromolar concentration of minerals (e.g. iron, sulfur etc.) and which doesn't comprise prebiotic fibers.

Preferably the minimum solution is saline, phosphate buffer, H$_2$O, etc. It may be e.g. a minimum isotonic solution or a hypotonic solution.

In the context of the present invention a "minimum isotonic solution" is defined as solutions, with osmolality similar to the blood and body fluid (290 mOsmol/1), while a "minimum hypotonic solution" is a solution that have an osmolality lower than the body fluid (<280 mOsmol/1) which actively promotes fluid absorption.

In the context of the present invention the term "fermented product" and "fermented supernatant" are exchangeable. In the context of the present invention the fermented supernatant also comprises any factor resulting from the metabolic activity of a probiotic or any released molecule capable of conferring beneficial effects to the host in a direct or indirect way. The preferred supernatant of the invention, ImmunoFOS, is a postbiotic product obtained by the fermentation of fructo-olygosaccharide (FOS) by *L. paracasei* CNCM I-5220 and does not contain food and live bacteria. Said preferred embodiment herein named ImmunoFOS is preferably lyophilized. In the context of the present invention "the solution supernatant" or the "fermented supernatant" may be also defined as "fermented product" and may also include fractions thereof and/or metabolic components thereof. The fermented product or composition according to invention may be lyophilized according to any method known to the skilled in the art. The food product or food supplement according to the invention comprises an amount of the above defined composition (or fermented product or supernatant) effective for imparting the above defined properties to the food product. In a preferred embodiment of the invention, the composition of the invention comprises a fermented supernatant as above defined and at least one vitamin selected from the group of vitamin D3, Vitamin K, Vitamin B1, B6, B12 and/or at least one chemical element such as Zinc or galactagogue, and/or at least one erb extract (such as *Echinacea*, malva, camomile etc). In a preferred embodiment, the fermented product (or supernatant) is the above defined ImmunoFOS. In a more preferred embodiment of the invention, the composition comprises 0.4% to 20% ImmunoFOS (or other supernatant product according to the invention) supplemented with at least one vitamin selected from the group of vitamin D3, Vitamin K, Vitamin B1, B6, B12 and/or at least one chemical element such as Zinc or galactagogue, and/or at least one erb extract (such as *Echinacea*, malva, camomile etc). In a preferred embodiment, the composition comprises 0.4% to 20% ImmunoFOS (or other supernatant product according to the invention) supplemented with at least one vitamin selected from the group of vitamin D3, Vitamin K, Vitamin B1, B6, B12 and at least one chemical element such as Zinc or galactagogue, and at least one erb extract (such as *Echinacea*, malva, camomile etc). The composition according to the invention may also comprise flavors, thickeners, as xhantan gum, water, sugars, as fructose, preservatives, potassium sorbate and sodium benzoate. The food product of the invention is preferably selected from the group consisting of fruits and fruit derived products, milk and derivatives thereof, vegetables and vegetable derived products, grain and grain derived products, dairy products, meat, poultry, seafood, chocolates and chocolate bars, cereal bars, gummies, chewing-gums, ice-cream and mixtures thereof. It is another object of the invention the use of the fermented product as above defined for preparing a food product, a nutraceutical, a feed, a cosmetic or pharmaceutical composition. The pharmaceutical composition according to the invention is formulated to be administered to a subject in a therapeutically effective amount, depending on e.g. type of subject, disease severity and route of administration. Typically, the therapeutically effective amount of the fermented product is about 1-1000 mg/day, preferably 200 mg/day or of e.g. 1 to 1000 mg. The administration is e.g. carried out with 1-2 administration/die of 1 gr of fermented product or composition as defined above, at the concentration of 0.1 to 40% of product. The fermented product or supernatant (or the composition comprising it) can be administered via any suitable route of administration. For example, the composition according to the invention may be administered to animals (including humans) in an orally ingestible form. In case of a food composition or nutraceutical, the fermented product can simply be incorporated in a conventional food item or food supplement. Exemplary pharmaceutical formulations include capsules, microcapsules, tablets, granules, powder, troches, pills, suppositories, suspensions and syrups. In another embodiment, the composition is in a form for rectal administration to an animal (including humans), for instance as rectal suppository or enema. Suitable formulations may be prepared by methods commonly employed using conventional organic and inorganic additives. The amount of active ingredient in the medical composition may be at a level that will exercise the desired therapeutic effect. The composition may contain further useful ingredients, including probiotics. The formulation may contain fillers and extenders, such as maltodextrin or pullulan. Preferably, the above defined species are characterized by at least one of the gene selected from the group consisting of SEQ ID NOs: 1-5 and/or by at least one of the gene selected from the group consisting of SEQ ID NOs: 6-8 and/or by at least one of the genome DNA sequences selected from the group consisting of SEQ ID NOs: 9-18. Preferably, the above defined species are characterized by the genes having the sequences essentially identical to SEQ ID NOs: 1-5. Preferably, the above defined species are characterized by the genes having the sequences essentially identical to SEQ ID NOs: 6-8. Preferably, the above defined species are characterized by genome DNA sequences essentially identical to SEQ ID NOs: 9-18. In the context of the present invention, when referring to specific DNA sequences, it is intended that it is comprised within the invention also RNA molecules identical to said polynucleotides, except for the fact that the RNA sequence contains uracil instead of thymine and the backbone of the RNA molecule contains ribose instead of deoxyribose, RNA sequence complementary the sequences therein disclosed, functional fragments, mutants and derivatives thereof, proteins encoded therefrom, functional fragments, mutants and derivatives thereof. The term "complementary" sequence refers to a polynucleotide which is non-identical to the sequence but either has a complementary base sequence to the first sequence or encodes the same amino acid sequence as the first sequence. A complementary sequence may include DNA and RNA polynucleotides. The term "functional" or "functional" may be understood as capable of maintaining the same activity. "Fragments" are preferably long at least 10 aa., 20 aa., 30 aa., 40 aa., 50 aa., 60 aa., 70 aa., 80 aa., 90 aa., 100 aa., 150 aa., 200 aa., 300 aa., 400 aa., 500 aa., 600 aa., 700 aa., 800 aa., 900 aa., 1000 aa., 1200 aa., 1400 aa., 1600 aa., 1800 aa. or 2000 aa. "Derivatives" may be recombinant or synthetic. The term "derivative" as used herein in relation to a protein means a chemically modified protein or an analogue thereof, wherein at least one substituent is not present in the unmodified protein or an analogue thereof, i.e. a protein which has been covalently modified. Typical modifications are amides, carbohydrates, alkyl groups, acyl groups, esters and the like. As used herein, the term "derivatives" also refers to longer or shorter polynucleotides/proteins and/or having e.g. a percentage of identity of at least 85%, 86%, 87%, 88%, 89%, 90%, 91%, 92%, 93%, 94%, 95%, 96%, 97%, 98%, more preferably of at least 99% with the sequences herein disclosed. In the present invention "at least 70% identity" means that the identity may be at least 70%, or 75%, or 80%, or 85% or 90% or 95% or 100% sequence identity to referred sequences. This applies to all the mentioned % of identity. Preferably, the % of identity relates to the full length of the referred sequence. In the context of the present invention a carrier may be any vehicle or composition involved in delivery of the fermented product into the subject or that facilitated the storage of the composition. The derivative of the invention also includes "functional mutants" of the polypeptides, which are polypeptides that may be generated by mutating one or more amino acids in their sequences and that maintain their activity. Indeed, the polypeptide of the invention, if required, can be modified in vitro and/or in vivo, for example by glycosylation, myristoylation, amidation, carboxylation or phosphorylation, and may be obtained, for example, by synthetic or recombinant techniques known in the art. In the present invention "functional" is intended for example as "maintaining their activity" e.g. immunomodulatory activity or anti-inflammatory activity. Also within the scope of the subject invention are polynucleotides which have the same nucleotide sequences of a polynucleotide exemplified herein except for nucleotide substitutions, additions, or deletions within the sequence of the polynucleotide, as long as these variant polynucleotides retain substantially the same relevant functional activity as the polynucleotides specifically exemplified herein (e.g., they encode a protein having the same amino acid sequence or the same functional activity as encoded by the exemplified polynucleotide). Thus, the polynucleotides disclosed herein should be understood to include mutants, derivatives, variants and fragments, as discussed above, of the specifically exemplified sequences. The subject invention also contemplates those polynucleotide molecules having sequences which are sufficiently homologous with the polynucleotide sequences of the invention so as to permit hybridization with that sequence under standard stringent conditions and standard methods (Maniatis, T. et al, 1982).

Polynucleotides described herein can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or greater as compared to a sequence exemplified herein.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, word-length=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/N1H website. According to the present invention, the above-mentioned prebiotic fibers are preferably contained in the fermentation medium in the amount of 0.5-25% by mass or more, preferably in the amount of 10% or more. According to the present invention, the pH of the fermentation medium is adjusted to be within the range of 5-7.5 prior to the fermentation. It is preferable that the pH be adjusted within the above-mentioned range, for example, by diluting with distilled water, etc., without using a pH adjustor after suitably processing the vegetative raw material, or by suitably adjusting the kind or amount of the vegetative raw material. If it is necessary to use a pH adjustor, one that is generally used for foods may be added as long as it does not deteriorate the effect of the present invention, and the kind thereof is not particularly limited. Examples of a preferable acid include citric acid, potassium sorbate, and examples of a preferable base include potassium carbonate. If the pH adjustor used is in a form of crystals, it is preferable to use an aqueous solution thereof. It is preferable that *Lactobacillus casei* or *paracasei* as defined above is used for the fermentation of medium after being precultivated. The precultivation may be carried out by using conventional methods. Fermentation of the medium using *Lactobacillus casei* or *paracasei* may be carried out by using conventional methods. For example, the above-mentioned precultivated product may be inoculated so as to cultivate said *Lactobacillus casei* or *paracasei*. The amount of inoculation is preferably in the range of 0.1 to 10% by volume, the temperature during the cultivation is in the range of 4 to 40° C., preferably of 37° C. and the time period for the cultivation is preferably 16-30 hours. According to the present invention, the pH of the fermented product at the end of the fermentation is 5.5 or greater and less than 7.0. If the pH is within this range, a suitable degree of fermentation may be obtained in order to produce a fermented food or drink which has excellent taste, flavor, and preservability. The obtained fermented product may be directly used as a fermented food or drink. Alternatively, suitable additives may be added, if necessary, or the product may be appropriately processed to be a fermented food or drink. The composition according to the invention also comprises a fermented product of *Lactobacillus casei* or *paracasei* having the same bacteriological properties as those of the CNCM I-5220 strain. The present invention relates to a fermentation product (or supernatant), which is obtained by fermentation of a prebiotic fibers-containing material (in particular, a material including FOS) using a specific *Lactobacillus casei* or *paracasei* strain, and more particularly, to a fermentation product having an immunomodulatory effect. The fermentation process is preferably as defined above. Further, the present invention relates to a fermented food having an immmunomodulatory effect, which contains the fermentation product. FOS are soluble dietary fibres belonging to the family of fructans. They are composed of linear chains of fructose units, linked by beta (2(1) fructosyl-fructose glycosidic bonds. The number of fructose units ranges from 2 to 60 and often terminate in a glucose unit. They can be produced, based on inulin degradation or transfructosylation processes. In the preset invention, the FOS-containing material is not limited as long as the material contains FOS, but the material is preferably one which contains fos at a high concentration. Specifically, the material is preferably one including one or more plants selected from Jerusalem artichoke, burdock, chicory, onions, asparagus, wheat, beans, tomatoes, fennel and other fruits, such as currant, bearberry, and vegetables and grains. The fermentation product of the present invention is preferably obtained by fermentation of the prebiotic fibers-containing material using a CNCM I-5220 strain, or a mutant strain of the CNCM I-5220 strain having the same ability, or a strain isolated from *Lactobacillus casei* or *paracasei* having the same bacteriological properties as those of the CNCM I-5220 strain. The fermentation may be performed until FOS contained in the above-mentioned material is sufficiently degraded. Specifically, the fermentation is performed under anaerobic conditions at a temperature of 4 to 40° C., preferably 10 to 37° C. The fermentation is desired to be performed at a pH of 4 to 8.0, preferably 5.0 to 7.0, particularly preferably about 6.5. The fermentation may be performed until prebiotic fibers contained in the above-mentioned material are sufficiently degraded, and for example, the fermentation may be performed for 16 to 48 hours. The fermentation product of the invention has as immunomodulatory activity since it has an effect of promoting anti-inflammatory cytokines release, in particular it reduces the release of IL-12p-40 and IL-12p-70, and increases the release of IL-10 in cells or mice stimulated by LPS. It should be noted that the above-mentioned fermentation product is desirably contained at a concentration of 1 to 20% or more in terms of dry weight. To obtain the immunomodulatory effect, the "fermented food" may be taken once or twice a day at 0.1 to 2.0 g/dose in terms of dry weight of the fermentation product contained. The invention will be illustrated by means of non-limiting examples with reference to following figures.

FIG. 1 Mass spectrometry profile of the fermented product supernatant of *Lactobacillus paracasei* strain CNCM I-5220 obtained by SACI technique.

Figure 2:
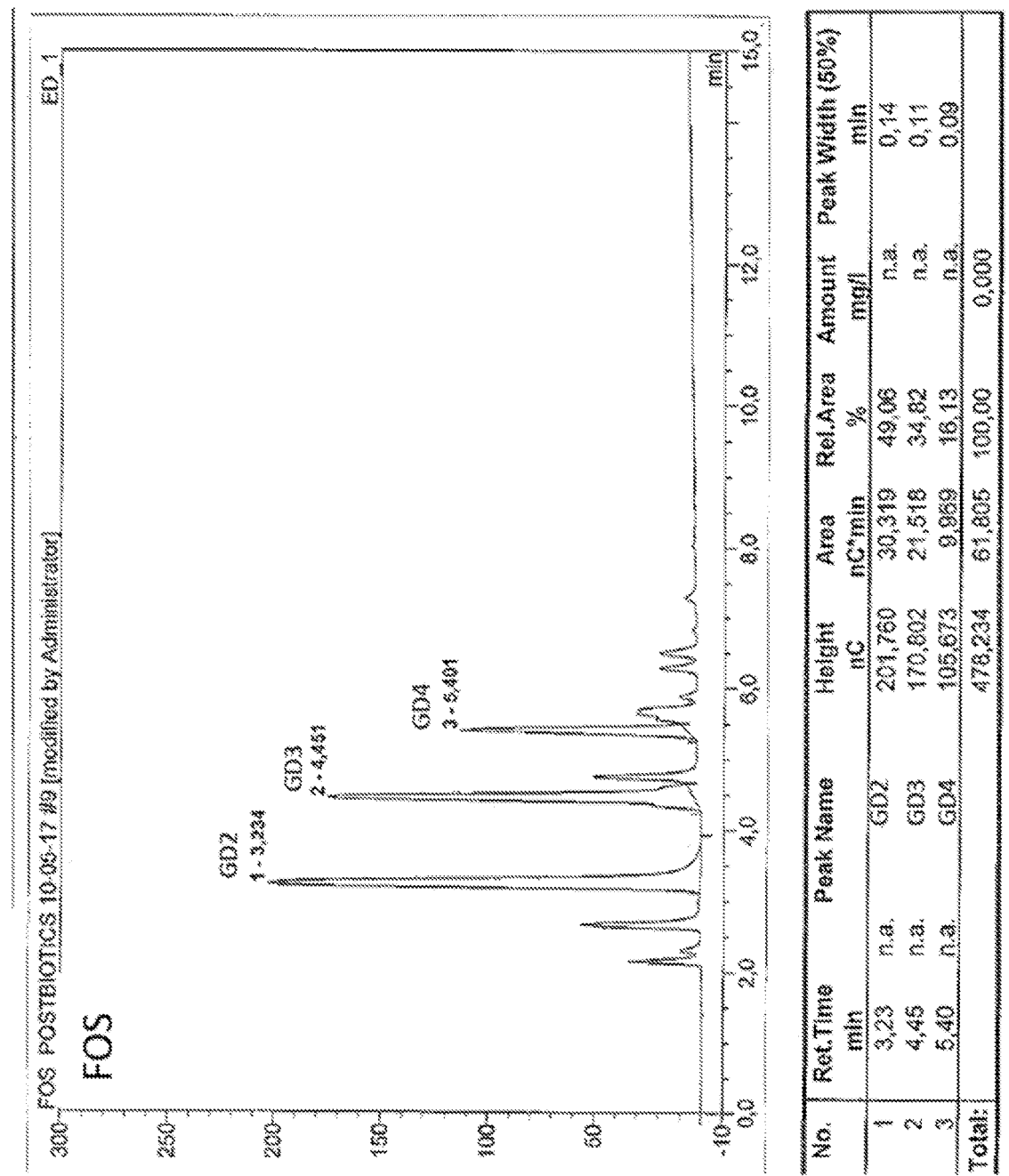
Figure 2:
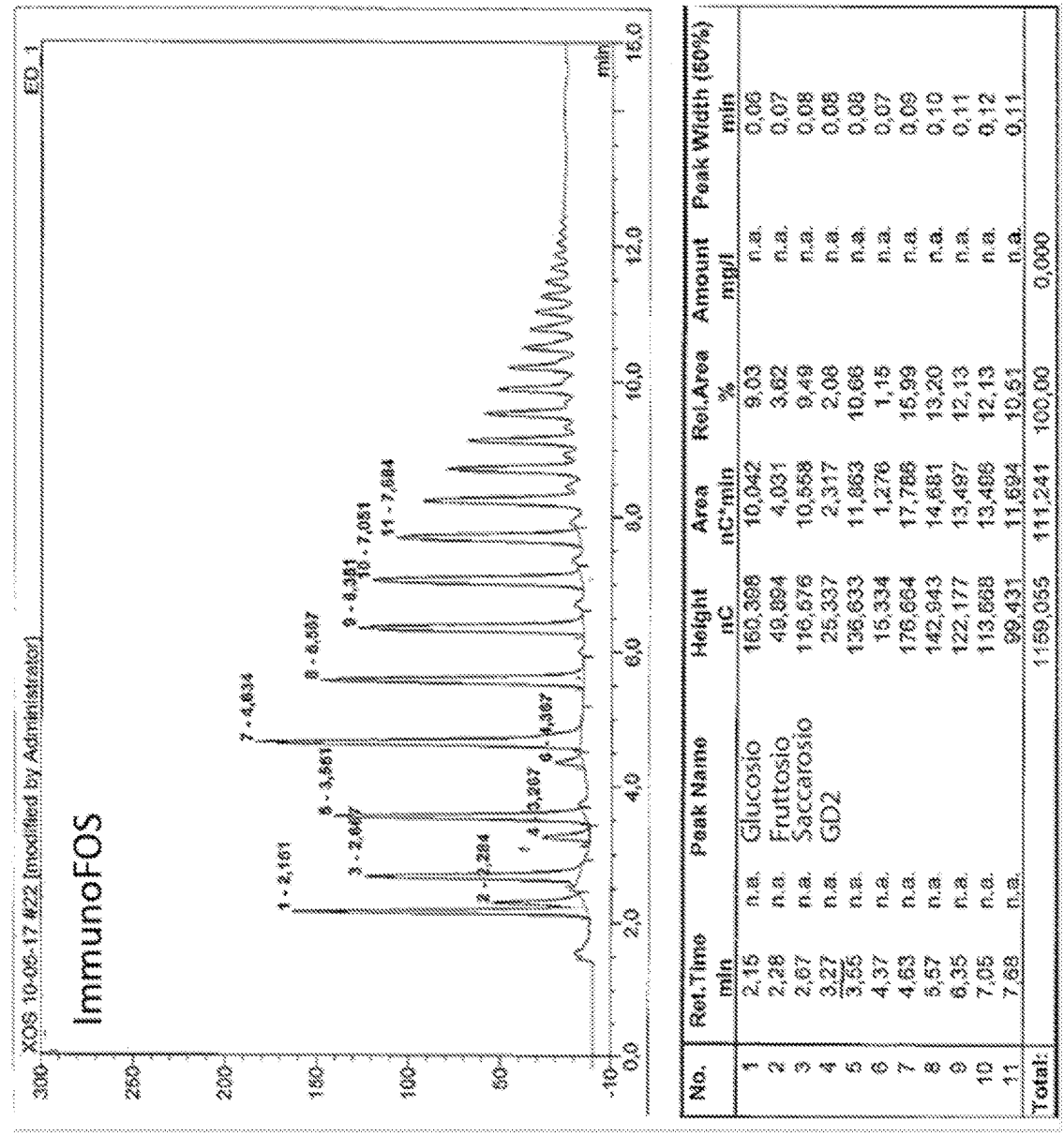

FIG. 2 HPAEC-PAD analysis profile of FOS (A) and ImmunoFOS® (B) (FOS fermentation by *Lactobacillus paracasei* strain CNCM I-5220).

Figure 3:
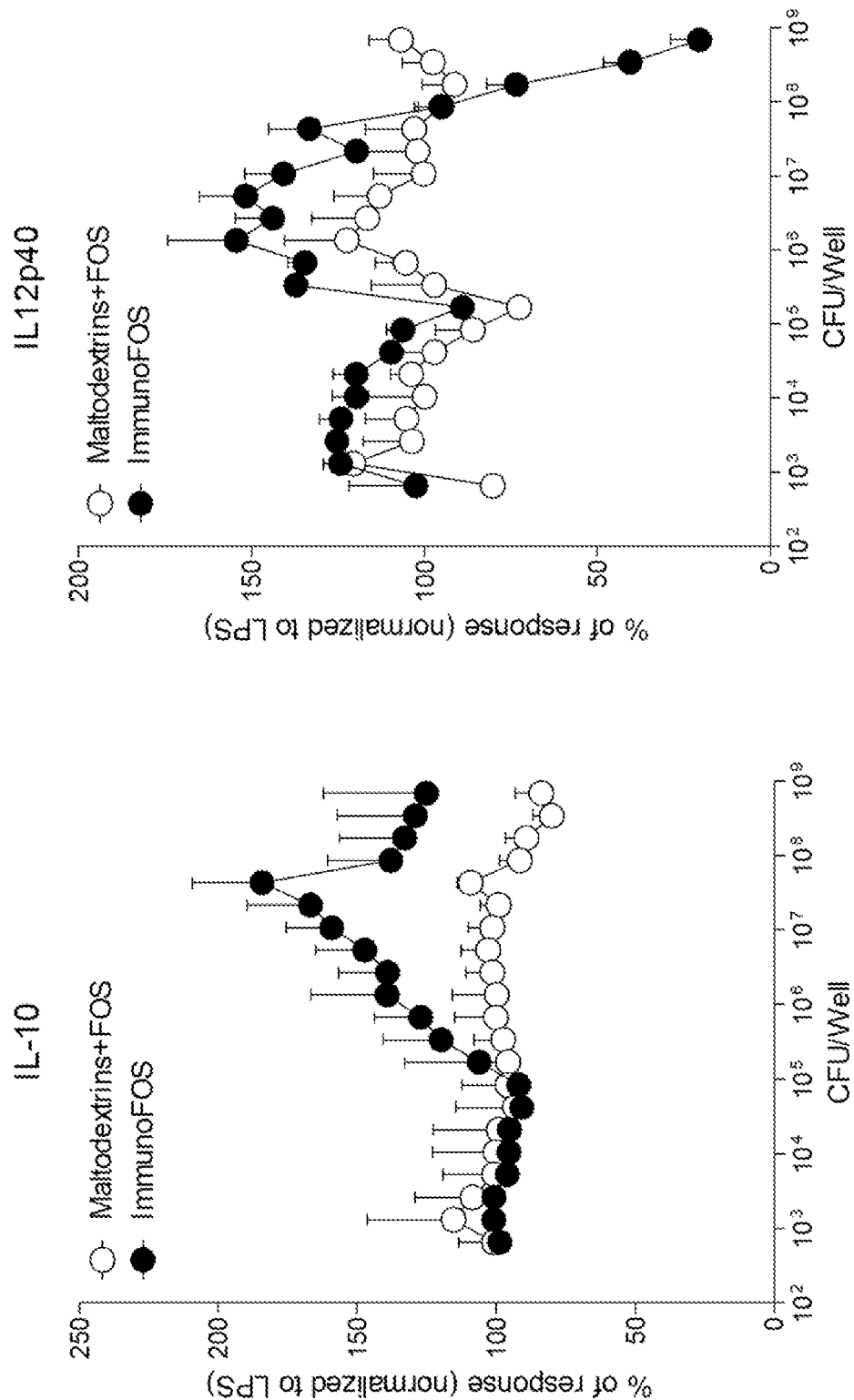

FIG. 3 PBMCs were stimulated with LPS (100 ng/ml) and treated with ImmunoFOS® or the control containing maltodextrins and FOS for 24 h. Concentrations of IL-10 and IL-12p40 as determined by ELISA.

Figure 4:
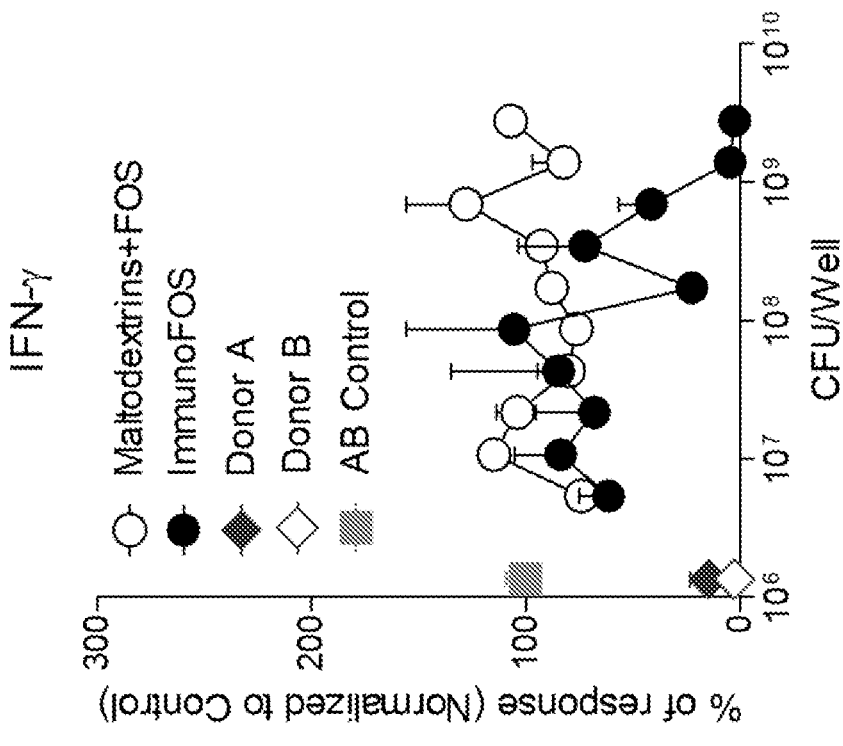
Figure 4:
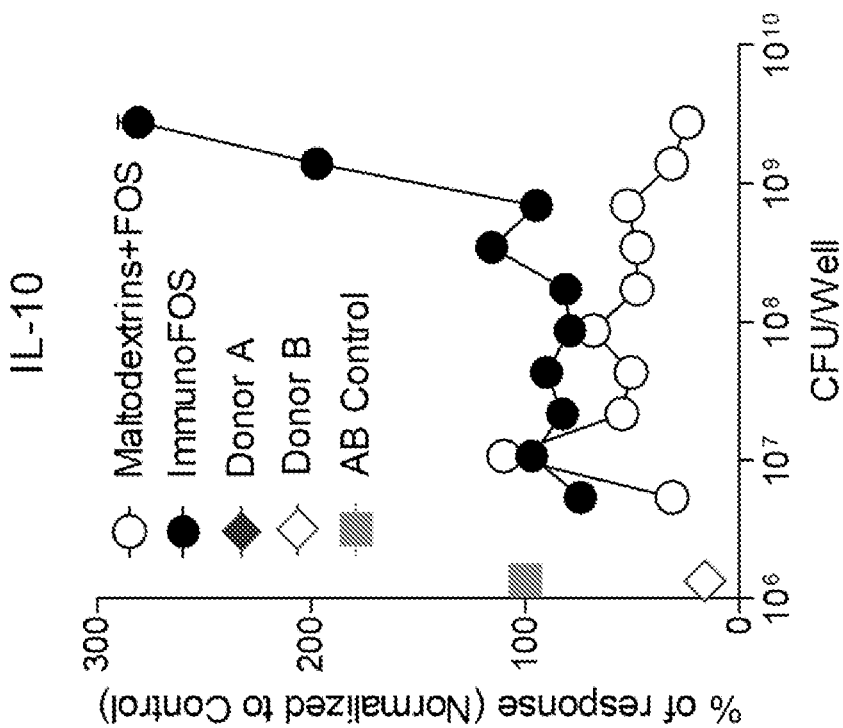

FIG. 4 PBMCs from genetically different individuals were mixed together in a reaction known as the mixed lymphocyte reaction (MLR). ImmunoFOS® and or the control containing maltodextrins and FOS were tested in a co-colture of PBMCs from different donors for 5 days. Concentrations of IL-10 and IFN-γ as determined by ELISA.

Figure 5:
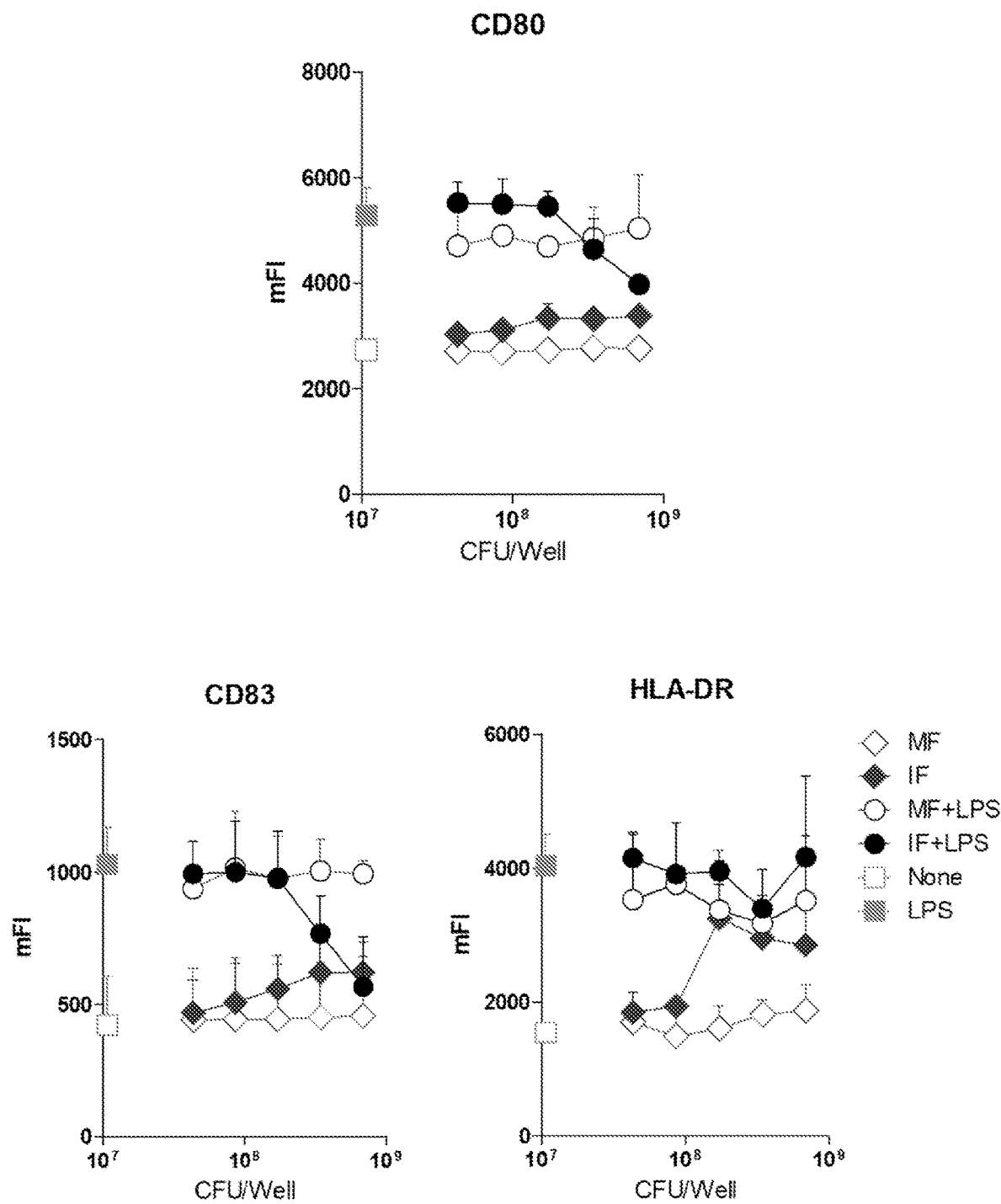

FIG. 5 MoDCs were stimulated with LPS (100 ng/ml) and treated with ImmunoFOS® or the control containing maltodextrins and FOS for 24 h. Surface co-stimulatory molecules expression, CD80, CD83 and MHC II, on moDCs as determined by Flow cytometry.

Figure 6:
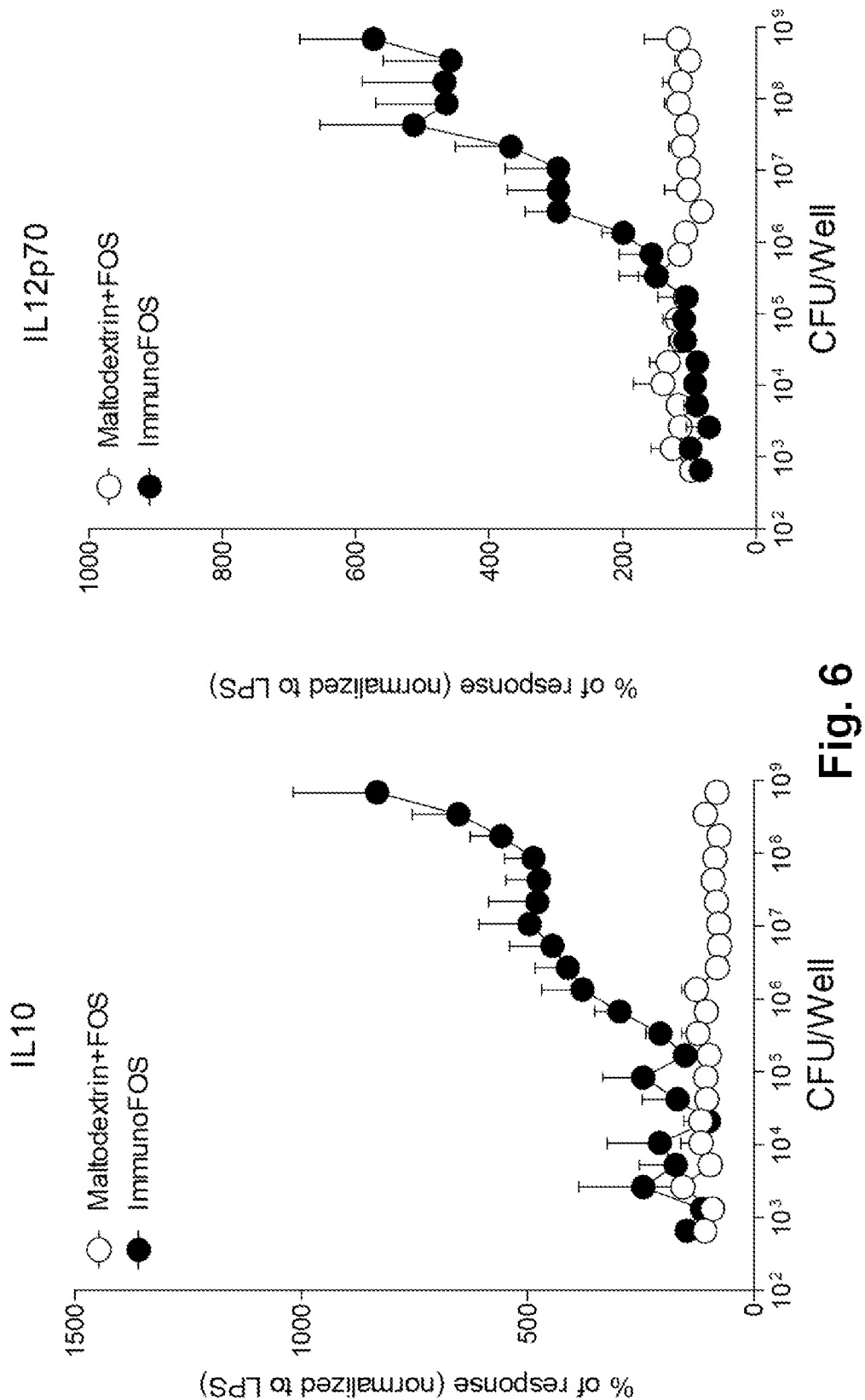

FIG. 6 MoDCs were stimulated with LPS (100 ng/ml) and treated with ImmunoFOS® or the control containing maltodextrins and FOS for 24 h. Concentrations of IL-10 and IL-12p70 as determined by ELISA.

Figure 7:
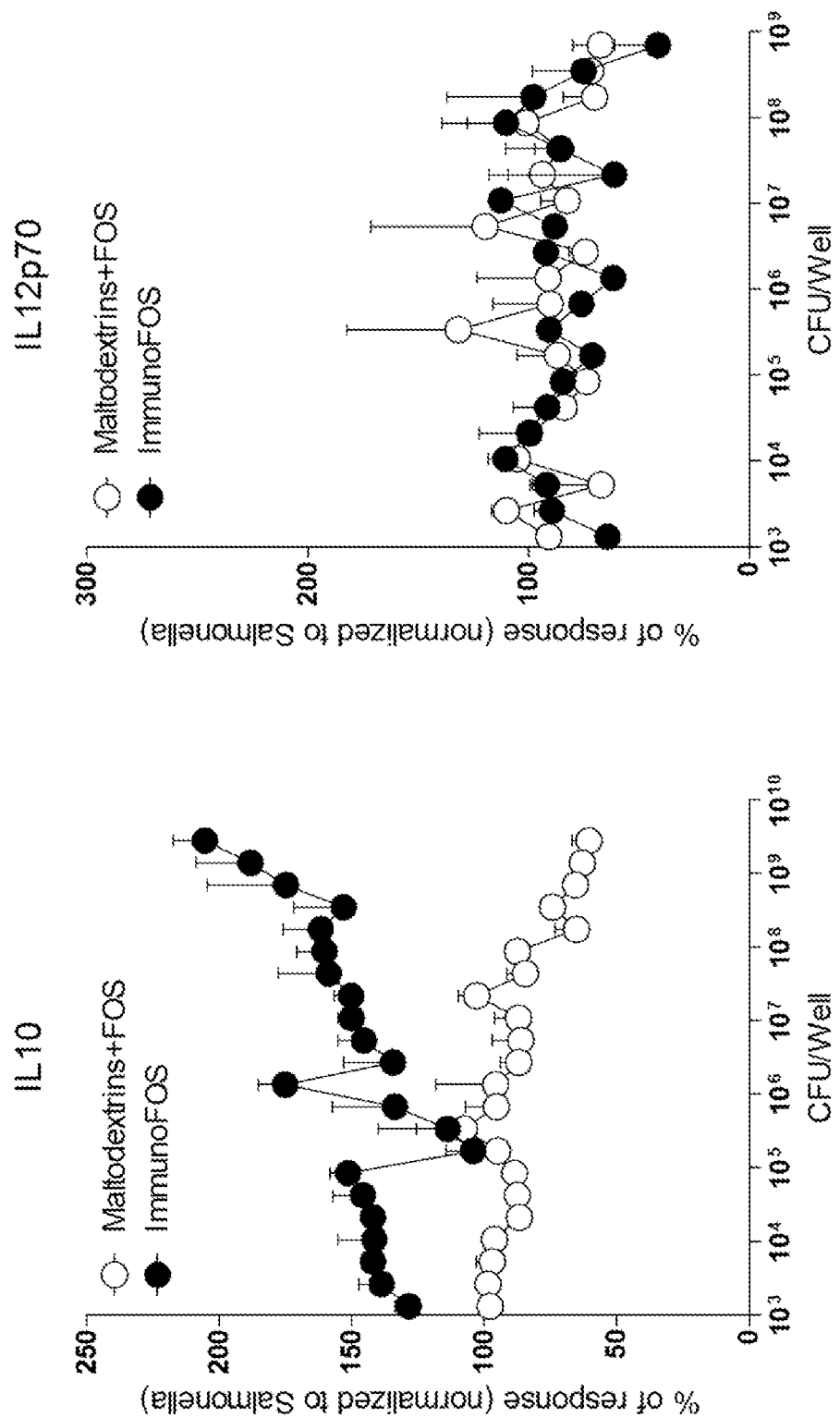

FIG. 7 MoDCs were infected with *Salmonella* SL1344 (MOI 1:1) and treated with ImmunoFOS® or the control containing maltodextrins and FOS for 1 hour. After that, *Salmonella* was inactivated with gentamicin (100 mg/ml) and, after 24 h of incubation, cytokine abundance (IL-10 and IL-12p70) was evaluated in culture medium. Concentrations of cytokines were determined by ELISA.

Figure 8:
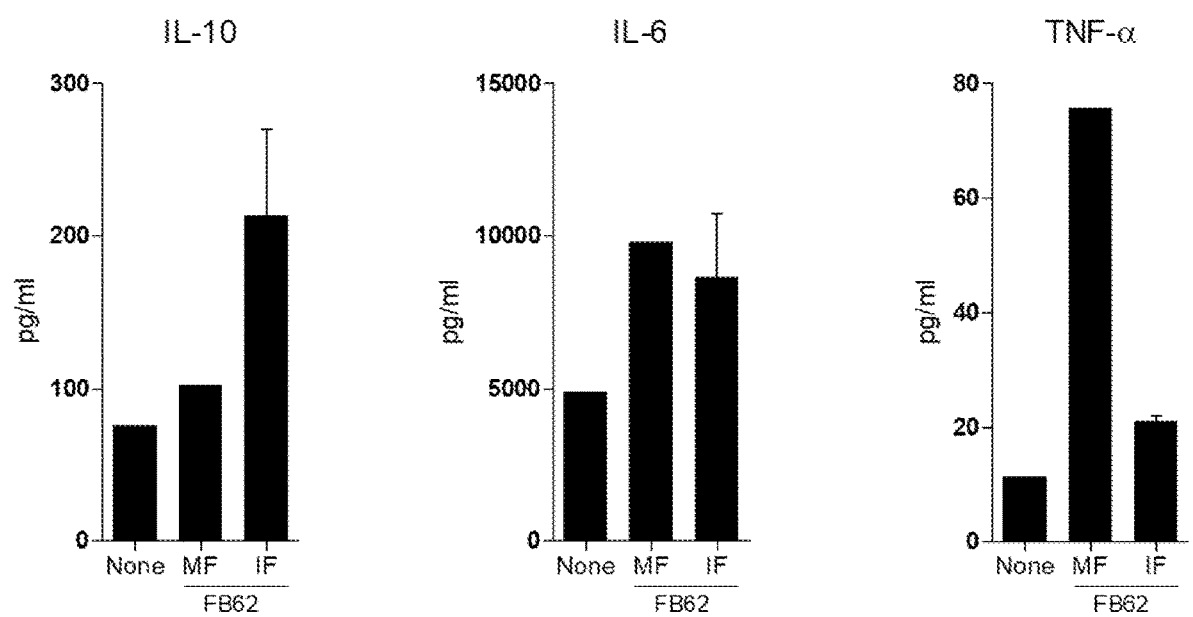

FIG. 8 Mouse colon tissues were infected with *Salmonella* SL1344 (MOI 1:1) and treated with ImmunoFOS® or the control containing maltodextrins and FOS in an ex-vivo organ culture model for 1 hour. After that, the medium was removed from the inside of the cylinder and the tissue was transferred to an oxygen chamber. Concentrations of IL-10, IL-6 and TNF-α as determined by CBA BD Array (BD bioscience).

FIG. 9 Mice were pre-treated with different doses of ImmunoFOS® (135-1.35 mg/kg) or its control, containing Maltodextrins and FOS, during 4 days. After that, mice were injected intraperitoneally with 200 µg of LPS. After 5 h, the mice were sacrificed and levels of different cytokines (il-12p70, IL-12p40, IFN-γ, IL-10, TNF-α and IL-6) were determined by CBA BD Array (BD bioscience).

Figure 10:
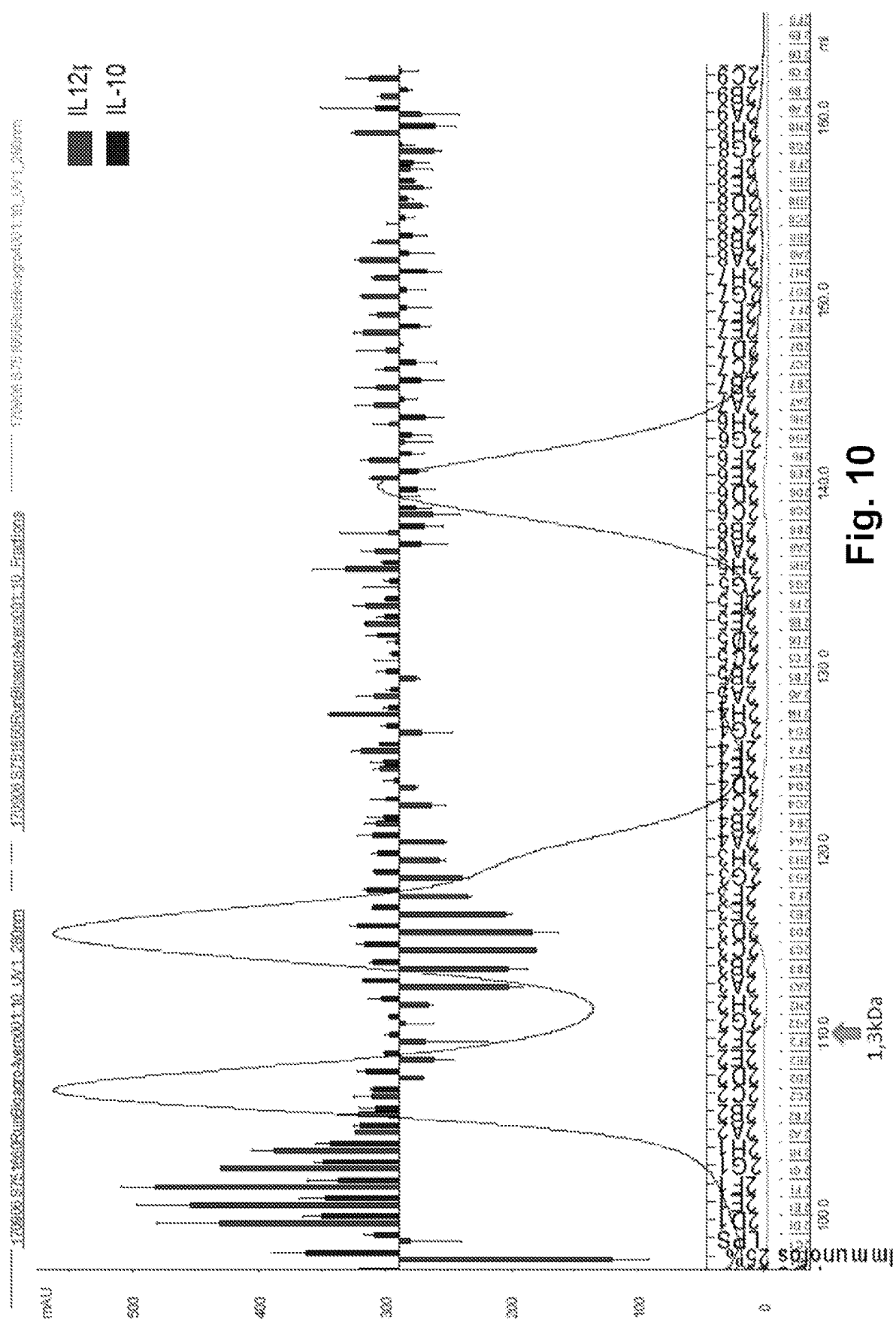

FIG. 10 PBMCs were treated with LPS (100 ng/ml) and with different fractions of ImmunoFOS® or fractions of the control containing maltodextrins and FOS for 24 h. Concentrations of IL-10 and IL-12p40 as determined by ELISA.

Figure 11:
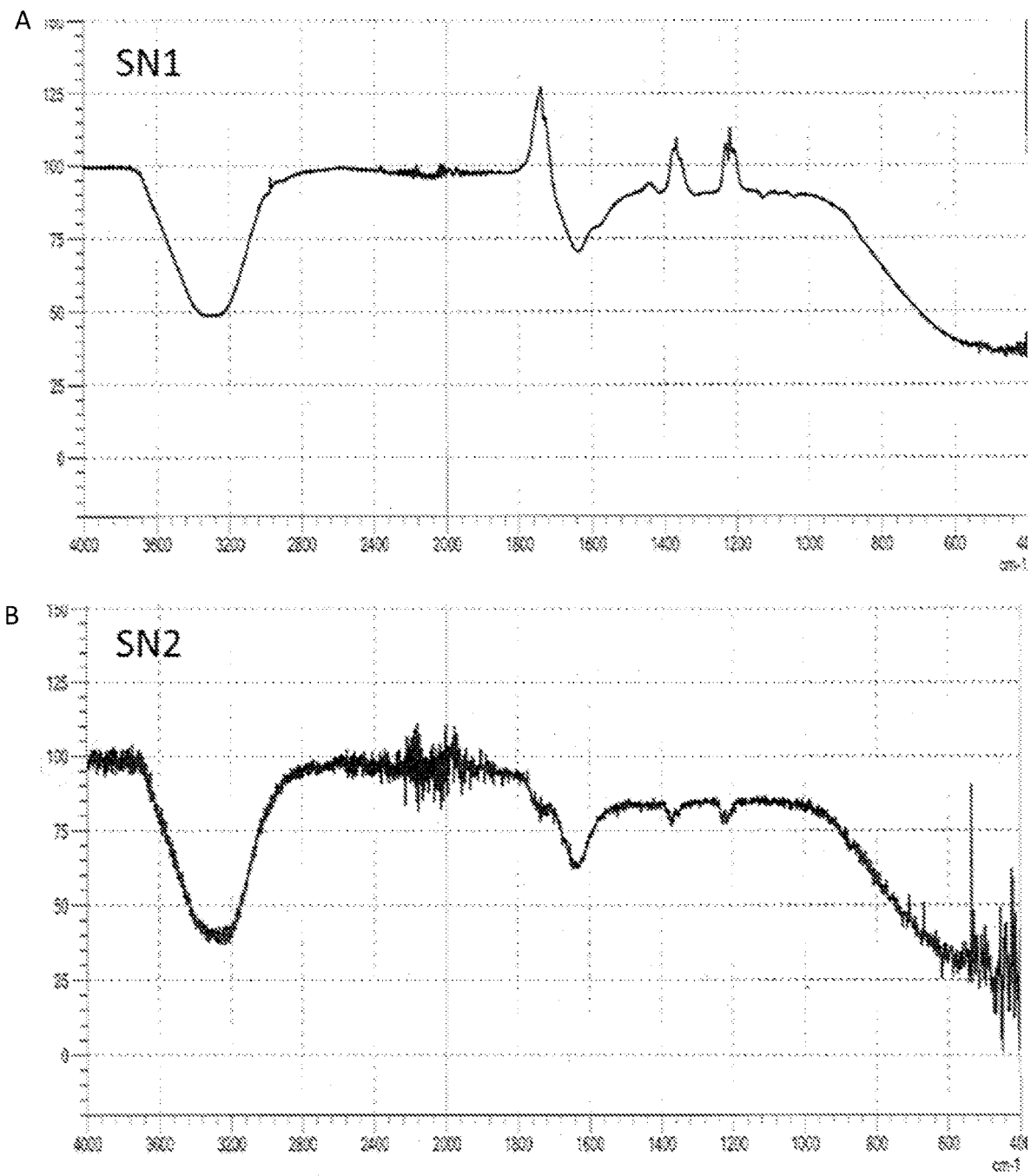

FIG. 11 FT-IR profile FT-IR analysis spectra of the fermented product supernatant of *Lactobacillus paracasei* strain CNCM I-5220 obtained from (A) first fermentation (SN1) and (B) second fermentation (SN2) process.

Figure 12:
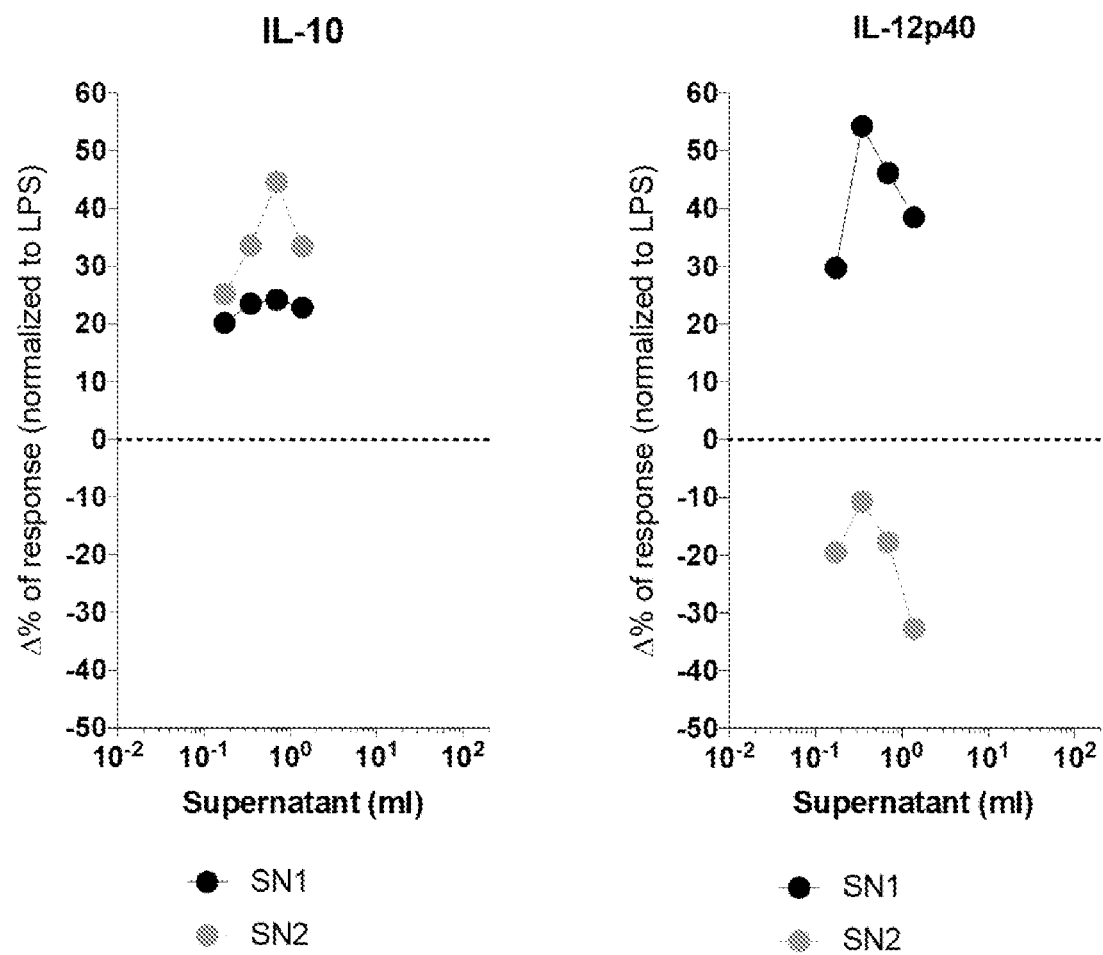

FIG. 12 PBMCs were stimulated with LPS (100 ng/ml) and treated with SN1 (supernatant of first fermentation) or its control (broth medium), or SN2 (supernatant of second fermentation) or its control PBS for 24 h. Concentration of IL-10 and IL-12p40 was determined by ELISA. The delta % of response (normalized to LPS) was calculated as the net effect of each fermented product versus the relative control medium.

Figure 13:
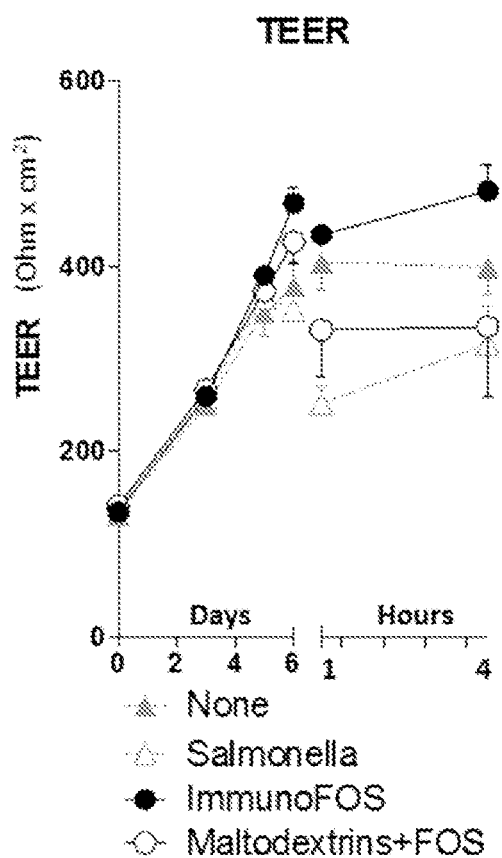

FIG. 13 Caco-2 cells were treated overnight with 5 mg of ImmunoFOS® and the relative control, containing Maltodextrins and FOS. After that, the cells were stimulated with *Salmonella typhimurium* SL1344 ($6 \times 10^8$ CFU/well) for 1 h and 30'. Then, *Salmonella typhimurium* was removed and the compounds replaced for next 4 hours. Trans-epithelial resistance was measured by chopstick electrodes.

Figure 14:
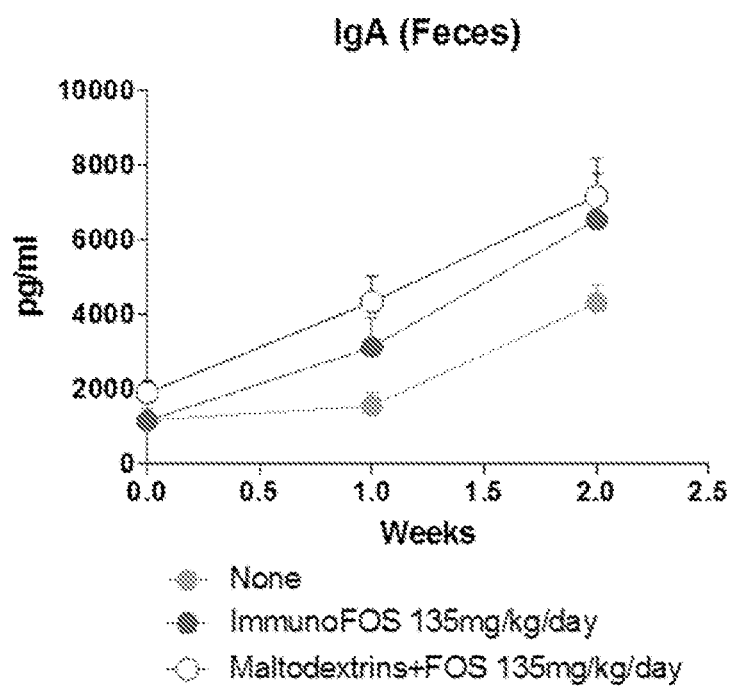

FIG. 14 Mice were treated for 2 weeks with 135 mg/kg/day of ImmunoFOS® or its control, containing Maltodextrins and FOS. IgA levels in feces were measured at time: 0, 1 week and 2 weeks by ELISA.

Figure 15:
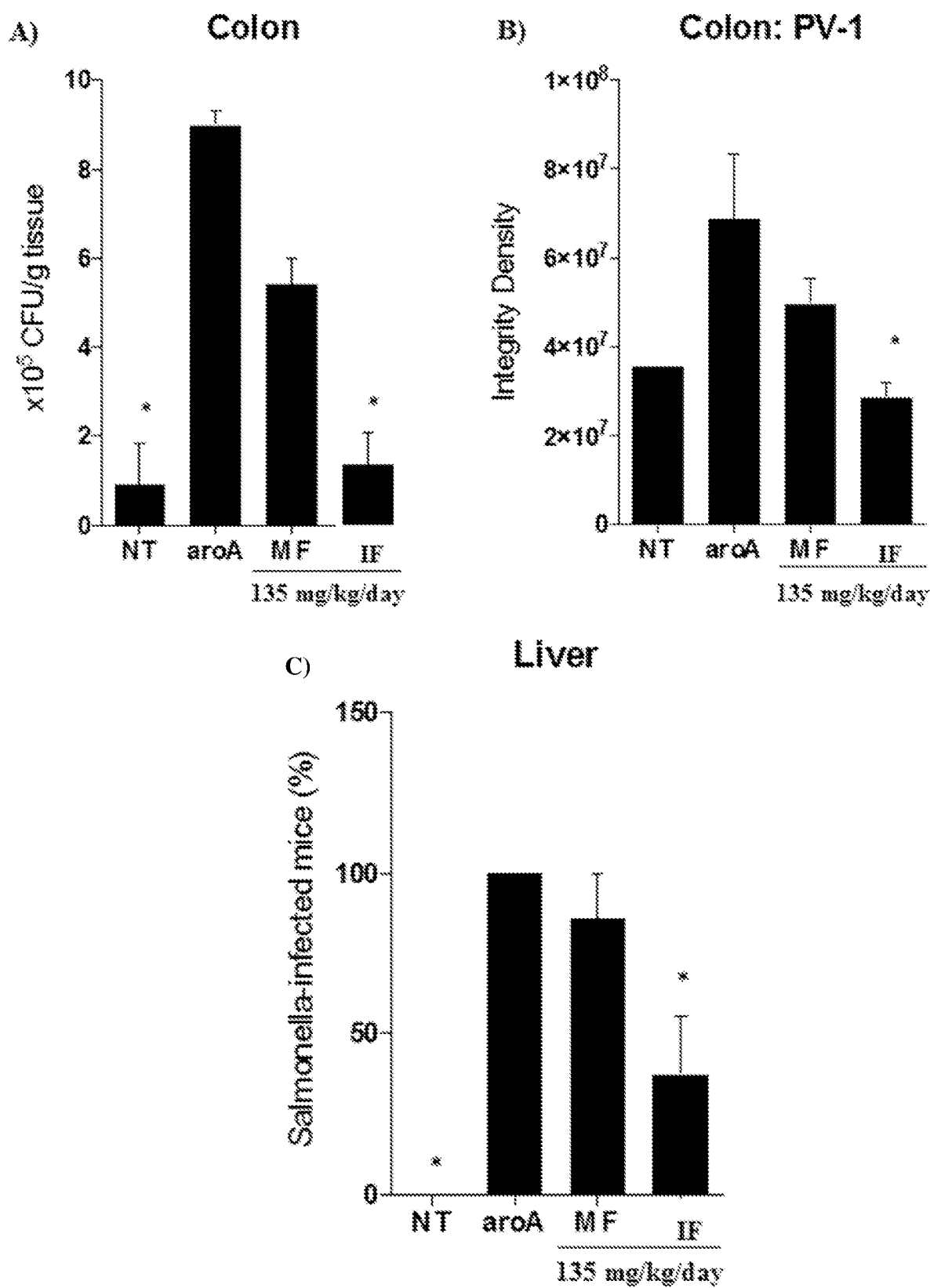

FIG. 15 Mice were pre-treated with 135 mg/kg/day of ImmunoFOS® or its control, containing Maltodextrins and FOS, for 10 days. Mice were then infected with 109 *Salmonella typhimurium* AaroA via oral gavage and after 6 h were sacrificed. Panel A refer to bacterial translocation to the colon (Statistical comparisons were performed using Kruskal-Wallis U Test. *p<0.05). All conditions were compared with AaroA group. Panel B refer to *Salmonella* dissemination to the liver and panel C show the mean fluorescence intensity of PV-1 quantified as up-regulation of the protein in the intestinal vessel. AU arbitrary units. Statistical comparisons were based used Mann-Whitney U Test. *p<0.05. All conditions were compared with AaroA group.

EXAMPLES

Material and Methods
Bacteria Culture

*Lactobacillus paracasei* strain CNCM I-5220 supernatants were obtained growing bacteria to OD600=0.6 in MRS and suspending the biomass in a saline solution supplemented with 5 g/L Fructooligosaccharides (FOS) (Immuno-FOS®). The resulting medium was then centrifuged 3500 rpm for 10 minutes and the biomass eliminated and then, in some cases, filtered with a 0.22 µm pore size hydrophilic Polyethersulfone (PES) membrane.

The fermented product supernatant was lyophilized by adding the cryopreservative Maltodextrins.

*Salmonella* serovar *typhimurium*, strain FB62, was grown in 3 mL of Luria-Bertani broth and cultured aerobically (in agitation) and used for stimulation at the exponential growth phase, namely when OD was 0.6 as measured with an Eppendorf biophotometer.

Preparation of Fermented Product

An inoculum of *L. paracasei* CNCM I-5220 is grown at a temperature of about 37° C. and is then gently stirred to avoid oxygenation of the culture medium, as MRS medium. The biomass is then allowed to grow for about 12 to 36 hours, preferably for about 24 hours, until the desired concentration of lactobacilli is reached, preferably a concentration of at least $5 \times 10^{10}$ CFU/ml. Then, the culture is centrifuged 3500 rpm for 10 minutes to separate the bacteria from the culture medium supernatant, the former being further processed as below for the preparation of the fermented product containing *L. paracasei* CNCM I-5220 postbiotic.

Centrifuged bacteria are transferred to a minimum isotonic or hypotonic solution (saline, phosphate buffer, H2O, etc.) additioned or not with prebiotic fibers such as nondigestible oligosaccharides (NDOs), resistant starch, pectin, beta-glucans, inulin, lactulose, polydextose, isomaltooligosaccharides (IMO), xylooligosaccahrides (XOS), lactitol, chicory root inulin-derived (FOS), wheat bran-derived arabinoxylooligosaccharides (AXOS), xylooligosaccharides (XOS), mannitol, maltodextrin, raffinose, lactulose, sorbitol, galactooligosaccharides (GOS) preferentially fructooligosaccharides (FOS) at 5 gr/liter and allowed to ferment for 12 to 36 hours, at 37° C. preferably for about 24 hours. Then the fermented broth is centrifuged 3500 rpm for 10 minutes to separate bacteria from the solution supernatant (fermented product) containing *L. paracasei* CNCM I-5220 postbiotic and heated at 90° C. for 10 minutes to inactivate any contaminating bacteria. The latter is used as liquid solution or preferably lyophilized powder in the preparation of the composition of the invention. For example, FOS fermentation by *Lactobacillus paracasei* strain CNCM I-5220, ImmunoFOS®, is used for food supplement for adult preferentially in neonatal food supplement formulation, and consists of ImmunoFOS®, diluted to 0.02% w/v, preferably 20% w/v, more preferably 4% w/v, in a saline solution or other diluent suitable for the purpose. The dilution depends also from the bacteria concentrations obtained according to the above paragraph. FIG. 1 shows a mass spectrometric profile obtained by surface-activated chemical ionization (SACI) technique [Cristoni S, Rubini S, Bernardi L R. Mass Spectrom Rev. 2007 September-October; 26 (5): 645-56.] of laboratory scale of *L. paracasei* CNCM I-5220 postbiotic (without maltodextrins). FIG. 2 shows HPAEC-PAD analysis profile of FOS as reference (panel A) and ImmunoFOS® (panel B), (FOS fermentation by *Lactobacillus paracasei* strain CNCM I-5220) with maltodextrins.

LC/MS Analysis

Mass spectrometry profile of supernatant of *Lactobacillus paracasei* strain CNCM I-5220 without the addition of maltodextrins was obtained by Surface-activated chemical ionization (SACI) technique (J Mass Spectrom. 2005 December; 40(12):1550-7.). Supernatant from *Lactobacillus paracasei* strain CNCM I-5220 were treated as follow. Lyophilized supernatant was diluted in PBS buffer and 5 ul were loaded on HPLC Ultimate 3000 (Dionex) equipped with Phenomenex Luna C18 (2.0×50 mm—particle size 3 µm) column coupled with HCT Ultra (Bruker) spectrophotometer.

Size Exclusion Chromatography Fractionation

ImmunoFOS (with maltodextrins) was resuspended in apirogen water and fractions were obtained by size exclusion chromatography technique using Fraction Collector Frac-950 (GE Healthcare) and HI LOAD SUPERDEX 16/600 75 pg column (GE Healthcare/VWR).

Lyophilized ImmunoFOS was diluted in endotoxin-free water and directly loaded on Superdex 16/600 75 pg 0.20 mM hepes ph 7.5+150 mM NaCl was used as gel filtration buffer. Recovered fractions were aliquoted and frozen for further analysis.

HPAEC-PAD (High Performance Anion Exchange Chromatography with Pulsed Amperometric Detection) Analysis HPAEC-PAD analysis profile of ImmunoFOS (FOS fermentation by *Lactobacillus paracasei* strain CNCM I-5220) was obtained as follows. Chromatography was carried out on a Dionex equipped with CarboPac PA-100 4×250 mm column (temperature set to 30°) and electrochemical detector for pulsed amperometric detection (Dionex/Thermo Fisher Scientific, Idstein, Germany)

Lyophilized ImmunoFos was diluted in endotoxin-free water and 10 ul were injected.

Constant concentrations of sodium hydroxide and various sodium acetate gradients were used over a period of 20 min. The final eluent composition was kept constant for additional 10 min.

Monocyte-Derived Dendritic Cell (MoDC) Differentiation and Stimulation Conditions DCs were derived from human peripheral blood monocytes obtained from healthy donors (Abbiategrasso hospital, Italy) having signed an informed consent for research use and selected with anti-CD14 antibodies coupled to magnetic beads (Miltenyi, Bologna, Italy). CD14+ cells were incubated for 6 days in complete medium containing granulocyte-macrophage colony stimulating factor (GM-CSF, 5 ng/mL; BD Biosciences) and interleukin-4 (2.5 ng/mL; BD Biosciences) in order to obtain immature MoDCs. MoDCs were incubated with Lipopolysaccharides (LPS) from *Escherichia coli* 0111:B4 (Sigma-Aldrich) or *Salmonella* FB62 (MOI 1:1 bacteria:DC) in the presence or absence of ImmunoFOS® or the control containing Maltodextrins and FOS for 24 h. Supernatants were tested for cytokine abundance by ELISA (R&D systems). Furthermore, the cells were collected and antibodies for CD80, CD83 and HLA-DR (Miltenyi, Bologna, Italy) were used to detect the surface makers of moDCs-activation using flow cytometry.

Peripheral Blood Mononuclear (PBMC) Cells and Stimulation Conditions

Buffy coats were obtained from healthy donors having signed an informed consent for research use. PBMC were separated with Ficoll (GE Healthcare) gradient centrifugation and then resuspended and cultured in RPMI 1640 medium (Lonza) containing 10% fetal bovine serum (Gibco), 1% Glutamine, 1% pyruvate, 1% non essential AA and 1% Penicillin-Streptomycin. PBMCs were incubated with Lipopolysaccharides (LPS) from *Escherichia coli* 0111:B4 (Sigma-Aldrich) in the presence or absence of ImmunoFOS® or the control containing Maltodextrins and FOS for 24 h. Supernatants were tested for cytokine abundance by ELISA (R&D systems).

Ex Vivo Organ Culture (EVOC)

C57BL/6J Mouse from Charles River laboratories France was sacrificed, the colon was removed and the clean mucosal layer was washed in Hank's Balanced Salt Solution buffer and cut with sterile scalpels into 1 $cm^2$ pieces. The pieces were placed on sterile metal grids and the cylinder (cloning cylinder, various sizes, BellCo, Modena, Italy) was attached with surgical glue (Vetbond, 3M, Milan, Italy) under sterile conditions with a pair of forceps. The culture medium was Dulbecco's Modified Eagle Medium supplemented with 15% freshly added fetal bovine serum, 1% Glutamine, epidermal growth factor (200 ng/ml, Peprotech, Milan, Italy) and Insulin-Transferrin-Selenium-X (10 µl/ml, Gibco, Monza, Italy). 1 ml of complete medium was dispensed in the centre well of the plate (Falcon, centre-well organ culture dish). Stimulation was performed with $1 \times 10^7$ colony forming units (CFU)/cylinder *Salmonella typhimurium* in 200 µl medium with or without ImmunoFOS® or the control containing Maltodextrins and FOS (10%). After 2 h at 37° C. in a 5% carbon dioxide incubator, the medium was removed from the inside of the cylinder and the tissue was transferred to the oxygen chamber. The chamber was filled with pressurized oxygen (VitalAire, Milan, Italy) and placed at 37° C. for the remaining 22 h of culture.

LPS-Induced Endotoxic Shock

C57BL/6J mice were purchased from Charles River laboratories France. All mice were maintained in microisolator cages in a specific pathogen-free animal facility. All experiments were performed in accordance with the guidelines established in the Principles of Laboratory Animal Care (directive 86/609/EEC) and approved by the Italian Ministry of Health.

Mice were treated orally with 135 mg/kg/day; 13.5 mg/kg/day and 1.35 mg/kg/day; of ImmunoFOS® lyophilized (supernatant of fermented FOS by *Lactobacillus paracasei* strain CNCM I-5220) at 96, 72, 24 and 2 hours, before LPS administration (n=5 per group). Control mice received Maltodextrins and FOS. LPS from *Escherichia coli* 0111:B4 (Sigma-Aldrich) was injected intraperitoneally (i.p.) at 200 µg per mouse in 200 µl of injectable water. After 5 hours mice were euthanized by exsanguination under anesthesia and blood was collected. IFN-γ, IL-10, IL-12p40, IL-6, TNF-α and IL-12p70 levels were detected in the serum by CBA BD Array (BD bioscience), according to manufacturer's instructions.

ImmunoFOS® Size Exclusion Chromatography

Size exclusion chromatography was performed using an HI LOAD SUPERDEX 16/600 75 pg (GE Healthcare/VWR) column and fractions were collected with a Fraction Collector Frac-950 (GE Healthcare)

ImmunoFOS® or control were directly loaded on Superdex column and 20 mM hepes ph 7.5+150 mM NaCl was used as gel filtration buffer. Collected fractions were aliquoted and frozen for further analysis.

FT-IR Analysis

Supernatant obtained from fermentation processes (SN1 and SN2) have been analyzed by Fourier transform infrared (FT-IR) technique by IRAffinity-1/1S (Shimadzu) instrument. The mid-infrared range of 4000-400 wavelength/$cm^2$ is used to excite atoms in molecular bonds, causing them to vibrate. A spectrum can be measured and calculated by light absorption.

Fatty Acid Analysis by GC/MS 250 ml of samples were lyophilized and suspended in 500 µL. Trans-esterification was carrying out by adding 850 µL of chloroform, 150 µL of H2SO4 and 1 mL of methanol. Thus, samples were heated at 100° C. overnight and to stop the reaction and eliminate water 2 mL of a 100 mg/mL sodium bicarbonate solution and 1 g of 99% bicarbonate were added. Subsequently, fatty acids were extracted using chloroform. 1 ul of the extract was analyzed in GC MS using a C18 30 m column. The fragmentation spectrum interpretation was performed by comparison with theoretical spectra in the NIST database. The area of the peaks was interpolated with a calibrator (FAME, Sigma Aldrich) to perform a quantitative analysis.

Peptide Analysis by MALDI-TOF 200 ml of samples were lyophilized and suspended in 4 mL of 1% formic acid. 1 mL of concentrated samples were analyzed by HPLC-UV on RP C18 column using 0.1% formic acid (eluent A) and acetonitrile containing 0.1% formic acid (eluent B) as eluents (flow rate 0.5 mL/min; absorption wavelength 220 nm). Fractions were collected and analyzed by MALDI TOF mass spectrometry in positive ion mode, using α-Cyano-4-hydroxycinnamic acid as matrix. Signals of interest underwent to tandem mass spectrometry analysis using MALDI TOF/TOF. The fragmentation spectra were collected and interpreted. The peptide sequences confirmed by alignment with the BLAST program Peripheral Blood Mononuclear (PBMC) Cells and Stimulation Conditions Buffy coats were obtained from healthy donors having signed informed consent for research use. PBMC were separated with Ficoll (GE Healthcare) gradient centrifugation and then resuspended and cultured in RPMI 1640 medium (Lonza) containing 10% fetal bovine serum (Gibco), 1% Glutamine, 1% pyruvate, 1% non-essential AA and 1% Penicillin-Streptomycin. PBMCs were incubated with Lipopolysaccharides (LPS) from *Escherichia coli* 0111:B4 (Sigma-Aldrich) in the presence or absence of supernatant of first fermentation (SN1) or Supernatant of second fermentation (SN2) for 24 h. Supernatants were tested for cytokine abundance by ELISA (R&D systems). The delta of normalized response to LPS of each fermented product was calculated by subtracting the effect of the media of fermentation (broth medium in case of SN1, PBS in case of SN2) from effect obtained by treatment with SN1 or SN2.

Stimulation of Human Epithelial Cells in the Presence or Absence of ImmunoFOS®

Caco-2 cells (human epithelial colorectal adenocarcinoma cells) were maintained in DMEM supplemented with 10% FBS, 1% Glutamine, 1% Penicillin-Streptomycin. Experiments were performed seeding $6 \times 10^4$ cells/well on polycarbonate membranes (Transwell 6.5 mm in diameter, 5 μm pore size) (Costar Corp). Caco-2 cells growth were monitored by measuring the trans-epithelial electrical resistance (TEER) until confluence by chopstick electrodes (Millicell-ERS, Millipore). TEER is a widely accepted quantitative technique to measure the integrity of tight junction dynamics in cell culture models of epithelial monolayers. 5 mg of lyophilized ImmunoFOS® and the relative control, containing Maltodextrins and FOS, overnight. After that, the cells were stimulated with *Salmonella* SL1344 ($6 \times 10^8$ CFU/well) for 1 h and 30'. Then, *Salmonella* was removed and the compounds replaced for next 4 hours. Trans-epithelial resistance was measured to evaluate the integrity of the monolayer at endpoint.

In Vivo Experiments

C57BL/6J mice were purchased from Charles River Laboratories France. All mice were maintained in microisolator cages in a specific pathogen-free animal facility. All experiments were performed in accordance with the guidelines established in the 5 Principles of Laboratory Animal Care (directive 86/609/EEC) and approved by the Italian Ministry of Health.

Fecal IgA Analysis

Mice were treated orally with 135 mg/kg/day of lyophilized ImmunoFOS® (supernatant of fermented FOS by *Lactobacillus paracasei* strain CNCM I-5220) during 2 weeks (n=5 per group). Control mice received Maltodextrins and FOS. Feces were collected at different time points: t=0, 1 week and 2 weeks. IgA level was detected in feces by ELISA.

*Salmonella* Infection

Mice were treated orally with 135 mg/kg/day of lyophilized ImmunoFOS® (supernatant of fermented FOS by *Lactobacillus paracasei* strain CNCM I-5220) during 10 days (n=8 per group). Control mice received Maltodextrins and FOS. After pre-treatment, mice were infected with $10^9$ *Salmonella thyphimurium* AaroA via oral gavage and after 6 h were sacrificed. Colon was aseptically removed and incubated 30' at 37° C. with gentamycin to kill external bacteria. Then, colon was digested with 1 mg/ml Collagenase D (Roche) for 30' at 37° C. Cells from colon were lysed with 0.5% sodium-deoxycholate and plated on Columbia agar with sheep blood (Oxoid) to evaluate bacterial dissemination after overnight culture. Moreover, also livers were aseptically removed and smashed to obtain cells that were lysed, as described above, and plated on Rainbow™ (Biolog) agar plate to evaluate *Salmonella* translocation dissemination after overnight culture.

Immunofluorescence and Confocal Microscopy

Colon samples were fixed overnight in paraformaldehyde, L-Lysine pH 7.4 and NaIO4 (PLP Buffer). They were then washed, dehydrated in 20% sucrose overnight and included in OCT compound (Sakura). 8 μm cryosections were rehydrated, blocked with 0.1M Tris-HCl pH 7.4, 2% FBS, 0.3% Triton X-100 a stained with following antibodies: anti-mouse PV-1 (clone MECA32, BD Pharmigen), anti-mouse CD34 (clone RAM34, eBioscience). Slices were then incubated with the appropriate fluorophore-conjugated secondary antibody. Before imaging, nuclei were counterstained with 4',6-diamidin-2-fenilindolo (DAPI). Confocal microscopy analysis was performed by Leica TCS SP8 equipped with a motorised inverted DMI 6000B microscope. Violet (405 nm laser diode), Blue (488 nm argon laser), yellow (561 nm laser diode) and red (633 nm laser diode) laser line that have been used for excitation. Image J software package was used for image analysis and fluorescence quantification.

Results

Stimulation of Peripheral Blood Mononuclear Cells in the Presence or Absence of ImmunoFOS®

Peripheral blood mononuclear cells (PBMC) are a heterogenous cell population that includes myeloid as well as lymphoid immune cells. ImmunoFOS® was used to assess whether it could modulate the cytokine release in particular IL-12p40 and IL-10 by LPS-stimulated PBMC, mimicking innate immune activation. The inventors found that ImmunoFOS® led to a reduction of IL12-p40 and an increased secretion of IL-10 (FIG. 3). In addition, ImmunoFOS was, also, used to asses if it could control an adaptive immune response using PBMCs from two different donors in a reaction known as the mixed lymphocyte reaction (MLR). ImmunoFOS increased the amount of IL-10 by 3-fold and inhibited almost completely the IFN-γ production during the MLR (FIG. 4). Those results indicate that ImmunoFOS has immunomodulatory/anti-inflammatory proprieties characterized by the reduction of proinflammatory cytokines (IL-12p40 and IFN-γ) and increase of anti-inflammatory cytokine IL-10 controlling activation of both innate and adaptive immune system compartment.

Stimulation of Monocyte Derived Dendritic Cells in the Presence or Absence of ImmunoFOS®.

Dendritic cells (DCs) are professional antigen presenting cells involved in the establishment of an immune response. In response to inflammatory stimuli they become activated and according to the level of costimulatory molecules they express on the surface and the type of cytokines they produce, DCs can skew the T cell response towards different polarizations. For example, high level of IL12p70 induce the differentiantion of interferon-(IFN)-γ producing T helper (Th)1 T cells, while low level favor interleukin (IL)-4 producing Th2 T cells. By contrast, IL-10 release is important to induce IL-10 producing T regulatory cells that protect from inflammation and tissue damage generate by an uncontrol exagerate immune response.

In humans, the most studied DCs are the ones that are generated from monocytes: monocyte derived (Mo)DCs. The activation of MoDCs with bacterial derived lipopolysaccharide or *Salmonella Typhimurium*, drives DCs to increase expression of surface costimulatory molecules and produce both inflammatory (IL-12) and anti-inflammatory cytokines (IL10). The inventors found that ImmunoFOS® led to a reduction of costimulatory molecule CD80 and maturation marker CD83, maintaining high levels of HLA class II molecules, indicating a modulation of activation by the treatment with ImmunoFOS® (FIG. 5). In addition, the inventors found, surprisingly, that in response to LPS, ImmunoFOS® increased by 6-fold IL12p70 secretion and by 10-fold IL-10 secretion. In addition, DC were infected with a pathogenic bacterium such as *Salmonella* SL1344 (MOI 1:1) and treated with ImmunoFOS®. The inventors found that ImmunoFOS® led to an increase of IL-10 secretion and no change in IL12p70 production (FIG. 7).

These results indicate that ImmunoFOS® does not modify the ability of DC to respond to inflammatory stimuli and favor an anti-inflammatory protective immune response by increased secretion of the anti-inflammatory cytokine IL-10.

ImmunoFOS® is Protective Against *Salmonella* Infection in Ex Vivo Organ Culture Models Gastrointestinal tract infection is a relevant problem in both adults and children.

One of the major pathogens of the gastrointestinal tract is *Salmonella*. The inventors tested ImmunoFOS® protective proprieties against enteric pathogen *Salmonella* using a novel intestinal organ culture model system that allows to preserve tissue polarity and permit physiological stimulation. Murine colonic tissue was infected with *Salmonella* SL1344 (MOI 1:1), with or without ImmunoFOS®, and IL-10, IL-6 and TNF-α secretion was measured. The inventors found that ImmunoFOS® led to a marked reduction of TNF-α paralleled by a significant increase in IL-10 while no change in IL-6 secretion was detected compared to control (FIG. 8). These results confirm the capacity of Immuno-FOS® to modulate immune responses counteracting inflammation and favoring tissue protection.

In Vivo Administration of ImmunoFOS® Protects Mice from Endotoxic Shock.

Figure 9A:
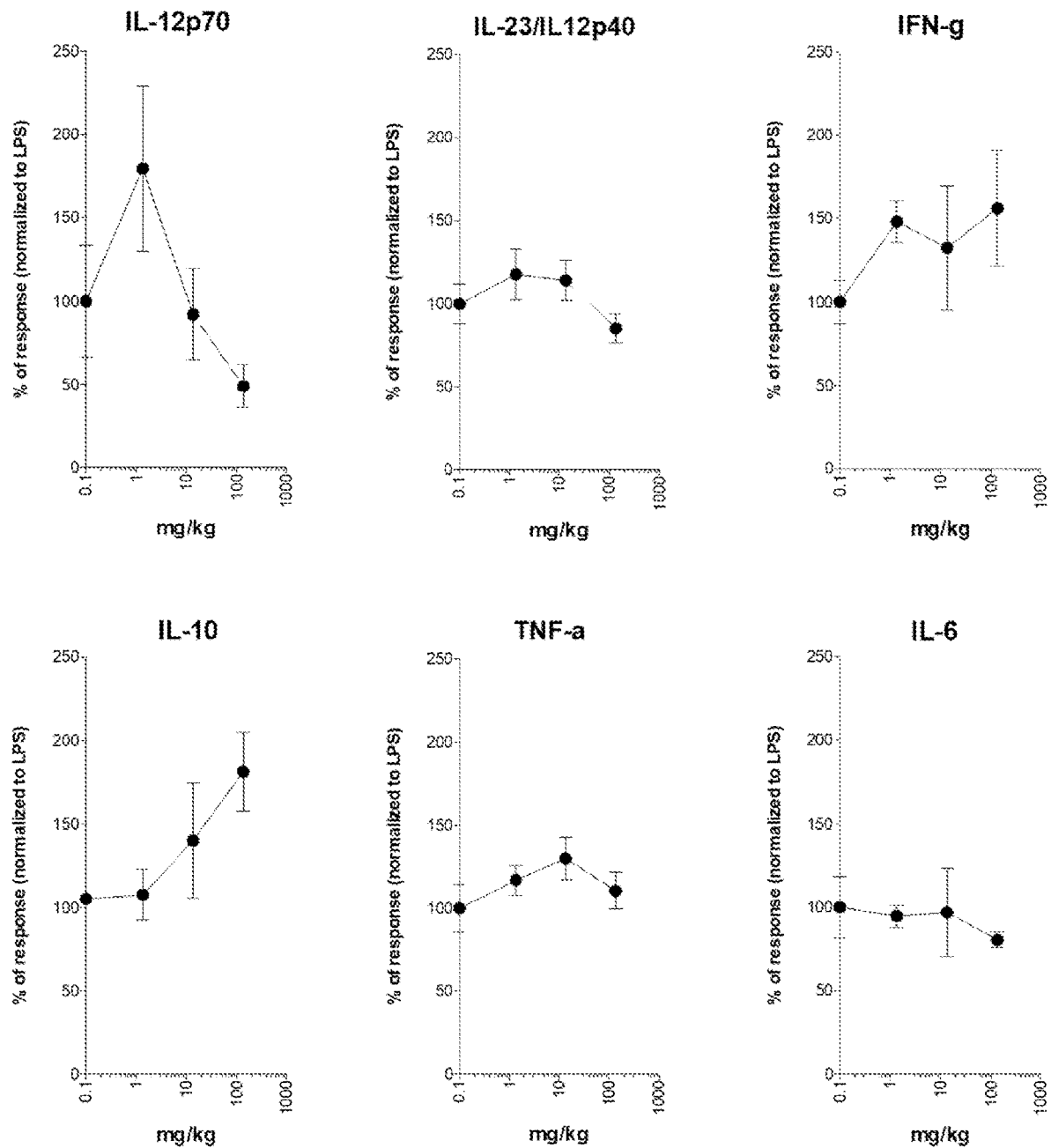
Figure 9B:
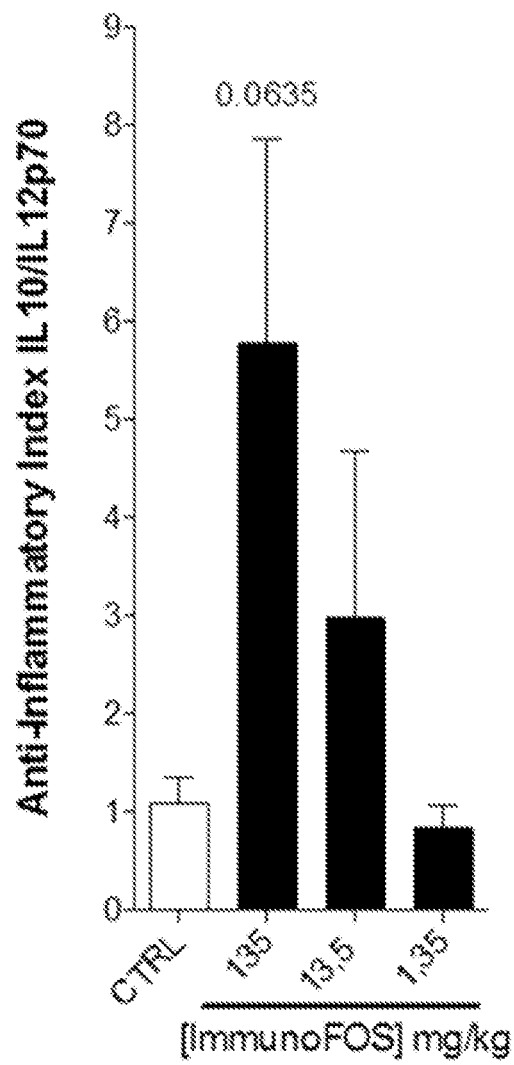

LPS administration in vivo in mice is known to be a valid animal model of septic shock. Sepsis is a clinical syndrome characterized by systemic inflammation (cytokine storm) and circulatory compromise initiated by an infection. The inventors found that ImmunoFOS® led to a dose dependent reduction of IL12p70 and IL12p40 serum levels that were paralleled by a significant increase of IL-10 serum levels while there were no major changes in IL-6, TNF-α and IFN-γ serum levels (FIG. 9a). As a net effect the anti-inflammatory index (IL12p70/IL10) of ImmunoFOS® increased in a dose depended manner (FIG. 9b). These results demonstrate that ImmunoFOS does not alter the overall activation of the immune system and protects from an overt inflammation by increasing systemic IL-10 production and reducing IL12p70 production.

Stimulation of Peripheral Blood Mononuclear Cells in the Presence or Absence of Size Exclusion Chromatography (SEC) Fraction Derived from ImmunoFOS®

ImmunoFOS® proprieties depend on metabolites released during the fermentation process described above. In order to profile and identify the metabolic components, ImmunoFOS® was fractionated by SEC. More than 40 fractions were obtained and each fraction was analyzed for its immunomodulatory properties on PBMC stimulated with LPS, and IL-12p40 and IL10 secretion was measured. The inventors found that ImmunoFOS® fractions had different immunomodulatory proprieties. In particular, fractions from 2D1 to 2H1 stimulated IL-12p40 and IL10 and conversely fractions from 2A3 to 2G3 reduced IL-12p40 and increased IL10 secretion by LPS stimulated PBMC, compared to control. These results define a functional signature profile of the immunomodulatory proprieties of ImmunoFOS®

Chemical and Functional Characterization of Fermented Processes Supernatant

The supernatant obtained from the first fermentation process (SN1) has been compared to supernatant obtained by second fermentation (SN2) by several techniques in order to characterize their composition and functional activities.

Fourier transform infrared (FT-IR) is a technique based on the absorption of infrared radiation by the sample analyzed. This technique detects the characteristic vibrations of the chemical bonds. The absorption spectrum obtained makes it possible to characterize the chemical composition of a complex sample. SN1 and SN2 were analyzed by FT-IR spectrometer. The inventors found that the FT-IR spectra (FIG. 11) differ between each other mainly in the infrared range of 1400-1200 wavelength/cm$^2$. These results suggest that the two supernatant may differ in term of qualitative biochemical composition.

In order to further characterize the supernatants chemically, a quantification of fatty acid was performed by Gas Chromatography with Mass Spectrometric Detection (GC/MS). The fermented product (supernatant/SN) derived from the first fermentation process (SN1) and from the second fermentation process (SN2) had a different fatty acid profile (Table 1). In particular, while in SN1 the inventors have identified several fatty acid molecules, in the SN2 fatty acid were not detectable. These results demonstrate that the composition of the two supernatants is different. Moreover, supernatants were analyzed for peptides content by MALDI-TOF technique. The inventors found that SN1 and SN2 had a different peptides profile. In particular, any signals have been detected by MALDI/TOF for SN1 compare to SN2 (Table 2a). In Table 2 panel B signals of interest from SN2 were profiled by MALDI TOF/TOF. These results further confirm that the components present into the two supernatants are different.

Peripheral blood mononuclear cells (PBMC) are a heterogeneous cell population that includes myeloid as well as lymphoid immune cells. Fermented products, SN1 and SN2, were used to assess whether it could modulate the cytokine release in particular IL-12p40 and IL-10 by LPS-stimulated PBMC, mimicking innate immune activation. The inventors found that SN1 (fermented product derived from first fermentation) and SN2 (fermented product derived from second fermentation) have different profiles. The net effect of each fermented product was calculated subtracting the effect of the media of fermentation, broth medium in case of SN1 and PBS in case of SN2 (FIG. 12). The inventors found that SN2 led to a reduction of IL12-p40 and an increased secretion of IL-10 (FIG. 12) better than SN1 product. Those results indicate that SN2 has immunomodulatory/anti-inflammatory proprieties characterized by the reduction of proinflammatory cytokine IL-12p40 and increase of anti-inflammatory cytokine IL-10 controlling activation of both innate and adaptive immune system compartment.

The Effect of Postbiotic on Intestinal Barrier Integrity

Epithelial cells create a protective layer for both the outside and the inside cavities and lumen of the body. Epithelial cells are connected to each other via intercellular junctions and barrier integrity is essential for the physiological activities of the tissue. The tight junctions create fusion points between epithelial cells, that regulates diffusion and allows both of these cell layers to form semipermeable cellular barriers that separate apical (luminal) and basolateral (abluminal) sides in the body, controlling the transport processes to maintain homeostasis. The inventors have seeded Caco-2 (human colon adenocarcinoma cell line) in transwells and their growth was monitored by measuring the transepithelial electrical resistance (TEER). When the junctions are strong, it is more difficult for the current to pass between the cells, thus TEER is high; otherwise when junctions are compromised the resistance is lower. The inventors tested the Postbiotic protective properties against enteric pathogen $Salmonella$ on monolayer of Caco-2 cells on transwells. The cells were incubated overnight with 5 mg of ImmunoFOS® or its control containing maltodextrins and FOS. After that, the cells were stimulated with $Salmonella$ SL1344 ($6\times10^8$ CFU/well) for 1 h and 30'. Then, $Salmonella$ was removed and the compounds replaced for next 4 hours. The stimulation of Caco-2 cells with $Salmonella$ $typhimurium$ causes a monolayer breakage thus registering low values of TEER. The inventors found that ImmunoFOS® was able to protect the monolayer from the damage caused by $Salmonella$ (FIG. 13) recording a high value of the TEER, that was similar to the unstimulated cells suggesting the ability of ImmunoFOS® to preserve the intestinal barrier integrity.

Effects of ImmunoFOS® on IgA Production in Steady State

Secretory immunoglobulin (sIg)A are a major component of the epithelial barrier and play a pivotal role in maintaining intestinal homeostasis. Several functions have been attributed to IgAs, but the major one is that of immune exclusion. IgAs bind to microbial components and affect the invasive potential of microorganisms by inhibiting their interaction with epithelial cells and their subsequent internalization. On the other hand, IgAs allow bacteria to attach to the mucus that they use as an energy source. Mice were treated orally with 135 mg/kg/day of ImmunoFOS® (supernatant of fermented FOS by $Lactobacillus$ $paracasei$ strain CNCM I-5220) during 2 weeks (n=5 per group). Control mice received Maltodextrins and FOS. Feces were collected at different time points: t=0, 1 week and 2 weeks and IgA levels were detected in feces by ELISA. The results revealed that ImmunoFOS® increased fecal IgA levels similarly to FOS administration in healthy animals (FIG. 14). These data suggest thus that ImmunoFOS®, which does not contain FOS, protects mucosal surfaces from pathogenic infection.

Effects of ImmunoFOS® in $Salmonella$-Infected Mice

The intestinal barrier plays a key role in health and disease by limiting systemic dissemination of microbes and toxins but granting to nutrients to access the circulation. Some harmful bacteria, however, can reach the liver and activate an immune system response, causing an infection. The gut vascular barrier (GVB) acts as a screen against bacteria when they pass the epithelium. This vascular barrier thus prevents access of the microbiota to the liver and controls the transfer of proteins and nutrients into the blood. The GVB can be evaded by aggressive bacteria, such as $Salmonella$ that has developed systems to break it and then spread in the body through the circulatory system. GVB is a functional barrier because Plasmalemma Vesicle Associated Protein-1 (PV1, encoded by the plvap gene), marker of endothelial barriers, is expressed at low levels at steady state. PV1 is a transmembrane glycoprotein that has been localized to caveolae and trans-endothelial channels of systemic fenestrated capillaries where it regulates vascular permeability.

Mice were treated orally with 135 mg/kg/day of ImmunoFOS® (supernatant of fermented FOS by $Lactobacillus$ $paracasei$ strain CNCM I-5220) during 10 days (n=8 per group). Control mice received Maltodextrins and FOS. After pre-treatment, mice were infected with $10^9$ $Salmonella$ $thyphimurium$ AaroA via oral gavage. The inventors have found that after 6 hours of $Salmonella$ infection there was an increase of bacterial dissemination in the colon (FIG. 15A). Conversely, ImmunoFOS®-treated mice did not show major bacteria dissemination in the colon (FIG. 15A). These results highlight the role of ImmunoFOS® in the maintenance of gut epithelial barrier integrity controlling colon bacteria load. In addition, endothelial colonic PV-1 expression was markedly up-regulated in $Salmonella$-infected mice. Conversely, no increased of PV1 expression has been observed in ImmunoFOS-treated mice (FIG. 15B). Thus, ImmunoFOS® treatment significantly reduce $Salmonella$ translocation to the liver compared to the control group (FIG. 15C). These results demonstrate that ImmunoFOS®, but not FOS control vessel endothelial permeability reducing systemic $Salmonella$ dissemination. These data confirm that ImmunoFOS® has different properties compared to FOS also in vivo.

Sequences

Included in the present invention are also nucleic acid sequences derived from the nucleotide sequences shown below, e.g. functional fragments, mutants, derivatives, analogues, and sequences having a % of identity of at least 70% with the below sequences.

In the following are disclosed five gene sequences, representing specific core genes of $L.$ $paracasei$ and $L.$ $casei$ species.

```
                                         SEQ ID NO: 1
ATGAATCAAAAAGCTTTGAATCAATTTCCTGAACTTACCTACACAGAAC

AAGTGTCGGTTGTTGGCGGCGATTTGTCAGTCGAAGTCATCATGAAAGG

TATCTTCACCGGTATCTTTGATGCTGGGTACCAAGTGGGTCAGTCAATC

GCAAAATGGGTTAAGTAA
                                         SEQ ID NO: 2
ATGAAAGGTAAGCGGCAGCACTTACTTTTATATTTTGTTCTGGGTATGA

TGACAGGACTGGTGACGGCAGCGATTTTTCATATCATTTATGCCTGGCT

TTTTCATTGA
                                         SEQ ID NO: 3
ATGCCCAAAAGGGTCGATCAACATATACGTTCACGCCTTAAAGGCTTTA

CTTTAATTGAAGTGGTGGTCAGCCTGATTTTACTTGCGGCGGTCATGCT
```

```
GTTATGGCGACCGGTTTTATTGCATGTCACGCGGTTCACGCTTCAAGAC

CATGTGCTAATCACGTCATTGCAAGCAGAGCATGACTTGCAAATGTTTG

TACGAGATAAAAAGTTGCGGTCTGTGGCCTTAATGTCGGTAAGGGTGAG

AAGTCCCGAGAAAGCTTACACGATCAATTTTTATCAGACCAAACATTTT

CGCGGTATGGTTCGTGTGATGGGATCTGAAAATGGGCATATGCCATTAT

TTACGCATCTAACCGGTGTCAATTTTAGCAAGGTAGCTCAAGGCTTTCG

CTATCGTCTGTATTTGACGACTTCGCAGAAGATTGACGGTGGGGTGCAA

ATCGATGAAGATACGCGGTAG
```

SEQ ID NO: 4
```
ATGGCCGCTGATTTCACCCAATTACAACAAGCCATTCGCTTGCTCAATG

CCCATACTCGAGCTGCTGATGAGCAAGCGTGGCAAGTGCTTTTTGATCG

TTGGCTGGCAACTTTATCCTCTGAAACTCGCCGGCAAATGCAAACAGTT

CGGTTTAATCATGCCCAATTGACGTTACTCACAACGCTGGATCAAAGCA

GTCGCAAACAACTGCGCAATCAGGATTTAACCGCTGCTGTTCCGTTCTC

ACAAGGCCTAGTCTCACGCTATGTTGCTCGCCTTGTTCAATTAAACTTG
```

```
CTGACAAAATTATCCTTGCCCGACAATCGCAAGGCCTACATTGTTGCAC

TAACTCCGCTTGGTCAACAAGTCGCTGCCTTACATCAGCAAATGCATCA

TCACACAAATGCTCAACTCGCCTCTGTACTTCATACCCTTGATCCACAA

GATGTTCAAACTACCATTCAGGTACTCACAAAACTGACGGCTCAGCCTT

TACATCCCAAGTCTTAG
```

SEQ ID NO: 5
```
ATGGGCGGTGTCATTTGTTACGCGGTGCCGGTCTTTTGGAAAAGAATAC

TTCGCAGACACCTGATTCACGAGATTAAGACCCTGAATCAAGGATTGCA

GTTATCAAGCAAAGCCATGAGCCAATTAATTGATCCGGAAAATCCTTAT

ATGGTATTTGCTGATGAAAATGGTGAACTGGATTTTTCATTTTTGTGGC

TAGGCAACTTGCGTCAATTGAGGCGTGAACTGCGTCTAATTAAAGAACA

GAAAGCTAGGGTTTGA
```

In the following are disclosed unique sequences of L. paracasei B21060 with respect to the L. paracasei species publicly available in NCBI databases. SEQ ID NOs: 6 to 8 refers to gene sequences, whereas SEQ ID NOs: 9 to 18 refers to genome DNA sequences.

SEQ ID NO: 6:
```
ATGAGTAAATATAAAGTTATTATTTGGGGATTAGGAAACGTTGGTCGTTCCGCAGTGAGAATGAT

CGCGGAAAGACAAAATATTTTTGAATTGGTTGCAGCCGTTGACGTTGATCCAAAGAAGTTAGGTA

AGGATGCCGGAGAAGTCTTTGATTTTGACAAAGTCGGCGTCAAAGTTTCAGATGATATTGATGCA

GCCTTGAAACTTCCAGCTGACATTGTGCTCGACTTTTGCCCAACGGAAATGGACAAACAAGGAAC

ATTCATGCCTTCTGCTATTCGACTCGCCAAATCGCTCGATGCCGGTAAAAACGTTATTACCACGA

TTCCGGTATATCATGTTCAAGACAGTCAGCCAGAAGTATATGAATATCTAAATGAACATGCTAAAG

CACATAATGTTGCTTTTGTACCATTTGGACTTTTGCCAGGCGATTATGCCTCATATATCCCACTAG

TTTTGGCCGGGGCCATGGGCCACGTGGATAAAATTGTTGTTCAATCCGGTGAAGATGACTGGCA

CAACACATCAGGCTGGGTCGATGTCTTCTCATATGGCGGCGATATCAATAAATATCCAAAACCAG

ACTCAGACGAAGATCTCTTGGCTAAGTTCATTTATGCTTATTATTCATCCGGCGTATACGAGATGG

CCGATAGGATCGGTCTGAAATATGATACCTTCAAACCAGAGCATGAAGTCTTCACTGCACCCAAA

GATTTGGAAACGATCAAGGGTACAGTCAAAAAGGGCAGCATTTATGCCCACAGATTTACCATGGC

ACTTTACAACGGCMCGAACAAGTAGCCGCCTTAAGATATGTTCATAAAGTTGATAATAAAGAGA

CACCAGAATTACCGATCAATAATACGATTCATATTGAAGGCTTGCCGTCAGTCGATGCGCAGATC

GATGGATTGATCCCAGAAAGAGAAGGCTACGTTTCATCAGCCGCTCCAGCAGTCAACTTGATCC

CTAGCATTCTCGAGACCGACAAGACAGGTTATGTTGAAGTCTGCGACCTTCCAGTAGTGATTGCC

AGGCCATTGGATATTGGCGCAAAAAAATTAGTCTAG
```

SEQ ID NO: 7:
```
ATGGCAACCTATTCGCAGATAGAACTAGACATAATCAAATCATTTAAAGGGCTGATGAAAGACCA

TGAATTCACTGAGATCTCAATTAAAATGATCGCTGAAAAAGCCGATATCACTCGACGCGGCTTTTA

CAATCACTTCTTAGATAAATATGATCTTGTCAGTACCATCTTTGAGCATGATCTTTTTCCAACAGTC

ATCAGTTTGACGAATATCAATGACTGGGATCAAGGGTCGCTGTTTATCGTGAATTATCTCCAAGA

CAATCGCGACTACTATAAAAAATTGTTGTCGCTTGAAGGACAAAACTGTTTACAGACAGACTTTTA

TAAATTGACTGAGATGCAGATTGGGATCTTGATCCCAGAAATATTGGTCGGTAGGAAAATTTCTG
```

-continued

ACGAAGATCAGGCATTTTTAAGCGATTATTATTTTCACGCTTATATGGGACTGACTACCGAATGGG

TCAAAGGTAAATATGGTTTTTCAACTCAGGAGTTCGTTAAACGGTGGAAAGCCTTACTCAATAATT

CAATGCATAATTATCTGGACAACTACGCTCGATGA

SEQ ID NO: 8:
ATGAGTAAATATAAAGTTATTATTTGGGGATTAGGAAACGTTGGTCGTTCCGCAGTGAGAATGAT

CGCGGAAAGACAAAATATTTTTGAATTGGTTGCAGCCGTTGACGTTGATCCAAAGAAGTTAGGTA

AGGATGCCGGAGAAGTCTTTGATTTTGACAAAGTCGGCGTCAAAGTTTCAGATGATATTGATGCA

GCCTTGAAACTTCCAGCTGACATTGTGCTCGACTTTTGCCCAACGGAAATGGACAAACAAGGAAC

ATTCATGCCTTCTGCTATTCGACTCGCCAAATCGCTCGATGCCGGTAAAAACGTTATTACCACGA

TTCCGGTATATCATGTTCAAGACAGTCAGCCAGAAGTATATGAATATCTAAATGAACATGCTAAAG

CACATAATGTTGCTTTTGTACCATTTGGACTTTTGCCAGGCGATTATGCCTCATATATCCCACTAG

TTTTGGCCGGGGCCATGGGCCACGTGGATAAAATTGTTGTTCAATCCGGTGAAGATGACTGGCA

CAACACATCAGGCTGGGTCGATGTCTTCTCATATGGCGGCGATATCAATAAATATCCAAAACCAG

ACTCAGACGAAGATCTCTTGGCTAAGTTCATTTATGCTTATTATTCATCCGGCGTATACGAGATGG

CCGATAGGATCGGTCTGAAATATGATACCTTCAAACCAGAGCATGAAGTCTTCACTGCACCCAAA

GATTTGGAAACGATCAAGGGTACAGTCAAAAAGGGCAGCATTTATGCCCACAGATTTACCATGGC

ACTTTACAACGGCAACGAACAAGTAGCCGCCTTAAGATATGTTCATAAAGTTGATAATAAAGAGA

CACCAGAATTACCGATCAATAATACGATTCATATTGAAGGCTTGCCGTCAGTCGATGCGCAGATC

GATGGATTGATCCCAGAAAGAGAAGGCTACGTTTCATCAGCCGCTCCAGCAGTCAACTTGATCC

CTAGCATTCTCGAGACCGACAAGACAGGTTATGTTGAAGTCTGCGACCTTCCAGTAGTGATTGCC

AGGCCATTGGATATTGGCGCAAAAAAATTAGTCTAG

SEQ ID NO: 9 Position 102558..102986
AAAAACGGCTTAGAACGCTCATATTTGCGTTCTAAGCCGTTTTTATCAGCATAGGTTCTTGACACC

AATAAACATCTTTAGTAATTGATCAAATTTAGGCAATGTGCTTTTGTCGGTAATGGCGATAGCCC

TACCGAAGCTTCAGCTGAGGTTCTTCTGAGCCACGCAAGCGAAGCGCGCTAGGGCAAGCCAAC

GGCGCGCAGGCGAAGCCGGAGTTAAATGTGGCGCAGCCACACCTTTTAGGGAGCAACGCGAC

CAGAATTTTGTATGGGGTTTGGGAAGAGGTTCTCCCCAAGGTCTTTTGTGGTTATTAACAAGCAA

AACACAAACACAAGCCTCGCGCGCGTTATATATACTTCTAAATACTTTTAAATACTTTAAGTACTTA

GGGAGACGAGAATGGCTCAACCACGCGTTTAAATCGACT

SEQ ID NO: 10 Position 103624..103864
ACGACCTCTCGACCACCCACTGCCTCACCAATCCCCAGGTGAACCGGGCCAAGGGCACTACCG

AGCAACCCGACCCCTATATCCCGGTGGGCGTGGTGAAGCAGACCGATGGGGGCATCGTGGTGC

GGGGCGCGCGGATGCTCTCCACGCTGCCCACGGCGGATGAGCTTTTAGTCTTCCCCAGCACTT

TGCTCAAAGAAGGGCCGGGAGCCGACAAGTACGCCGTGGCCTTCGCCATCCC

SEQ ID NO: 11 Position 254291..261674
ATTGATCGCCTCCGGGTCACTTATATGTAACTAATAATACTCCCTTCTCTCTTTAGTTACAATAGG

GTACAGCCTATCGAATCACTTACGCTTCCACTTTGAGATAACTTTTCGTTATTATTTATCAACGGC

ATTAACGATATCATTAACTGTTTGCAATGCATCGCTCAGTACACTAATTGGTGCTTGTTCAATATA

CTGCATGTGTCGTTGTACAAAATCAAAGGTGTGAAATTGTAACGGATTCACGTACCCTTCTATTTT

TTCAGTCTGAATCGGTACCATCAAGCCTGTTTCAGCTAAGCGATTATGTTTGGCATGCGTGATCG

GACAAACCAACGCTAATCCAGTCATTTTGGCATATTGTTGATTGCTAATAACGAGCGCTGGTCGT

CTTTTTTTGAATTTCATGACCCCGACTTGGCATGAAATCAATACTCACAACATCACCTTTGCGTGGT

TGATAATGCCTAGTCCCACTCACTTGGTAATACCTCGTTTTCTAACGTAATATCTTGTTGGTGTAC

-continued

```
TTGTTGCTTGTACCAATCACCTTCAAATGGATTGCGGTGCTTCGGCAGATAAAGAATGCCACCAT

CATCACGTTGCTCAACTGTAAATTCAGTTCCATCGGCGATTTTAATACTCTTTGGAATGGTTAATG

TAATGGAATTGCCAACCCTTCTTGCTTTAACTGTCATTGAAATCATCCTTTCGTATACACCGAGTA

TACACCAGCGCGAATGAATCTGCAACTCTTGTGCCCTCTTGTGTACAAACACCACTGTCAATTTA

CTTTTGCCTATTGTGCTTTATCTCTTCTCGTTCTGTCATTAGTATGCCACCAACACGGCCGACTTC

ATCCGGCTCACCTTTGATGACGCCTTGAATACCATCGATTTGCTTCCAAGTCTTTACTTCCAAGTT

CTTCAAAGACTTTGATATCGTTTTTCGATGCCGGCAAACACTTCTTCATTCTGATGCCTTTCAAAG

AATTCCTCTAGATCATTCATCAGAGATTCTCCTCACTTAAACCTAGTTGGCGTCAAATTCCATCTC

AGCAATCGAATCTTCTAGGCTGTCCATTACTTCGTATGTTTCAATGAAGTTAACCCAGCTGTCATA

TGGATGTAGTTTGCTTTCTTTAATGCTAGTTCTAAGCTTTTCGTACACGTTGTCAATAAACTGCTCA

ACCATCCTATTAACCGCACTATTAATAACCGCTTCGTTCCACTGCTTAGATGCTGCACGCTTTCGA

TTTTGACTATGCTGATGGGACAGCGCCCGGCTTCTGAACAACGCTACTGCCCTGCTGTTAGCATT

CAGATAGGTTTCAAATTCTTCACGATCCATTACGTTTCCTCCTCAAAATAAGCCTCATTTCATAGC

ACAGCTTCAGCAAAAGGCATGTCATCCTACATGCCTTTTTTCTGTTGCTCTTCAATATCAGTATAA

AACGTCCTGCCGCTTTAGGCAAACGTATGTTCGCTATTAAGAACATACGTTTGTATAATAACTATA

AAAGATTTAAAGGAGGTCAATCGTATGGAAAACAATGTCCCGCGTGAAAAATGGCTTTACCCTGA

CCGCTGCATGAAGAAATGGCTGGGCTGGATTCTAAGCGACCATTCCGCCTATATGGAAGAAGCG

GCTATCTCAGAACAACCGGTGCTCCCAAAGCCTGAACAGACACAAGAAACCATTAATGGCGTACT

CGAAGATGCTTGGCAAAACTCAAAAATTGTCGCAGTTCAAATCGGTACGCCATACGATGATCTTC

TGTTACCGGATATTGAAGGCGCCGTGATTGGTCATTGGGACGCTCAGGTTTATCTACAGCTTAAA

ACTGGTGAGATGCAATCCATTAATGCAGCGGACATTCGCAATGTGCAACTGCTCAATCCAGATCG

GTGGTGGGCGTTAGTATGACGACACCATTAGATGATCCAACAAGGTTACCGGTACACGACATTAT

GTGCATTGACTGTAAGTCCTTTTACGCCTCAGTTGAAGCTATCAGACGCGGGATTCATCCGTTAG

CCGCCGACATTGCTGTTCTCAGCAAAGGTAATTCTCCTGGCGGTTTGGTGCTGGCTGCTAGTCC

CAACTGCAAAAAGCGTTACCACGTAGGACTGAGTACACGCCGTTTTCAGCTAAGGGACGATATG

TAGGTAGAACTTGCTGAACCGCGGATGGCTAATTACATTCGCAAGAATTACGGTATCAATCGTAT

TTACCGTCAGTTTACTGACGATGCTCACTGGTCTCCCTATTCCGTTGACGAGTCCTTTATTGACGT

TACCCACCCCCACAATCTCTTCGGTTCTAATGAAGAAATTGCTACCCAAATACAGAAGAAGGTGT

TTGATCAGTTTGGCATTGTCACAACAGTTGGCATTGGGCAAAATCCCCTATTGGCAAAATTAGCC

CTAGATAACGAGGCTAAGAAGTCAACGCCTTGGCAAGCCACTTGGACTTACGATCGTGTGCCAG

AAACAATATGGAAACTTGATGACTTGGTTGATTTTTGGTCGATTGGTAATCGAACTGCCAAGAAG

CTTAACGCGATTGGCCTTCATAATCTTTACGACTTGGCTCATGCAGACCGCGCCATTCTGCACCA

AAGATTCGGTGTTCTCGGTGATGCCATGTACTTTCACGCATGGGTATTGATTACTCAGACTTAA

CCCGCCGCTACTTACCACGGGCCGAAAATAAAGGCTACGGCAATAGTCAGGTACTCATGCGTGA

TTACACTCAGGCAAGGGAGATTGAAGTCATGCTTAGCGAGATTGCTGATCAAGTGGCTGGCCGA

ATTCGCCATCACCAAGTCCAAGGTGAGGTCATTAGCGTTGGCATTGGTTATGCTGATGCAGAAGA

AGCTGGCACCTCCGGTTTCGGTGCGCAAATGAAGATTGATCCCACAAATCGCACAGACGATTTA

ATTCGCGCTACTCGATTTCTCTTCCATAGTAAGTGGAACGGACACGCTGTTAGAAATGTCTCAGT

TCGCGTTAATCGCATCAGCCAAGCAAGTACAATGCAACTTAGTCTATTTGAATCAGCAGAGAAGG

AGGAAGCAAACGCGGCTCCTATGCTGTAATTACGGATAAAAGAATCACCATCATTAGGTTTTTCG
```

-continued
```
TCTAACAATTTTAGGAAACTTCACTTTCTAGGTCGTAACTTTATTTTTGCAATCTAGGGTTTTTAA
ATATATACATTTTAGCTCGTTTGTGTTTAATATTATAATCACAACTATACCAATGATAAATGTCTAAC
ATAAATATACAAACATGTTGACAGAAGCTCTTGAATACGTTTACAATTATTTCGTTCAGGCGAGCT
TTGTTTTTGAAAAAGTATTAATACAAGATAACTAGGTTAGTGGCTGTTGAATTAGGCCCCCGATTT
CGGGACCACGACAGTCACTTGATACTCGATTTTTATCGTTTGCTGGCTTGATCGTACATTGAACG
AAATTGGTACAGAAAAAAGAGCTAAGAGCCGCTCCAAATTAGCCAAAACGATTGCGGCGTCAATG
CTTACGGCGATCGTTTCTGCAGTTTTAGCTGTTACCAGATCAAGTCCTAGTTTCCCTTTGATGAAG
GCAAACTCACGCTCGATCTCACCTCGTCGATTTTCGGCTTGTCGGTCTGCCTTACGTTTGGCCG
GATCGACCTGCTTCGGCCGACGGCCCAATCTAGGACCGCTAAGTTTGATCCCAAGATCTGCGCA
CAGCCCGATATTCGCCCGAGTCCGATAAAGCGTATCAGCCAAGATCTCATCCGGGTATGTACCA
TACGTGTCAAAATAATGGTCGATCGTTGCTGGTAAGTCAGCACTTTCGTTAAACGCATTGAACGC
AAACCGTTCAACGCCACGACGCCATGACTGATCGATACGTCGATCTTGGGCCCGAATTCGACC
GGATCCTTTGCTTTGCCGCGAATGATCGGTCGGATCGCTGGTTGATCAAGGCTTACGATCCGAT
CCGCGACTCGGTGAGTGTGCTGTCGATACATTTCAGTTTGTTGCTCATACAATTTTCGAATGATC
GTTAATCGTTGTGTCTGCCGTTGATTCAATTGCCCGCCTTGTGCTTGCAGTTCTTTGACGTAACG
CAAGTCACGTCGGATGTACTGTAATTGAGCCTTGATCTGCTTATGGGTCGTTTTCACCCAACGGC
GGGGTTTACGTGAAAAGGCGGTCCACGTTTGGTGGGCCTTGCGCTTATAGGTACGCGGCGGTTT
GACCGCTAATTGCTTGGCCATGGCTGCGATGAATCGCTCTAAATTGAGCCGCGCCTGATTGAGT
AGCTGCGTATCCTGCGGATACTTGATCTTTACTGGGACCGCAGTCGCATCAGTGATCAAGATCTT
CTGATGGCCAAGTTTAGCTTGGAGGCGATCGCGGACAAAATCGCTAATGATGTTCGTGATCAACT
CGGAAAGCGGCGCGATCCGGCGCCTGAAATAGGACAGCACCGAAAATGAAAACGGTGCTTGCG
GCTGATACTCTGGCAGGCCAATAAAATACTGATAAGCCGGTGTATCGCGGATCGCTGCGACTAA
CTCACGGTCCGATAGCTGAGTGCGCTGCTTGATCAGTTGGGCGCCATAAAGCAGCCGAAAGGG
TTTACCTGCCCATCCTAAGTTAGACGGGAAAGCCAATTGGTACGCCTCTTCTAGTTGCGGCCACG
GAACTTGGTCGGCCAGTTGGACCCACTCGTTATCTGGACTTAATGGGGTGCTTAAGCCGCTACC
AAACGATTTGATCGATAATTGAACGGCTTTTCGACGATAAACCATGATCCATGCCTCCGATAGGG
TCGTGTCAAATGCAAACGAAATGAGCACGATCCGTAAATTCATATGCATTCATTATACGACGATAA
CGGGTTCAACTCGCATCAAATGTGGTTATATCAAATTATTCAACAGCCACTAGGTTAAGATCTTCA
TTTAAGTGATATTCATTTGCAAGCAATTGAAAATTACTCATCACGAAGAGGATTTCATTGGCCATA
TTGGATAGCACGCAAATCACTTGCTTTAAGAAAATCAGTTCCTTTAATGAGTCTCTTAAAGGACGG
GGCTCTCACTTGTACTCACAATCAATGTTAACTGGAGATCAACAATATGGTCATAGATTCCCATAA
TAACATTGACTTGACTATCTAAAAGAGGCTTCTAACTTTGATATTGGTGGGGTTATTGGTTGCTTG
GCTGTAAGCAGATAATCTTAACTTGGGTTATTTTCATTGTGTTGTAAAGACATTTGTTATAAAGGC
CGAAGTTATCGCTTTGACTTGTAATAAATTATTTTTGATTGAGATATCAGAAAATAAACGGGGAT
AATAATGAAAAGATTATTAGGATTGTTCTTTGTGTTGTTAGTTGCGTTAGTATCATGGTCGGATC
GCTTGGGTTCTATTCAACTCCAAAGATCGTTAAAGCCGACAGTACATCTGTTACGGATGTCGACA
TTAATACCTATATTTCTAGCATGACACTTGATCAAAAAATTGGACAAATGTTTGTAGCACGAACCT
CACAAGATACTGATAAAGCTCGTGCTGATATAGCAAAATATAATCTTGGCGGGCTGATTGTTTATG
GTGTTGATTTCACTAGTGTTAAAGGGACAACAGCTACAGAAGCTCAGAATAACTTCAAGATGAAG
ATGCAAGGCTTTCAAAACTCGGCAAGTCTGCCACTATTGATTGGTGTTGATCAAGAAGGAGGGG
CAGTCTCACGCTTATCACAAAATCCTCTAATTGCCAACGGCAGAAGTTTTCCTTCACCACAAATG
```

-continued

```
GCTTATGCTAATGGTGGAATGACCAATGTAACAAAAGAAGCTAGTGAAGTCGGAACTATTCTAAA

AAATCTGGGCATTAACTGGAACTATGCACCAGTTGCCGACAGTACGCCTGACACCTCTAGTTTTA

TTTATGGTAGAACCTTTGGTCAAGATTACTTGGCTACTGCAAACTATATTACGAATGTGATCCCTG

CGTGGCAAAATGCTGGCATTGCCGCAACTCTCAAGCATTTCCCTGGTTATGGATCCGCGATTGAT

ACGCATACGGATTTTGCAGTCGTTACAAAGTCTAAGGAGGATTTTGAAAAAGAGGACTTGCTTCC

CTTTAAGTCCGGTATTACAGCAGGGGCAGATTCTGTAATGATTGCACATATAGTAATGCAAGCTG

TTGACCCAGTGTATCCAGCATCATTATCACGGAAGGTCGTTACCGATTTGTTGCGTAATGAACTT

GGGTATAATGGCTTAATAATTACCGATGCATTGGAAATGGGGGCCATCAAGCAATTTGCTCAAGA

ACATGATCAAGTTCCTGTTGATGTTCTTGCTGTTGAAGCAGGGAATGATTGCATCATGAATAACG

ATTATGAAACCGCTATTCCACAGATTCATGCAGCAGTAACTAATGGAACTATTAAGGAATCAGAAA

TCAATGAACACGTTTTCCGTATTCTTGATCTCAAACGCAAATTAGGGTTGTTAACTAAAGGACAAC

TTCAGCAAAAAAAGTTCAGGTTGACAATGTTTCCTACAGCAGTGACAACAAAAGGCAACTGTG

AGTGGAACAGTTGTTGATAGTGATTGGCAAGTTGGAGAACCATTATCGGTTAAAGACTCGACTGG

GAAGGTCATTATTACCGCAGACGTTGGTGCCGGTGGTAAGTTTACTTTCGATGTTCCTACTAAGT

CCCAAGAACAAGTATTAACTCTGACTACTAATTTACCCAACATCGCTGATTCTCAAATAACTATTAA

GGCTGTGAGTTCATCGAATACTAACAAAGCTTTGCTAGAAAACTTGATCAACGCTGCTGAACAGT

TGGATAGTAATCAATATACTGTCAAGTCGTGGGAAGAATTACAAACTAAACTAACTGAATCAAAAT

CGATTCTGAACAATGATAGTGCTACACAAGATCAAGTAGACGCTTCCGTTAATGCTCTACAAATTG

CCCTTAAGCAATTAGTTCCTGTATCAAATAGCGGAAATAATGGTCAAAGCTCTAATGATAGCAGTA

ACCAAAGTTCATCTAGCAGTAGTGGCAAAGAATCATCCAGCAATAGCAATGCCAATATTACTAGT

AAGGATCAGTCAGCTAAGGATTCAAATACGAGGCCTAAAGACCATAGTCTTTTGCCAAGTACAGG

TGAACGGGTGATGACGGGAATTTCTGTTCTAGGGGTAATTTTAATAGCTTGTGTGACTATATTATA

TATTCGGAAAAAAGGACGCAGCTTTTAATTAGTCTCTGCGTCAACTGGCGTTAAAAACTAGATTGA

AGTAATAAAGTTACCACCTGGAAAGAGGCATGCTCATTGCTTGCAAGGGTGTCGACGTGTAATAG

AAAAGTTGGGG
```

SEQ ID NO: 12 Position 325750..327159

```
TGGCGTGGGCAACGTGCACGTTTTCTAGTCGCTAAACTGTGAACAATGCTCGTGCTAAATGCAAA

ACTGAGCAAGGAGATGAACTATAAGCGGGGACCCTTTGCTATTGAGGAGGAAGGCGAAGTAGA

GAAAGAGCGGTGATTTGAACTCGAAACAGCGGCGCCGCAGGCTAGCAGCACTGTTAGATTAATC

GCCAGCAGCAGATACTAGACAGCTTCTTAAAGGCTTGATAATAGCGTTGCGCCATTTCAATGGAA

CTAGTGGTCAAAATCGCATTGTAGTTGCCATGACCCAAACTCGTTTTACGCGGGCCTTTTTGTAA

AATATATTGAACAACTTGGTTAATATGTTCATCGGTCTCAAAGTCAGCCGGAGTTAAATACGTTTC

TTCCAAGTCCTTCACTGACATCGCTTGAATCTTGGCTTGAATTTTCGCTTCATCAGCCGTACTCAG

CAGGCGGCCTTGCTTATCACGACGAGCTTTAACGCGCTGAGTTTCTTTTTCAAGGGCCCGGGTT

ATTAAAGCGTCTTTACCAATCGTTGTCACGTGTTCCACATTAAATGGTAACACTGCTTGGTCCTCT

AAGGCGTCTCGCAAGTTATAAACATGACAGACTTTACCAAATAGCTCCTCCGTCGTAACTGCTAG

ATCACCTTTGAGCTGTTTCTTATTTTCATTAAAAATGGGGGTGCCAGTGTAACCATACCAGTTACT

ATTGATAAACGCTGCTCGAATTTCCTTTTGCATCTTACCAAACTGCGACCGGTGGACTTCTTCAAC

AAAGAAGATCACCCGTTGCTTTAAAGTCTTACTAAAGCGGGATTGCTTACCGGTTGCCAGCTGGA

CTTGCGTTTTTTTGACCGCCCGATGGAGCTTTTGAATCGAGGTGACCAAGACCTTACCGTCATTT

TGTTGCAATTTACGCATTAAATCACCGGTGTTTTGGGCTTCGTTAATGGCAATATCATCATTGGCA
```

-continued

```
GCATAGGCACTAAAGTTGCTGGTTGTCTGTTCGTCTAAATCCCGCCGGTCAACTAAGAAGATGAC

CTTATCGACACCAGGATCTTGCGCAGCTAATTTAGCGGTTTTATATGAGGTGAGTGTTTTACCAG

AACCCGTGGTATGCCAAACGAAACCATCCTGATGGTCATGAATCCGGTGCATCACGGCTTCAAT

CGCATAAATCTGGTAAGGCCGTAAGAGAATTAAGCTTTGCCGCTCTTGGTCGATGACTGTATATT

CACTGACCATTTTGTGGGCCATGGGAATATTAAGGACTTGGCGCGTGAACGCTAACCCGTTTTCC

ACGGGGTGATTATCCCGCGTCCGCCAATTGAACAAAAAGGCTTTATTGAAATGATCCGGTTCGG

CATTCGCAAAATACGCCGTACTATCCGGCGTCATAATCACAAAC

SEQ ID NO: 13 Position 328723..329314
CGATCTAAAAGCTAAGTTATTTTCCAAGATATCAAACAACTTCTTAACCCAAGAATCTTCCACACAT

AGGACAATAATGAATCCAAATAGATTCAGCTTTTTCCTGCAAACCGGGATCAGTATAAACGTCCA

GTACCGGATAATCACGCATTAAGTTCAGCTGCCAATGGGTATCATCTAAATTAAAAAGATCCGATT

TAGTGTCTCCCCTTACTACATTATGGCAATACACACAACTGTTGTTATACATGCTTCCTTGCTTTTT

GATTTTAAACTCCTCCATTTTGCATATTATAAGAAGATTACTTCTACTTGATATATAGATGCTTTCC

TTGCGAGGGTAAGTCAGACAAGGAAGCATTTCTAACTTGAGATACTTAAGCTTGTCTCAATAGAT

GTAGATAGCGGCTCCCCAATCGGATATTAACAGCTCAACTAGTCAAACCAGATATATAAATGTGA

CACAAGCTGGAATATATATCATTATCTAGATAATTCAAATTGAGCTAATAAAATCAATAAAGAAAAT

TTTAAATAACATTATTTTATAAACCCCTTTAGGATTTTCCCGATTTGATATTCTACGTATGTT

SEQ ID NO: 14 Position 2002858..2005090
GAGTATCCAAAAATACGACGGGTATTTGAATAGGATACTTATTAAGCGAGAATGGTATTGGAAAT

CTGTGGCAGCCACTCAGCGGAACCATACCTTTATCCCAACCCCACGCAAAAAAAACATCAAGTAA

TCCGTCAGATATGATGACTTAATTGTGGGACAGTTCTAATATGAAGAAAACAGGTTAGATAATTGG

GGTGAAAAGATGGCAACCTATTCGCAGATAGAACTAGACATAATCAAATCATTTAAAGGGCTGAT

GAAAGACCATGAATTCACTGAGATCTCAATTAAAATGATCGCTGAAAAAGCCGATATCACTCGAC

GCGGCTTTTACAATCACTTCTTAGATAAATATGATCTTGTCAGTACCATCTTTGAGCATGATCTTTT

TCCAACAGTCATCAGTTTGACGAATATCAATGACTGGGATCAAGGGTCGCTGTTTATCGTGAATT

ATCTCCAAGACAATCGCGACTACTATAAAAAATTGTTGTCGCTTGAAGGACAAAACTGTTTACAGA

CAGACTTTTATAAATTGACTGAGATGCAGATTGGGATCTTGATCCCAGAAATATTGGTCGGTAGG

AAAATTTCTGACGAAGATCAGGCATTTTTAAGCGATTATTATTTTCACGCTTATATGGGACTGACT

ACCGAATGGGTCAAAGGTAAATATGGTTTTTCAACTCAGGAGTTCGTTAAACGGTGGAAAGCCTT

ACTCAATAATTCAATGCATAATTATCTGGACAACTACGCTCGATGAATTACACAGATTGGATTAAA

TGAGAAAGATGTTACATTTGTGCCAATATGTGAATTGATAAATATTTCACAAGGAACTATTCTTTCC

CTGTAAACGAAAGTTGACTTGAAAGGAGTTAGTTCTGATGAGTAAATATAAAGTTATTATTTGGGG

ATTAGGAAACGTTGGTCGTTCCGCAGTGAGAATGATCGCGGAAAGACAAAATATTTTTGAATTGG

TTGCAGCCGTTGACGTTGATCCAAAGAAGTTAGGTAAGGATGCCGGAGAAGTCTTTGATTTTGAC

AAAGTCGGCGTCAAAGTTTCAGATGATATTGATGCAGCCTTGAAACTTCCAGCTGACATTGTGCT

CGACTTTTGCCCAACGGAAATGGACAAACAAGGAACATTCATGCCTTCTGCTATTCGACTCGCCA

AATCGCTCGATGCCGGTAAAAACGTTATTACCACGATTCCGGTATATCATGTTCAAGACAGTCAG

CCAGAAGTATATGAATATCTAAATGAACATGCTAAAGCACATAATGTTGCTTTTGTACCATTTGGA

CTTTTGCCAGGCGATTATGCCTCATATATCCCACTAGTTTTGGCCGGGGCCATGGGCCACGTGG

ATAAAATTGTTGTTCAATCCGGTGAAGATGACTGGCACAACACATCAGGCTGGGTCGATGTCTTC

TCATATGGCGGCGATATCAATAAATATCCAAAACCAGACTCAGACGAAGATCTCTTGGCTAAGTT
```

-continued

```
CATTTATGCTTATTATTCATCCGGCGTATACGAGATGGCCGATAGGATCGGTCTGAAATATGATA
CCTTCAAACCAGAGCATGAAGTCTTCACTGCACCCAAAGATTTGGAAACGATCAAGGGTACAGTC
AAAAAGGGCAGCATTTATGCCCACAGATTTACCATGGCACTTTACAACGGCAACGAACAAGTAGC
CGCCTTAAGATATGTTCATAAAGTTGATAATAAAGAGACACCAGAATTACCGATCAATAATACGAT
TCATATTGAAGGCTTGCCGTCAGTCGATGCGCAGATCGATGGATTGATCCCAGAAAGAGAAGGC
TACGTTTCATCAGCCGCTCCAGCAGTCAACTTGATCCCTAGCATTCTCGAGACCGACAAGACAG
GTTATGTTGAAGTCTGCGACCTTCCAGTAGTGATTGCCAGGCCATTGGATATTGGCGCAAAAAA
TTAGTCTAGACTAGGCTTTCGAAGCTGCTTTGACCATTAAGGTTGGAGTAGCTTTTTCATTTGCAA
GTAAATCATTACGGCTTGTGTATACGGTATACAAAATGGAGAAAACGCTGACTAGTTTATAAATCA
TTGAGACTTAACGGCCGGATAAATGCTGATCTGATTATAGAAATAACAACAAAAAGGCCACGCTA
AAAATCATATTAATTATAATCGGGAAATTTATTAATAATATTCAAGAAAAATAAAAACCGTGGGTAC
ATTATTTAAAA
SEQ ID NO: 15 Position 2262750..2268615
TTTGAAACTAAGACGAAAGCTGCCATGTCAAACAAAGCCGCCATAAATGCCACTGTCACA
GATCCATCAGCCGCAATGCCAGCATCTTGCTGAAGTTCTTTAACAGCATTAAGGGTGTTA
TTCGTGAACTCATTATTAAAGTCTACTGGACTAATCCCTTTGCACCAGAAAGCCCCTTGA
ATGAGTTGAGCAATGTTCCCCTTATATCCTGGCTTCAGACTACCTACAACAGGTGCTAAG
GCGTTTTTGGTCGTCTCGCCAAAGCCTTCACCAATAGCACTAATACCGATTTCGTGCTGT
AATCCCATTCTTAGGCTATAAATTGTTGGCCATCCCGTTTGCCCGTTTTCTGGAGCTGCG
ACAAAGCCAGGAACGCTACCATACGTTTTGTTGAGCCATTTTTGAACGGCTCGTACTGCT
TCATCTGCCATTTTAAAGTCTCCTTTTTTGTTTTAGACAGCACGTCTGCCGTCACAAAAA
GCAAACATATGTTCGGATTCATTTCATCTCTTCAAAGCTTCGAAAGGCAACCCTGATCCA
CAAATAATCCTTTTATTTTGAACTTAGCAAAAAAATGAGGCCCTCACATAGTGTTGAAGT
TGCCTCATTCTTAATGTCTATATTTAAAGTATTGCCACAACGATGGATCATCGAACGCTC
ATGGACTTGGTTAGACATGTATCGACGACTATGAAAATGTGGGCGCAAGCTCAATTTCAC
CTTCCAAATGTTTGTGCTATCTCATTTAGCGCTGGTTTTTTTAGGATAGACTAGACAAGG
ACTAATAATTTCTCAAGAATCCCGCAACTCCACTATTCATTCGTCGAAATCCCCACTGAT
ACTCTTGTCCTTGCACGTTCGACCAAGCAAGAATGTTTATTCCGATAACCGAATTGTTGC
CATCAAGTAATGGACCTCCCGACATGCCATGATACGAATTAATTTGTTGTGAAATATATA
TTCCTAGTGGGTCCTCTGAAAAGGGTGTGACAGTCCCACTTGATTGAACCATGACTCCTT
GAAGTTCGTACCCTGATTGCGGATCGCCAGGGAATCCAATGGATCTTGCTGCCATCGTAT
CAGCAGGGTTCGTATTTAAATTAAGACCCGCAGGCATACTACCAGACTTCATAGAGACAA
TTGCAGCCCCGTAATCATTCGAAGTAGCTGTTGAATTATTAATCCATGCCTGTGGCACTA
TCAATCTATTCAATACTCCGTAACCGACCCCTTGATGATTGCTTGACTATCACCAAAGT
TAATAATTCCTCCAGAAATATAATGACCATCATATAACATGTGTGCTGCTGTCCCTATAC
GGTCTACTCCAATGCTAAATCCAGTACCGCCAGAAGTTCCACTGCTCAGCTCTGTGCCAT
TTGAGTTAGAGATGATTTTTTATACGAACTGTCAAGGTATGGTGAGTTAATGACCATGA
CACCATTTGCCATCGAAAACCACGTGCTCAAAACCCCAACGGAACTGTACGGCGCCGAAT
TGGGGTTTGACACAGGTGATACCGTCCTCACAGATAGATGATTAGACGATTTATTCAGTT
TCGCAAGATATTCGGACGTAATTCCTTGAACTTTCTTTCCTTCTTTTAAATCCTGATATT
GATCAGGTGTATAAGCTTTGACACTCCCTTTAAAATCGGGATAAGAATACTGATATTGTC
```

-continued

```
GAATGATTTCATTCAAAAACTGTTGTGTTGTCGTCTGGTTAGTCAAAACAATATCATTCT

TTGGTAAAACATGGCTATTCGCTGCCAAAGGATTTGCCATACTATCAGCACTTACACTTA

CCGTTTGAACTTGAATTATCGCTAAGGCTGCAGCTATCATAGTGATATATGCCCATACTT

TTCGCAATTTAATTCCCCCTTTTTCTTAAAATGAAACCGCATTCACGGAGGCTTGTCAAT

GCTTTTAAAAAACAAACGTTACTTTTGGCTCATCTTGGCTGTCAGCATAATTGGAGTAAT

TGTTCTTGCGGTGTTATGGCGCATGAACCCTGAAGGAACGGCCTCAAATAAGTTTGAACG

TCCCACCATTACTATTAAAAAAGTCAAACTTATTAAGCACAGTAACAGTATTGCTGTCAC

ATTTGCTACCTCTCCAAAAAGCAAATATACGATAAGTGATCTTAAAGAGAATCAACTTTC

TTCTGGCATTTCGAATAAAAGAGAAAATACCGTTTCGGAATTAAAGCCCTCCTCCTCTAA

GCTTGCAATACGGGTTAAGCATAACAATAATATACAAACCAAAGTGGTTTCTGTTCCCAT

TGGTTATCATATTATGAAAAGTGCCATTTCAAGAAAGCCAATTCCTATGGGAGAAGAGTT

TAAGTACAATGGAAAGTCGCATGTTTTATTTAGCATGACCATTACCCCTAAAAAACAAA

CAAGAACAGTATAAAAAACACCACTGCTTTTAACATAACGGTTAAAAATGATCACTACCT

TGTCCCTGTCGTATTAGATACCAAATACCTTACTGTTTCTGATTCAGAAGGTAACTCATT

AAAAGTAAAGCCATTCTCAAAAATTTCTATTCCAGCAAAAAGAAAAAGACCATTGCAAT

AACTATTGAGGGCGTTCCCGCAAGCTCTGCCAATGGTCTAGTTATAACGTATAATACTGT

CGATTTAGACTTACCAATCTCCTTTATAAATTCCTGAAATTACACTAACTGTCCCCCACC

TTGACAGTCAGTACACTCAAACTGTCTCTTATGCTTACAAACACGTAATTTAGGCGGTTT

TTAAGCAAAAGTCGTTAGTTTTCATAAATGTTATCTTATACTCTAATGAGATCTAGCTTG

TGATAATAAGGCTGTTTTTCTTTGACAGCCTTATTAAGCACACTAATCAATGTCAATTCG

AAGTTTTTGGTTTCCTACTTGGCCAACTTTGTTATCAGAAATTCCAAAACTCATTGCCTC

CCGCCACCATATATTTATCGAGCCATTTTGAAAATGAAAAATCGAAATATCGGTCTGCTT

CTATTCCGGGATGAGTTAGATATGATTTTCCTAACCGATACTTCTCTATATCAATATACA

TATCTCCGACATCCCTTATATGGAGAATGGGTACTTTATTTACAAAACTTTTAGGCAGTG

CCTCTTTTTCTTTAATCATTTTTCTAATTGAATAGACTTCACACGTATATCCCATAGGAA

TCCCTTCGATTGTTGTGTCAAATAAAAATAGTCCATTAGTAATCGAGAGAAACTCAATGT

AATCCTGTGGAAGGTTCCACCTTTTTATTTTTCTATATCATCAGCGTGTGCAGGAGGTT

CTATCTTAAAAGAAACATTTTGCACATCTCCATCTAATTGGAATGTTGAGAGCGCTTTTT

CCCCATTTTTCGTCACCTTTATTAAAGAATTAATTCTTCGCCGAATTAGAGATTCCAAAT

GAGTTCCTCCTCAATAGTTGTTAAACCACGCGGTGATCAACCGATGATTTGGTGTTAACA

CCGGCATCAAATTATTAAAGTCATTTGTTCCGCCATAAACTCTCGGGCAATATGATGCA

CTTCTCGAGAACTCCAAAAATCTGCAGATTGATTGCCATATGTTTCACTGAACGTTTTAA

TATAAATATATCTATCTTTTGATGACCAACTAGGAGATTTTGATAACTTAGTCCAGGTAG

TATTAATAGGTGTTTCTGCATCTTTTTTAGACACGGGATCAACATATTCAGGGAAATTCT

GTCCTATTTTATTTTGTAAATAGATGGCCGTTGGTGGGATTGGTTTTACATTAGCCGCTC

CATTAACTCCTATAAATCCAACAGCGCCAGCAACGTTAAAAAATGTGGTTTTGGCTGGCA

ATTCTGTAAAACCAAGTAATCCTGTTTGCAAACCGCCTATTTTGCTAATGGGTGCCAGCG

TATTGGCATTCACCGGACCTGCAAGGGTAGGCTCAGTATTAAATTCAATTTGCACATCAA

CTGCGGCTGGCGGGACACCCTCAATAGAATCAATCCAGAAATTGACTCTGAATTTTCCGG

ATATGTATTCTTCCGATAAGTGCCAGGTAATATTTGTAACAGGAACTTCTGCACGAGAAC

TTATGCCATTGCCATGACTATTATTCAGTACCACTTGTTTTCCAGAAGCGATAATTGGTT
```

-continued

```
GTCCATTTTCTGGATTACTTCTTGATAACTTGTCAGCATTGGTCAGTTGAGTATTGTTAT

CGCTAATACGGCTTTCAGTTGAAACAATTTGATTTAAAGATTGTGTTGTGTCTGCGGATA

CAATTGTTGAATACCCAAGCAAATTGACTAGAAAGAGCCCGAATATTAGCCCAATAACTT

TCCACTTTTTCACGCCTATTATCTTCTTTCCAAAGTTCTTCAGTGCCTGGCAATAACTGT

ATACATTGAGCAGTATAGTCGCTATTTTATAGCTGAACAACTCATAAAGCTCAATTATTA

TTAGCCTATAAAACCACTGCCTAAGTGAATTGATCTAGAACGAAGCACGCCGAAGAAGTC

GCTAAATGTGCTAAGAAAAATGTGCTTGAATAGCTCAAAAGTAATTAGCGTCTCCATTGA

AAATCCGTTATTTTTAAGTGATCTAGTGTTAACTATGAATCCCAAATAAAAAGCAAAATC

CGTAAATGCCAAATTTTCCTTTTTGACGTTTTTCTACTGTCGCGAGATTTGCAAGTGTAC

GTACACTTACGATGAATTGACAGAATCTCAGCTGCGCTGATCGTCAATTTTGTTTGGGGG

CACGCCCCCAATCCCCCTGTTATTTTGAAGGGAGGTGAGTCCCCCTTCAAAATCAAAATT

TAAACAGCATCTGCCGCCATCTTTTCGCTGACCTTCTCACGATGTTACACGTGGTGTTGA

CACCCACTTGCATTTAGAGTTTCATTCAAGTTGAACATTGTGTAATATATGAGTTGCATT

TGATAAACATATCAGTTGCTATTTGTGCAACTTTAAAGCTTCGGCTAATTCAACGTTCTG

TTAATTTACAAGCATCTCGACAGTTTCTGTTAAAGCAACATCTACGCTTCAATTCGAGCA

ACTCACTATACGTATGCCGAGTTGCAGACAAGCTACTATATAGCTGTACGCGCTGAAACA

CCAAAAATCGTTCGTTTATGCCCAATAAGCGAATAATCTTGCTCAGGTGTAGTAAAAAAC

TGTTTACGTGTAGTGAATGGCGCTAGCCCTTGTCGTAACTGGCATCATCCACGTGTAGTA

AAACGCGTTTTACTACACGTTCGTAATTTTTTCACGTGGAGTAAATGGCGTTTTACTACA

CCTTTTGACCCCAACGTGCTATCACGACAAACCAAACCGCACTGCGGTTTACCCCAATTT

TGGGGTCAGTTTTGCCTTATGCTCTTTCATGATTTTAGGCGCGTTCCAAGCAGTCTCAAA

AAGTGGTCGATCCAGGCGAGCCGATTTTTGAGAAGGATTGGATAGCAACTCAATTTATTT

TGATCTTTTGCTTGGAGAAAAACGTTCACGTTTTGACCAGGGCCGTCGCAACTGTTGACC

AAAACTCGTCCGGTAACGTGACGCTATTTAAACGCCGCGTTGGTTTGCTAGACGACCATT

CATCATCACCATTCAGGAGGTTTTTGAAATGACAAAGCAAGACGAAACACACCGGGTCAT

GTTCACTTTGACCGATCAGGCGATTGCAAAATTGAATCAGCTGGTCGCAAAAAAGCAACA

GGAAGTGAATCAAAATCCGGAACTGGCTAAGTACCATGTCAGCGTGACCAAATCAAATAT

CATTGAGGACTGGTTATCAAAGCAGTGAGTTTAAAAAGCGCTAAAGGGCCTGTACTAGCG

TTTCTTACTCTGGTGGGTATAATTAATGCTCTCTACATCAAAAACG
```

SEQ ID NO: 16 Position 2776965..2787971
```
GCCACGAACCTGTAGCCGTTTGGATGAAGCCATATAATACTGGACCAACCGCCGCAAATA

AGTAGCCGACACTTTGAGCAAAATCAGGAATACTAATCTACTTTGCCCTTAAAAAATCTT

GAGATGATCCATATCTTGTTTTGCCTTCATTACTGTAGTTGGTCATAAGAAGTGCCCTAC

ATTCATTAGATTACTTGTCTAATAATTGTAGGGCACTTGGGTTGAGAAAAATGATGTTAA

CTAAGAATGCAAACGAACTAAAATCTTTGCTTGCTTTTTATCCTTTTCTAAGGATTCAAT

TCCTTCTGAAACTAATTCATTTAATTCAATCTTTTTTGTAATGACCTGTTTGAATAGTGA

ACGATGGGTATCTATAATCTTAATTACTCGATCGAAGATATTGGCATATCCATAAGATGT

TAATAAACTACCACCTTTTTTAAGAAGAGCTCTAACATCTACAACTGGTGGATGTTGAAA

TAATGCAATCACGGTAACCTTGCCACCATTTTTAAGAGCCTGAATGGCACCAGTAAGTGT

GGGTTGTACACCGGCGCAATCAAACGCAATATCCACTCCCTGATTTTCCGTGATAGTGCT

GATAGCGTGAGCTAATGACTTTTGACTATCAGCACGTATTGGGTATTGAATTCCTAATTC
```

-continued

```
ATTTGCTAAATTCAAACGTTCCTCTGACATGTCATTTATTATGACGTGATGTGCACCAGA

AATTTGTGCTATTAAGGCCGTGAACAATCCAATTGGACCAGCACCTTGAATTAAAACATC

ATCTCCAGGAGACACTCGGCTTGCCATAACTGCCTGTGCAGCAACTGAAACTGGTTCAAC

TAAGGCCCCTAAATCAAGCGGAAAGCTAGCTGGTAAGAGATGTGCAAAGGTACTTTTTAC

ATTGCACTTTTCAGCTAAGCCACCGTTAGCCGAAAATCCTAAGAATCCTGCTGATTGATC

ACTACCTATAGCATGTTCACACCAATTATAATGACCAGAAAGACATTCCGGACATTTTCC

ACAAGCAATCATTGGTTCGACTGCAACTTTATCTCCAATTCTTAATTTAGATACTTGTTT

TCCAATTTTAGAAATCGTCCCAGAAAATTCATGACCAGGAATTAGCGGGGCTTGCATATG

GGTTAGCGGATGAGGTATTGTCGCCAAATCCATACCCTCTAAATATTCATGAATGTCACT

ACCGCAAATACCATTAAATGCAACCTCAATTTGAACTTCATCTGGTGCGGGATCAGGAAT

ATTTCTTTTTTCAAAGCGGATATCCTTAGGACCGTAAATAACAGCTGCCTTCACCATAGT

CATAGTGCTTCGCTTCCTTCATGTTCAATATAGCACAATCGTATATAAAATAGTGAATAG

ATTTCAGTAATGAAGTTACCATCTTGACTTAACAAAAACTTGCTAACTGATTATATGAGA

AACTTTTACTTGAAACATTTTTGGTGATTACCATTAATTCCCTCGGACATATTTTGAAAA

ACCCTATTTGATGCTGATTGCAAATTATTTTATGCGTATTTATTAAGGGTTTCTATGTTG

AAGTATATAGCAAACTTGTTCAAGTAACTGACTTTCACGTGGGCTTTAGCCAAGAGATGC

TGAGCAGCGAACCCAAGGGGTGTTACTCGCCCACGCAAAAAAGAAATCCAATTGCATTCC

AGTATGAGCGAGAAGCAAGCCATTAAGACGCTGATTCATGAACTCGCGCACAGTGAATTA

CATTGTGATCCGAAGTTAAAATTGGATCGTTCAACCATGGAATTGGAAGCTGAAAGTACC

GCGTTTATCGTTTGTCAACATTTGGGAATTGACACGAGTGATTATACGTTTCCTTACCTT

GCTGTTTGGTCGAAAGATAAGGATCTTTCCCAGCTCTCCAAAAGCTTAACGCGTATCCAA

TCCACCGTCGAAAAATTCAATAAAACCGTCGATCAAAACCTTGAAAAGATTCGTGAGAAA

CCGTTGACGCTTGATCAAAAATAGAACGCGCTAAAACCATTGCGACAACGGAAAACATC

GCAAAAAAGAGCAAGGGCTGGTGCAAGCAACGCAGGAGAAAACACGCTAACCCATTTGT

TGAATACTCTCACTCAAGAGGACACTCCAGCCCTTGATCACCCAAGAAAGGAATTACCAA

CATGAAAACCATTGACGAAATGAACGAATTCGATCGTGACATTATCTTACTTCACCGCAA

GTCTGTGAGCGAAGATACACCGCAGGCAATTCTTGTGAAAGTGAAACAGATTCGTAACGC

AATTGCCGACGAAAAGGCGGGTAAAGAAGATCCAATTGAGAAAGAATTTACACTCGAATG

TTACGACGAAGCAATCAGAAAACTAAGGGACCTTTCGGTCGCTGATTATCAGTTGTGGTT

GCGTCAAAACAAAGACCTGGAAGGGTTTGAATTTTGATTTTGAAGGGTGTCGTAGACCCC

TTCAAAATAACGGGGATTGGGGGCGTGCCCCCAAAACAAAATTGACTATCAGCGGAGCT

GATATTGGATCAATTTATCGCAAGTGGACGTCCACTTGCAAATCTCGCGACAGTAGAAAA

AGCCCCAGAAAAGCAAATCTGAAAAAATGTAACAGGCACTTGATATCAAGTGCCTTATTG

TTTCTAGGATCGCTAAAAATAACAGGAGGTGGTTACATGAAGCAATCTGATGAACACCGC

ACGCGTTCAGTGAGAAGCACTGTGCGTATGACCCCAGAGGAGCGTGCTTGGGTTGATATG

AGAAGAGCCTCTGTCGGCAATCCAAAGTTCAATGCATTTGCCTGTCGCGCACTCACGACG

AGCAAGATCGTTCATGTACATTTTACTGATACTAAAAAGTTACTTAGACAGCTGTCAAGA

ATTGGGAATAAGGCTCCTATGCTGTAATTACGGACAAAAATAGTTTGTGCGATAATTACA

GCATAAGGGCCTCTAGGTCGGAGCCCAGGAGGCGGAGACCGCCGCACAGCCCAACCCCAC

GCCGAACCGGAGGCCAGCCCGCCCGCACCGCGGCCGCAATCATCCACCCAACGCCCCCCA
```

-continued
```
AGTTTTTGATAGCGGTAACAACGCCTGTGCGCTTGTCGTGGCCGGCCTTTTTTCATAAGG
TTGGAGGAGAAAGGAAGGGTGGTTATGGGCGCTTGGTATGAACACGCAATTATTTACCAA
ATCTATCCAAAATCGTTTCAAGACAGCAACGGCGACGGCATCGGGGACCTGAACGGGATC
CGGCAACGGATCCCGTACCTGCAAGCCCTCGGCATCAACACGGTGTGGCTGAACCCGATC
TTCGTCTCCCCACAGGTGGATAACGGCTACGATGTTGCCAATTACTTCGCCGTGGACGAA
ACCATGGGTACGATGGCCGACCTGGAGGCGCTGATCGCGGCTCTGCACGCGGCCGGCATC
CGTCTGATCATGGACTTTGTGCTAAACCACACCTCGGATCAGCACCCGTGGTTCCAGGAC
GCCATTCACGCCAAAAATAGTCTGTACCGCGACTACTACATTTTCTCTGGCCACGACGGG
CAGCTGCCAAACAACTGGGGCAGCTTCTTCGGCGGATCGGTTTGGGCGCCGGATCCGGCG
GGAACCGGGCAGTCGTATTTTCATCTGTTCGACCGGCGGATGCCGGATCTGAACTGGGCC
AATCCCGAGGTGCGGCGGGCGATGGGAGACGTCGCCACGTTCTGGCTCGGCAAGGGCATC
GACGGACTGCGGCTGGATGCCTTCATCCACATTGCCAAGGCCGATCTGGGGCAGGATTAC
CCCCTGGCTCCGGGGCAGCAGACGCCGGTGGTGGCGGAGCCGTTTTTCTCCAACCTCCCG
AAGGTGCAGGAATGGCTGCGGCCGTTCTGCGACCGGATCAAAACCGACTACCCCGACGCG
TTTCTGCTCGGCGAGGCGGCATCGGCCAACGTTAACCTGGCGGCGGATTACACCGCGCCT
AGCCAGCACCTGATGGACAGCGTGATCACGTTCCGCTACTTCACCGAGGACGAAAGCGGC
CTGGATCCGCGGCTGCCGGCGCAGTACCAGCCGCGGACGCTGGATTTCCCGGCGTTCAAG
CAAACCCAGGCGGTGTGGCAGCAGACCCTCGCCGGGGTGTCGATGCCGACGCTGTACTGG
GGCAACCACGACATGGCCCGGCTGGCGACGCGGGTGGCCAAAACCACCACCCAGGCGCGC
AGTCTGGCCATGCTGATGTACCTGCAGCGCGGCCTGCCGGTGATCTACTATGGCGAGGAG
CTCGGGCTACACAACCTGCAGTTCGATCACGTTGATCAGTTTGCGGACGTTTCGGTGGCG
CCGTTCGTGGCCGCGGTCGAGGCCACCGGGCAGTCGCGGAGCGCGGCGCTGGCCATGGTG
TCGGCGACGCACAAACTGCCGGCACGGGGGCCGATGCCTTGGACGACCGGGTTGCACCAG
GGCTTTTCCAATCACCTGCCGTGGCTGGTTGGGCGCAGCGAGGACGTGACCAGCGTGGCC
GCGCAGCAGGCCGATGAGGCCAGCATGCTGCACTTCTACCAAGCGCTGATTGCCCTGAAG
AAGCAGCCGCTGTTTCAGGCCGGGCATTACCGGCTGCTGACGACGGCGCCGAACCTGTAC
GTCTACGAACGCACGCTGGCCAGCCGGCGGGCCCTGGTGGCGGTGGCCTTGGATGAGCAA
GGCGCCACCTTCACCGTGCCTGAAGGCCTGACGACCGTGGCGCTGGCCGCCGGCGATTAC
CAACTCGAAGGTCAAACGCTCACGCTTGGCGCGAACGCCGGCGTGGTGTTAAACGAAAGG
GGAACTCGATAACCATGCAACTTGCAGCATTACGGCACCGCCCAGAAAGCGAAGATTGTT
TTTTGTACACTCCAGATGAGCTGCGGCTGCGGCTCCACACAGCCAAGGCCGACGTGCAGG
CGGTCATCGTACTGTACGGGGATCCGTATGTCACCGCGCCGAACCCGACCACCGGAGAAC
CGGAATTCGCCTACCAAGAGGCGGCGATGATCAAAACCGGCACCGGCCAAACCAGCGACT
ACTGGACCATCAGCCTGACCGCGCCTTATCACCGCCTGCAGTACCAGTTCCTGGTGACCG
GTCAGGACGGCAACACCGTCCTGCTCGGCGACCGCGCTTGCGGGCCGACAGCGCCGCCA
ACCGCCGGGCCGATCTGTTCCGGGTGCCGTACTTCCACGCCATCGACACGGTACAGACGC
CGGCCTGGGTCAAGGAAACCGTGTGGTACCAGATATTCCCGGAACGCTTCGCCAACGGGG
ACAAGACGAACGACCCCAAGGGCACCAAGCCTTGGCGTCCGGCGGATCACCCGGGCCGTG
AGGATTACTACGGTGGCGACTTGCAAGGGGTGCTGGACCACCTGGACGACCTGCAGGCGC
TCGGCGTGAACGGGCTGTACTTCTGCCCGGTGTTCACGGCGATGTCGAATCACAAGTACG
ACACCATCGACTACTTCAACATCGACCCTGCGTTTGGCGACAAGGCCTTGTTCGCCGATC
```

-continued

```
TGGTCAACCAAGCGCACCGCCGCGGCATGCGGGTGATGCTGGACGCTGTGTTCAACCACA
TGGGCAGCCGCAGCATGCAGTGGCAAGACGTGCTGAAGTTCGGTCCGCAGTCGCGCTTCG
CCTCCTGGTTCCACATCAACCGTTTTCCGGCGGCGCCCTTCGCCGCGCCGGAACAGGGCG
GCGTGCCGCAGTACGACACCTTCGCCTTCGAACCGCACATGCCGAAGCTCGACACCAGCA
ACCCGGCGGTGCAGGACTACCTGCTTGAGGTGGCGACGTACTGGATCAAACAGTTCGACA
TCGACGCCTGGCGGCTGGATGTGGCCAACGAGGTGGACCATCACTTCTGGAAACGGTTCA
ATCAGGCAACCAAAGCGCTCAAGCCCGATTTCTTCGTGCTGGGCGAGGTCTGGCACTCCA
GCCAGCCGTGGCTTAACGGGGATGAGTTCGATGGGGTCATGAACTACGCGTTCACCGAGC
AGATCGAGGCCCACTTCCTGACCGGCAAGCTGAGTGCTCCTGAGCTGACGGCGGCGCTGA
CGGATCAGCTGATGCTGTACCGCGACCAAACCGACCAGGCGATGCTGAACATGCTGGACT
CGCATGACACCGCGCGGCTGCTAACGGTGGCCGGCGGCGACGAGGACCTGGCCCTGCAGG
CGCTGGCCTTCACCTTCCTGCAAACCGGGATGCCGTGCCTGTACTATGGCACGGAAATGG
GCATGGCCGGAGAAAACGATCCCGACTGCCGGCGGCCAATGGACTGGGCCCAGCTGAAGG
GCCCGATTTGGCAGCGTGTGCAGGCCCTTGTGACCTTCCGCCGCGCCCAGTCGGCAACGC
TAGGCACCGGCACCACGGCGCTGAGCGTGACCGCAGCCGGGCTGCTTAAGGTAACCCGCA
CAGGTGAGCACACCGTGACGGCGTATTTTAACACCACCAAGCAGATGGCGACACTGACCG
TCAGTCCATTACTGGCGCAGGGTTACGCCGGCCAGCGGCTGGCGCCAACCGGGTTTGCTG
TTATGGTTCAGTAAGATTATGTTAGCGGTAACAGGCAATTTGACCTTTTAAAAGCGTTTT
CATATTATCATAATCAAAAGTGTAGAAAAGTTCAGGTGGCGCAATTCACCTCCCGAAAGT
GAAGGATGCAAGATGAAACGGATATTTGAAATCGACCCGTGGCTGGTGCAAAGCCACCAA
TTGAACCCCAACGAGAAACGCCTGCAGGAAAGCATGACCGCCATCGGCAACGGCTACATG
GGTCTGCGCGGTAACTTCGAAGAAGGTTACAGCGGTGATCACCTGCAAGGCACGTACCTC
GGCGGCGTCTGGTTCCCAGATAAAACCGTCGTCGGTTGGTGGAAAAACGGCTACCCGGAT
TACTTCGGCAAGGCGATCAACGCGCCGAGCTTCATCGGCATGGCGCTCACCGTGAACGGC
GAGCGCGTCGATCTGGCCACCAGCGTCTACCGCGATTTCACCCTCACGCTTGACCTGCAC
CAGGGCCTGCTGACCCGGAGCTTCGTGTTCGAGGGCAAAAAGGCCACGGTGCGCTTCACC
TTCAAGCGTTTCCTCAGCAACGTAATCAAGGAGGCGGCGCTGGTGCAGCTCACCGCCGAA
AGCCTTGTCGGACCGGCCGAGCTGACGGTGGCCGCACAGCTCGACGGCAACGTCACGAAC
GAGGACAGCAACTACGACGAGCGCTTCTGGGCACCGCAGGGGGAAAACGCCGCGGCAGGC
ACCATCCAGCTGCAGACCAAGCCCAACCCGTTCGGGGTCCCGCAGTTCACGGTGCTGCTC
AAGCAAAGCCTGCGCCAAGGGGCAACCCTTTTACCCGGCACCGTGACCACCAGCACCGGC
CAGCTGACCAGCACGGTCACGCTGCCGCTGGCGCCAAACGTGCCGGTCCAGCTGGAAAAG
GACGTCATCGTGGTCACGAGCCGCCGACGTCGCCCCTGAGGCCCAGGCCGAAGCGGCCGCG
GAGCTGATGACACAGCTGCAGGGCCAAAGCTTTGCGGCCCAGCTGGCGGCACACACCGCC
CTGTGGGCCAAGCGCTGGGCCCAAAGCGACGTGGTGATTGAAGGCGACGACGCGGCCCAG
CAGGGGATCCGCTTCAACCTCGCCCAGCTGTTCATGACCTATTACGGCGACGATAAGCGG
CTCAACGTGGGGCCGAAGGGTTTCACCGGCGAGAAGTACGGCGGGGCGACCTACTGGGAC
ACCGAGGCGTACGTGGTGCCGATGTACGTCGCCGCCACCCCTCCGGCCGTGACCCGGGCA
CTGCTGCAGTACCGGCACGACCAGCTGCCCGGCGCCTACCACAACGCCCAGCAGCAGGGG
CTCAAAGGGGCCTTGTTCCCGATGGTGACCTTCAACGGCATCGAGTGCCACAATGAATGG
```

-continued

```
GAAATCACCTTCGAGGAGCTGCACCGTAACGCAGCGGTCGCCTTCGCGATTTACCAGTAC
ACGGCCTACACCGGCGATGAAAGCTACGTCAACCACGACGGCATGGAGGTGCTGGTGGGC
ATCAGCCGCTTCTGGGCGGACCGGGTCCACTTCTCCAAGCGCGCCGGCAAGTACATGATC
CACGGCGTCACCGGGCCGAACGAGTACGAAAACAACGTCAACAACAACTGGTACACCAAC
ACGATGGCCGCCTGGTGCCTGGAGTACACGCTGGCCCGGCTGCCGAAGGCCGATGCCGCC
ATTCAGGCCAAGCTGGCCGTGAGCGCCGCCGAGCAGCGCCAGTGGCAGGACATTATCGAC
CACATGTACTATCCGGAGGACAAGAAGCTGGGCATCTTCGTCCAGCACGACACCTTCCTG
GATAAGGACCTGCGGCCGGCAAGCTCGATTCCGGCCGACCAGCGGCCAATCAACCAGCAC
TGGTCCTGGGACCGAATCCTGCGGTCGCCGTTCATCAAGCAGGCGGATGTGCTCCAGGGC
CTGTACTTCCTGAACAATCGCTTCACCCGCGAGCAGAAGGAACGCAATTTTGACTTCTAC
GAGCCGCTGACGGTGCACGAAAGCTCGCTGAGTGCCTCGATTCACGCGGTGCTGGCCGCC
GAGCTCGGTAAGCAGGATAAGGCCGTTGAACTCTATCAGCGTACGGCTCGTCTGGACCTG
GACAACTACAACAACGATACGGCAGACGGTCTGCACATCACCTCGATGACCGGCGGCTGG
CTGGCTATCGTGCAGGGCTTCGCCGGCATGCGCTACGACCACGATCAGCTGCGGTTCGAT
CCGTTCCTGCCGAAGCAGTGGCAGGGTTACCAGTTCCGCATCAACTACCGCGGCCGGGTG
ATCCAGGTCGCGGTGGGGAAAACCGTTGCAGTGACCCTGCTGGCCGGCCCGCCGCTGACC
GTCATGGTTGCCGGCCAGCCGCAGCATTTGGAGGTGAGCGCGCATGCTTAAAGGATTGCT
GTTCGACCTCGACGGCGTCTTGACCGACTCGGCCAAGTTCCACCTGCAGGCCTGGAGCCA
GCTGGCCACCCAGCTGGGCATCACCCTGACGCCGGCCGAGCGCGAAGGCCTGCGCGGCCG
CTCGCGGCTGGACTCGCTGAACCTGATTTTGGCGGCAGGCGCCCAGGAAGACCGGTTCAG
TGCCGCAGAGAAAACGGCGCTAACCGACCAGAAGAACGCGGTGTACCTGAAGCTGATTCA
GACGATGACGCCGGTGGACATCCTGCCGGGCATTCCGCAACTGCTGAAGGACGCGCAGGC
GGCCGGCCTGAAAATGGCAATCGCCTCGGCGTCGCGGAACGCCCCGACAATTCTTGACCA
CCTGGGCCTGGCCGCCAGTTTCGACGCCATCGTCGATCCGGCGACCCTGCACCGCGGCAA
GCCCGACCCGGAGATCTACCAGCAGGCGCAAGCGCTGCTGGGGCTCCAGGCCGCCGAGGT
GATCGGCTTCGAGGATGCCTCGGCCGGGGTCGCCGCCATCAAAGCGGCCGGTCAGTTCGC
GGTTGGCATCGGGGATGCCCGGCTTCTGGCCGCAGCGGATTACCTAGTGAAAGACACGGC
GGCCCTGCAGCTGAGCCAGTTGCAAGCGGCGTTCGCCAAAGAAAGTGGGGAGACTAATGG
TTGAAATCGACTTGGACCACCTCTACAAGAAGTACGACGACGGCGAGGATTACTCGGTGG
TGGACTTCGACCTTCACATCAAGGATAAGGAGTTCATCGTGTTCGTCGGCCCCTCGGGCT
GCGGGAAGTCCACCACGCTGCGTATGATTGCGGGGCTGGAGGACATTACCAAAGGCGAGC
TGAAAATCGACGATAAGGTGATGAACGACGTGGCCCCAAGGACCGCAACATCGCCATGG
TGTTTCAGAACTACGCCTTGTACCCGCACATGTCAGTGTACGACAACATGGCGTTCGGCC
TAAAGCTACGGCACTACAAGAAGGAGGACATCGACAAACGCGTGCAAAACGCGGCGGAGA
TCCTCGGCCTGAAGCCGTTTCTCGACCGGAAGCCGGCCGCCTTGTCCGGGGGCCAGCGGC
AGCGGGTGGCCTTGGGCCGGGCCATCGTCCGCGACGCCCCAATTTTCCTGATGGATGAGC
CGTTGTCGAACCTGGACGCGAAGCTGCGGGTGTCCATGCGGGCGAAATCGCCAAGCTCC
ACCAGCGCCTGAACACCACCACGATTTACGTGACCCACGACCAAACCGAGGCCATGACTA
TGGCCGACCGGGTTGTCGTCATGTCCGTTGGCCACGTGCAGCAGATTGGCACCCCGGCCG
AGATTTACCAGAACCCGCGGAACCAGTTCGTGGCCGGGTTCATCGGGTCGCCGGCGATGA
ACTTCTTCAACATGACCTACCAGGACGGCTTCGTCAGCGACGGCCAAAGCATTCGCCTCA
```

-continued

```
AAGTGCCGGAAGGCCGGGCGAAGATTCTGGACGACCAAGGGTACAACGGCAAGGAAGTCG

TGTTCGGCATCCGGCCGGAGGACATCCATTCGGAGGAGGCCTTCCTGGAGACCTGGCCGG

ACGCGGTTATCAGCTCAACCGTGTCGGTGTCAGAGCTCCTGGGCGCCACCGAGCAGCTTT

ACCTGAAGGCGGATGACACCGAGTACGTTGCCAACGTCAACGCGCGCGACTTCCACAATC

CCGGGGATCATGTGAAAATGGGCTTCGACGTCAACAAGGCGCACTTCTTCAACAAGGACA

CGACCATGGCCATCGTGGCTAAGCCGATTCCGCTGGAAGGCTGAGGAGGTGAGTGCATGA

CCCCATGGTGGCAGCAAGCCGTCATTTACCAGATCTACCCGAAGAGTTTTCAGGACAGCA

ACGGGGATGGCATCGGCGATTTGCCGGGGATTACCAGTCGCCTTGATTACCTTAAGCGGC

TGGGCGTCGATGCCCTTTGGCTGAGCCCAGTGTATGTGTCGCCCGGCGAGGACAACGGCT

ACGACATCGCGGACTACGAGGCCATCGATCCCCAGTTCGGGACGATGGCCGACATGGACG

CCTTGATCGCCGCCGCCAAGCAGCGCG

SEQ ID NO: 17 Position 2793833..2794809
CCCGCGATTTTGGCGTGATTGGCTTCGACGGGGTATTCCTGGACCAGGTGTCCAACCCCA

AGCTGACCACGGTGAAGCAGCCCGTGCAGCGCCTCGGCGAACTGCTGGCCCGCATGCTCC

TGCAGAAGGTGGCACAGTCCGGCGCCCAACAGGGGGAGCTGCTGGTCGATCCTGAGCTGA

TTGCTCGGGACACGACGCGAAAGTAGATCGGATTTCAACTGTCCTTACCGCTATGGTAGG

GCCAGTTTTTAGGCTCTATGTCAAATCTAATTCATAGCTAATAGTTGATTTGGCAACGCC

TAAGGCGTCAGCCATATCTTGGTAAGTATGATGGCCTTCACTGACCAGTTGAGCTAGCGC

ACCACGTTGAAAACGTGATAAAGTAGAAGTACCCAAAGTAATCACTCCTTATAGCTGGTT

GGAATTAACTACTCCATTGTAAGAGATTGCTTTGGGCCTTTTTTATTTTTGTTCGGATT

AATTATAGAATTTGTCTAATTAGTTGAAAATTCTTAGGGTTGCCCATATATCTTTTAGTC

TGGTCATTAGTTTTTATGTTTGATCTGCTTTTTTCTGATCGCAAACACCCACAACTGCGA

GTGAGTCCTTTTTGAAGTCGTTGACTGTCAACAATACATTTATTTCCACATTGACATTGA

CAGAGCCAAAGCGCGTTGCCATTAGAACTGCTTCCAAAAAAGCTAATAACTGTGAGTCGC

CCAAACGTTTGATTAGCTAAATCGATACGCTTTTGCATACTAATCCTCCCGCTTGATAAG

AAGGTACTTAAATAGTTGCTTTCAATTGATCTAATCGCCATTGGCACCATGAAATAAAGG

CTAATTCGTCAATCTTTGGAATGCCATAGGTTCTAGCATACGTTAACTTTTGAGTGGTGA

GTAGTTGATCATAGGGTTTACTAATAATACCAACCACAAGGATATCGACTTTTTTGTCAA

TCCCGTTGACAGGCTTT

SEQ ID NO: 18 Position 2967081..2968319
AAATACGCAAAAGAACCCGACGAGAGTTAAGTCTCATCGGGTTCTCAGTCGTGGATGAAT

TAGAAGCATTGTTAGCTGCATAACCTTCAACATAGGATCAATAGCTGGTTAGATGGTCAT

CTCTCAGACTGTTTGCACCAGATCCAGGCAAACGTGTTTATATCCTTGGTCATACTCAGG

ATAGATGGGCATTGTGAGTGCAACAGGACTTAGTTGCTTGTATGCTAGGCAATGTTGGCC

TTGATACAGAGGATCACTCTGTTTCTGATCTGGATGATAACCTCGTTTTTCCATTTCAGG

ACGCTGTCCCAATAATTGTTGCCCTGGGAGTTTGTCGAATTAAGTCTTGGTGCCACAAAC

ACACGCTACGGCTTCTTTTCTTGCAAACTGATCTTAGTATTTAGGGCAGTTGCATGATTA

CGGAATTGAACCATTTTATAATGAATCGTCTTTTCTATAAGTCTATAGAAAGTGCAGGTA

ATGGCATTTTCTCCAGATCGGATTGTCTAATCAATTTAATTGATTTTTTTGGTGTGTTTG

ATTATATTGCTTTTGCAAAGGTACAATATACCTTTTCTCTGCTGCCTTGCGAGCAGCGAT

GGCATCCTCCATATGAACATATACACGATTTAGGACAAGATGGCCTTGAAAGTACAGCCT
```

```
-continued
TGCGACCCACTTTTGAGCAGTTTTATCCCAACTAACTCCGATAACGCCAGATTTGTTATT

GGACCGTTTAAGTGTAGAAGCAACTAAATTTGTTCGATTAATTAGTTGAAAATTCTTGGG

ATTGCCCATGTATTTTTAGTCTGGTTATTAGCTTTTATGTTTGATCTGCTTATTTCTGA

TCGCAAACACCCACAACTGCGAGTGAGTCCTTTTTGAAGTCGTTGACTGTCAACGATACA

TTTATTTCCACATTGACATTGACAGAGCCAAAGCGCGTTTCCATTAGAACTGCTTCCAAA

AAAACTAATGACTGTGAGTCGTCCAAACGTTTGATTGGCCAAATCGATACGCTTTTGCAT

ACTAATCTCCCCGTTTGATAAGAAGGTACTTAAAGAGTTGTTTTCAATTGATCTAGTCGC

CATTGGCACCATGAAATAAAGGCTAATTCGTCAATCTTTGGAATGCCATAGGTTCTAGCA

TACGTTAACTTTTGAGTGGTAAGTAGTTGATCATAGGGTTTGCTAATAATACCAACCACA

AGGATATCGACATTTTTGTCAATCCCGTTGACAGGTTTT
```

Tables

TABLE 1

| SN1 | mg/L | SN2 | mg/L |
|---|---|---|---|
| oleic acid | 7.98 | fatty acid | <0.01 |
| decanoic acid | 1.30 | | |
| benzopropanoic acid | 2.69 | | |
| citric acid | 13.05 | | |

Fatty acid profile quantification of the fermented product supernatant of *Lactobacillus paracasei* strain CNCM I-5220 obtained from (A) first fermentation (SN1) and (B) second fermentation (SN2) process.

TABLE 2

| A | |
|---|---|
| SN1 m/z | SN2 m/z |
| NO signaL | 507.35 |
| | 527.23 |
| | 543.21 |
| | 612.15 |
| | 656.12 |
| | 689.22 |
| | 678.1 |
| | 694.09 |
| | 700.11 |
| | 705.18 |
| | 722.1 |
| | 738.07 |

| B | |
|---|---|
| SN2 | |
| Fractions | m/z |
| 1 | 705.23 |
| | 701.42 |
| | 689.25 |
| | 663.42 |
| | 647.44 |
| 2 | 705.24 |
| | 689.27 |
| | 664.12 |
| 4 | 671.2 |
| 5 | 855.35 |
| 6 | 855.35 |
| 7 | 855.35 |
| 8 | 855.35 |
| | 881.4 |
| | 651.25 |

| C SN2 | | | |
|---|---|---|---|
| Fractions | peptides | sequences | Protein |
| 5 | 855.35 | PDLKDVG (SEQ. ID NO: 19) | riboflavin byosintesis protein |
| 6 | 855.35 | PDLKDVG | riboflavin byosintesis protein |
| 7 | 855.35 | PDLKDVG | riboflavin byosintesis protein |
| 8 | 855.35 | PDLKDVG | riboflavin byosintesis protein |

Peptide profile of the fermented product supernatant of *Lactobacillus paracasei* strain CNCM I-5220 (first fermentation (SN1) and second fermentation (SN2) process) obtained from MALDI TOF mass spectrometry (A). Signals of interest from SN2 were profiled by MALDI TOF/TOF (B) mass spectrometry. (C) Peptides sequence profile of the fermented product supernatant of *Lactobacillus paracasei* strain CNCM I-5220 (second fermentation (SN2) process) obtained from MALDI TOF mass spectrometry. Fragmentation spectra of peptidic origin were interpreted and sequences confirmed by alignment with the BLAST program.

REFERENCES

Bokulich, N. A., Chung, J., Battaglia, T., Henderson, N., Jay, M., Li, H., A, D. L., Wu, F., Perez-Perez, G. I., Chen, Y., et al. (2016). Antibiotics, birth mode, and diet shape microbiome maturation during early life. Sci Transl Med 8, 343ra382.

Dahiya, D. K., Renuka, Puniya, M., Shandilya, U. K., Dhewa, T., Kumar, N., Kumar, S., Puniya, A. K., and Shukla, P. (2017). Gut Microbiota Modulation and Its Relationship with Obesity Using Prebiotic Fibers and Probiotics: A Review. Front Microbiol 8, 563.

Fernandes, R., do Rosario, V. A., Mocellin, M. C., Kuntz, M. G. F., and Trindade, E. (2017). Effects of inulin-type fructans, galacto-oligosaccharides and related synbiotics on inflammatory markers in adult patients with overweight or obesity: A systematic review. Clin Nutr 36, 1197-1206.

Gibson, G. R., Hutkins, R., Sanders, M. E., Prescott, S. L., Reimer, R. A., Salminen, S. J., Scott, K., Stanton, C., Swanson, K. S., Cani, P. D., et al. (2017). Expert consensus document: The International Scientific Association for Probiotics and Prebiotics (ISAPP) consensus statement on the definition and scope of prebiotics. Nat Rev Gastroenterol Hepatol 14, 491-502.

Goenka, A., and Kollmann, T. R. (2015). Development of immunity in early life. J Infect 71 Suppl 1, S112-120.

Mileti, E., Matteoli, G., Iliev, I. D., and Rescigno, M. (2009). Comparison of the immunomodulatory properties of three probiotic strains of Lactobacilli using complex culture systems: prediction for in vivo efficacy. PLoS One 4, e7056.

Shane, A. L., Sanchez, P. J., and Stoll, B. J. (2017). Neonatal sepsis. Lancet 390, 1770-1780.

Tsilingiri, K., Barbosa, T., Penna, G., Caprioli, F., Sonzogni, A., Viale, G., and Rescigno, M. (2012). Probiotic and postbiotic activity in health and disease: comparison on a novel polarised ex-vivo organ culture model. Gut 61, 1007-1015.

---

The invention claimed is:

1. A composition comprising a fermented supernatant of *Lactobacillus casei* or *paracasei* species, wherein the species comprises at least one DNA sequence at least 95% identical to one of the sequences selected from the group consisting of: SEQ ID NOs: 1 to 5, and wherein the fermented supernatant is obtained by a method comprising:
   a) fermenting an inoculum of the *Lactobacillus* strain in a suitable culture medium so as to obtain a first biomass and a first supernatant;
   b) separating the first biomass from the first supernatant;
   c) fermenting the first biomass in a minimum solution to obtain the fermented supernatant;
   wherein the minimum solution consists of:
   prebiotic fibers in water; or
   prebiotic fibers in a saline solution, a phosphate buffer, an isotonic solution or a hypotonic solution;
   wherein the *Lactobacillus casei* or *paracasei* species are separated from the composition; and
   wherein the composition is useful in the treatment or prevention of infections or in the treatment and/or prevention of immunopathologies derived from an exaggerated inflammatory response.

2. The composition according to claim 1 wherein the prebiotic fibers are selected from the group consisting of fructooligosaccharides (FOS), nondigestible oligosaccharides (NDOs), resistant starch, pectin, beta-glucans, inulin, lactulose, polydextrose, isomaltooligosaccharides (IMO), lactitol, chicory root inulin-derived FOS, wheat bran-derived arabinoxylooligosaccharides (AXOS), xylooligosaccharides (XOS), mannitol, maltodextrin, raffinose, sorbitol, galactooligosaccharides (GOS) and combinations thereof.

3. The composition according to claim 1 wherein the prebiotic fibers are FOS.

4. The composition according to claim 1 wherein the fermented supernatant is a dry powder.

5. The composition according to claim 1 wherein the fermentation is carried out at a temperature of 25-40° C.

6. The composition according to claim 1, wherein the fermented supernatant comprises a fatty acid concentration <0.01 mL.

7. The composition according to claim 1, wherein the fermented supernatant, when analyzed by MALDI TOF/TOF mass spectrometry, is characterized by a peptide signal profile having the following m/z values: 705.23, 701.42, 689.25, 663.42 and 647.44 in the first fraction, 705.24, 689.27, and 664.12 in the second fraction, 671.2 in the fourth fraction, 855.35 in the fifth fraction, 855.35 in the sixth fraction 855.35 in the seventh fraction, and 855.35, 881.4, and 651.25 in the eighth fraction.

8. The composition according to claim 1, wherein the fermented supernatant comprises at least the peptide of SEQ ID NO: 19.

9. The composition according to claim 1, wherein the fermented supernatant is obtainable by a method comprising:
   a) growing an inoculum of the *Lactobacillus casei* or *paracasei* species in a suitable culture medium, at a temperature ranging from 4 to 40° C., to have a biomass and allowing fermentation of said biomass to proceed for 12 to 36 hours, to get a fermented biomass;
   b) centrifuging said fermented biomass to get a pellet fermented biomass and a first fermented product;
   c) incubating said pellet fermented biomass into a minimum solution and allowing further fermentation for 12 to 36 hours, at a temperature ranging from 4 to 40° C., to get a further fermented biomass; and,
   d) separating said further fermented biomass from a second fermented product by centrifugation,
   wherein the minimum solution of step c) comprises prebiotic fibers.

10. The composition according to claim 1, wherein the species are characterized by comprising in their DNA genome DNA at least 95% identical to SEQ ID NOs: 1 to 5.

11. The composition according to claim 1, wherein the *Lactobacillus* species is *Lactobacillus paracasei*.

12. The composition according to claim 11, wherein the *Lactobacillus paracasei*; is a strain characterized by comprising in its DNA genome at least one DNA sequence at least 95% identical to SEQ ID NOs: 6 to 18.

13. The composition according to claim 1 wherein the *Lactobacillus paracasei* is the strain deposited with the collection Nationale de Cultures de Microorganismes (CNCM) according to the Budapest Treaty with accession no. CNCM I-5220.

14. The composition according to claim 1 the form of a topical or solid formulation, or a formulation introduced in an enema for external or internal use.

15. The composition according to claim 1 wherein the fermented supernatant is present at 0.02-40% weight/volume (w/v), optionally 1% weight/volume (w/v).

16. The composition according to claim 1 further comprising adjuvants and/or therapeutic agents.

17. The composition according to claim 16, further comprising a therapeutic agent, wherein the therapeutic agent is an anti-inflammatory drug.

18. The composition according to claim 1 wherein the minimum solution consists essentially of a solution that does not contain carbon and/or nitrogen sources or micromolar concentration of minerals.

19. A probiotic, pharmaceutical, nutraceutical, cosmetic, food, food supplement or feed composition comprising the composition according to claim 1.

20. A method for obtaining a fermented supernatant, comprising:
   a) growing an inoculum of *Lactobacillus* strain as defined in claim 1 in a suitable culture medium, at a temperature ranging from 4 to 40° C., to have a biomass and allowing fermentation of said biomass to proceed for 12 to 36 hours, to get a fermented biomass;
   b) centrifuging said fermented biomass to get a pellet fermented biomass and a first fermented product;
   c) incubating said pellet fermented biomass into a minimum solution and allowing further fermentation for 12 to 36 hours, at a temperature ranging from 4 to 40° C., to get a further fermented biomass;
   d) separating said further fermented biomass from a second fermented product by centrifugation,
   wherein the minimum solution of step c) comprises prebiotic fibers.

21. The method according to claim 20, wherein the minimum solution is a solution which does not contain carbon and/or nitrogen sources or micromolar concentration of minerals.

22. The fermented supernatant obtainable by the method of claim 20.

* * * * *